US009352049B2

(12) United States Patent
Guzzo et al.

(10) Patent No.: US 9,352,049 B2
(45) Date of Patent: May 31, 2016

(54) LIGAND-THERAPEUTIC AGENT CONJUGATES, SILICON-BASED LINKERS, AND METHODS FOR MAKING AND USING THEM

(71) Applicant: Albany Molecular Research, Inc., Albany, NY (US)

(72) Inventors: Peter R. Guzzo, Niskayuna, NY (US); David D. Manning, Duanesburg, NY (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

(21) Appl. No.: 14/209,460

(22) Filed: Mar. 13, 2014

(65) Prior Publication Data

US 2014/0274951 A1    Sep. 18, 2014

Related U.S. Application Data

(60) Provisional application No. 61/784,906, filed on Mar. 14, 2013.

(51) Int. Cl.
*A61K 47/48* (2006.01)
*C07D 519/04* (2006.01)
*A61K 38/00* (2006.01)

(52) U.S. Cl.
CPC .......... *A61K 47/48107* (2013.01); *A61K 38/00* (2013.01); *A61K 47/48384* (2013.01); *A61K 47/48715* (2013.01); *C07D 519/04* (2013.01)

(58) Field of Classification Search
CPC ............................................. A61K 47/48061
USPC .................. 514/63; 530/391.9, 300; 540/478
See application file for complete search history.

(56) References Cited

U.S. PATENT DOCUMENTS

| 6,476,079 | B1 | 11/2002 | Jukarainen et al. |
| 7,902,176 | B2 | 3/2011 | Harats et al. |
| 2002/0115595 | A1 | 8/2002 | Grissom et al. |
| 2007/0281320 | A1 | 12/2007 | Sabbadini et al. |
| 2008/0138334 | A1 | 6/2008 | Sabbadini et al. |
| 2008/0145360 | A1 | 6/2008 | Sabbadini et al. |
| 2011/0009588 | A1 | 1/2011 | Hsieh et al. |
| 2011/0165063 | A1 | 7/2011 | Hsieh et al. |
| 2012/0130045 | A1 | 5/2012 | Hammond et al. |

FOREIGN PATENT DOCUMENTS

| WO | 8910754 A1 | 11/1989 |
| WO | 2005082023 A2 | 9/2005 |
| WO | 2009132265 A2 | 10/2009 |
| WO | 2012037358 A1 | 3/2012 |
| WO | 2012075087 A2 | 6/2012 |
| WO | 2012075114 A2 | 6/2012 |
| WO | 2012075147 A2 | 6/2012 |
| WO | 2012113847 A1 | 8/2012 |
| WO | 2012131527 A1 | 10/2012 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Wohl et al., "Silicate Esters of Paclitaxel and Docetaxel: Synthesis, Hydrophobicity, Hydrolytic Stability, Cytotoxicity, and Prodrug Potential," J. Med. Chem. Epub ahead of print Mar. 6, 2014.
Hu et al., "Multicolor, One- and Two-Photon Imaging of Enzymatic Activities in Live Cells with Fluorescently Quenched Activity-Based Probes (gABPs)," J. Am. Chem. Soc. 133:12009-12020 (2011).
Parrott et al., "Tunable Bifunctional Silyl Ether Cross-Linkers for the Design of Acid-Sensitive Biomaterials," J. Am. Chem. Soc. 132:17928-17932 (2010).
Chiu et al., "Synthesis, Hydrolytic Reactivity, and Anticancer Evaluation of N- and O-Trioganosilyated Compounds as New Types of Potential Prodrugs," J. Pharm. Sci. 71(5):542-551 (1982).
Millership et al., "Prodrugs Utilizing Organosilyl Derivation: An Investigation of the Long-term Androgenic and Myotrophic Activities of Silyl Derivatives of Testosterone," J. Pharm. Sci. 77(2):116-119 (1988).
Leamon et al., "Delivery of Macromolecules into Living Cells: A Method That Exploits Folate Receptor Endocytosis" Proc. Natl. Acad. Sci. U.S.A. 88(13):5572-5576 (1991).
International Search Report and Written Opinion of the International Preliminary Examining Authority for International Patent Application No. PCT/US2014/026282 (Jul. 14, 2014).
International Preliminary Report on Patentability and Written Opinion of the International Preliminary Examining Authority for International Patent Application No. PCT/US2014/026282 (Sep. 24, 2015).

* cited by examiner

*Primary Examiner* — Kristin Vajda
(74) *Attorney, Agent, or Firm* — LeClairRyan, a Professional Corporation

(57) ABSTRACT

The present invention relates to ligand-therapeutic agent conjugate compounds, silicon linkers for the conjugate compounds, compositions, methods for making them, and methods for the treatment of cancer using the conjugate compounds. The silicon-based linkers described herein can be used to deliver desired therapeutic agents to particular cells or tissue types targeted by the ligand.

32 Claims, 2 Drawing Sheets

LIGAND-THERAPEUTIC AGENT CONJUGATES, SILICON-BASED LINKERS, AND METHODS FOR MAKING AND USING THEM

This application claims the priority benefit of U.S. Provisional Patent Application Ser. No. 61/784,906, filed Mar. 14, 2013, which is hereby incorporated by reference in its entirety.

FIELD OF THE INVENTION

The present invention relates to conjugate compounds, silicon linker compounds, compositions, methods for making them, and methods for the treatment of diseases using the conjugate compounds. In particular, the present invention relates to such compounds, compositions, and methods, where the compounds include novel silicon linkers.

BACKGROUND OF THE INVENTION

Drug delivery technology has been used extensively for the purpose of delivering agents to desired targets for many years. A variety of methods and routes of administration have been developed to deliver pharmaceuticals, such as small molecular drugs and other biologically active compounds (e.g., peptides, hormones, proteins, and enzymes). Examples of various drug delivery methods are disclosed, for example, in WO 2012/037358, WO 2009/132265, WO 2005/082023, WO 2012/113847, WO 2012/131527, Chiu et al., "Synthesis, Hydrolytic Reactivity, and Anticancer Evaluation of N- and O- Trioganosilyated Compounds as New Types of Potential Prodrugs," *J. Pharm. Sci.*, 71(5):542-551 (1982), Millership et al., "Prodrugs Utilizing Organosilyl Derivation: An Investigation of the Long-term Androgenic and Myotrophic Activities of Silyl Derivatives of Testosterone," *J. Pharm. Sci.*, 77(2):116-119 (1988), Parrott et al., "Tunable Bifunctional Silyl Ether Cross-Linkers for the Design of Acid-Sensitive Biomaterials," *J. Am. Chem. Soc,* 132:17928-17932 (2010), and Leamon et al., "Delivery of Macromolecules into Living Cells: A Method That Exploits Folate Receptor Endocytosis" *Proc. Natl. Acad. Sci. U.S.A.* 88(13):5572-5576 (1991). Drug delivery technologies include liposomes and nano or microparticles.

Recently, antibody-drug conjugates (ADCs) have been devised to enhance the efficacy of antibody therapy. ADCs consist of a targeting antibody, a cytotoxic drug (warhead or therapeutic agent), and a linker system that attaches the two. With this delivery method, release of the free drug is normally necessary for the drug to elicit its desired action. Common techniques of releasing the cytotoxic drug include hydrazone hydrolysis, enzymatic cleavage of peptides (e.g. p-aminobenzyl alcohol release technology, WO 2005/082023), and reduction of disulfides. Certain other functional moieties have been used such as esters, but esters often can be too labile to achieve the long plasma half-lives desired for the intact conjugate.

Silyl ethers are a group of compounds which contain a silicon atom covalently bonded to an alkoxy group. The general structure is $R_1R_2R_3Si-O-R_4$ where $R_4$ is an alkyl group or an aryl group. Silyl ethers are commonly used as protecting groups of an alcohol functional group during organic synthesis (Wuts et al., "Greene's Protective Groups in Organic Synthesis," $4^{th}$ edition. John Wiley & Sons, Inc. Hoboken, N.J. (2007)). $R_1R_2R_3$ substituents can be widely varied providing access to a large array of silyl ethers that can possess differential properties. This feature makes silyl ethers attractive for application in selective protection and deprotection schemes in synthetic organic chemistry. The steric bulk and electronic properties of the substituents as well as the capacity of silicon to allow hypervalent species allow for a wide range of selective chemistry during formation and deprotection of silyl ether groups. Silyl ethers can be hydrolytically cleaved thereby providing a means to release free drug in an in vivo environment. Acid labile triggers such as hydrazones are known in the ADC field (Flygare et al. "Antibody-Drug Conjugates for the Treatment of Cancer," *Chem Biol Drug Des.*, 81:113-121 (2013)). The increased acidic environment of the endosomes (pH 5.5-6.2) and lysosomes (pH 4.5-5.0) relative to systemic circulation (pH 7.4-7.5) are thought to release the active drug. Silyl ether hydrolysis rates can be varied by changing the $R_1R_2R_3$ substituents.

Accordingly, there is a need in the art for compounds and methods useful to facilitate delivery and release of desired compounds to a site of interest.

The present invention is directed to overcoming these and other deficiencies in the art.

SUMMARY OF THE INVENTION

The present invention relates to conjugate compounds represented by formula (I) having the following structure:

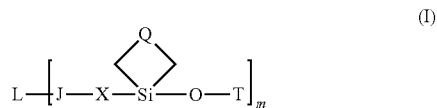

wherein
L is a cell-targeting ligand;
T is a therapeutic agent;
J is a linker group;
X is independently selected from the group consisting of:
(1) a bond;
(2) O;
(3)

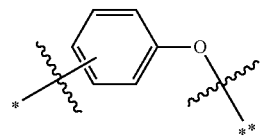

which is independently and optionally substituted from 1 to 2 times with $R^8$, wherein the wavy lines indicate point of attachment sites and * is the point of attachment to J and ** is the point of attachment to Si; and
(4)

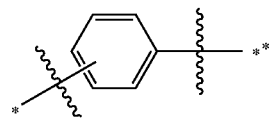

which is independently and optionally substituted from 1 to 2 times with $R^8$, wherein the wavy lines indicate point of attachment sites and * is the point of attachment to J and ** is the point of attachment to Si;

Q is —(CH$_2$)$_n$—, —CH$_2$CHR$^1$CH$_2$—, —CH$_2$CR$^5$R$^6$CH$_2$—, —CH$_2$CHR$^1$CH$_2$CH$_2$—, —CH$_2$CH$_2$CHR$^1$CH$_2$CH$_2$—, —CH$_2$X$^1$CH$_2$—, or —CH$_2$CH$_2$X$^1$CH$_2$CH$_2$—;

R$^1$ is C$_{1-6}$ alkyl, aryl, heteroaryl, OR$^5$, NR$^5$R$^6$, or —N(COR$^2$)R$^7$, each of which is optionally substituted with R$^8$;

R$^2$ is H, C$_{1-6}$ alkyl, C$_{3-6}$ cycloalkyl, aryl, or heteroaryl, each of which is optionally substituted with R$^8$;

R$^3$ is H, C$_{1-6}$ alkyl, C$_{3-6}$ cycloalkyl, or —COR$^4$, each of which is optionally substituted with R$^8$;

R$^4$ is H, C$_{1-6}$ alkyl, or C$_{3-6}$ cycloalkyl, each of which is optionally substituted with R$^8$;

R$^5$ is H or C$_{1-6}$ alkyl optionally substituted with R$^8$;

R$^6$ is H or C$_{1-6}$ alkyl optionally substituted with R$^8$; or

R$^5$ and R$^6$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, C$_1$-C$_4$ alkyl, C$_1$-C$_4$ haloalkyl, and C$_1$-C$_4$ alkoxy;

R$^7$ is H, C$_{1-6}$ alkyl, C$_{3-6}$ cycloalkyl, aryl, or heteroaryl, each of which is optionally substituted with R$^8$;

R$^8$ is H, NO$_2$, CN, halogen, oxo, C$_{1-6}$ alkyl, C$_{1-6}$ haloalkyl, C$_{1-6}$ hydroxyalkyl, C$_{1-6}$ alkoxyalkyl, C$_{3-6}$ cycloalkyl, C$_{4-7}$ cycloalkylalkyl, aryl, heteroaryl, COOR$^9$, COR$^9$, C(O)NR$^9$R$^{10}$, COONR$^9$R$^{10}$, SO$_2$R$^9$, SO$_2$NR$^9$R$^{10}$, or OR$^9$;

R$^9$ is H, C$_{1-6}$ alkyl, C$_{3-6}$ cycloalkyl, aryl, or heteroaryl, wherein the C$_{1-6}$ alkyl, C$_{3-6}$ cycloalkyl, aryl, or heteroaryl is optionally substituted from 1 to 3 times with halogen, hydroxyl, cyano, oxo, C$_1$-C$_4$ alkyl, C$_1$-C$_4$ haloalkyl, or C$_1$-C$_4$ alkoxy;

R$^{10}$ is H, C$_{1-6}$ alkyl, C$_{3-6}$ cycloalkyl, aryl, or heteroaryl, wherein the C$_{1-6}$ alkyl, C$_{3-6}$ cycloalkyl, aryl, or heteroaryl is optionally substituted from 1 to 3 times with halogen, hydroxyl, cyano, oxo, C$_1$-C$_4$ alkyl, C$_1$-C$_4$ haloalkyl, or C$_1$-C$_4$ alkoxy; or R$^9$ and R$^{10}$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, C$_1$-C$_4$ alkyl, C$_1$-C$_4$ haloalkyl, and C$_1$-C$_4$ alkoxy;

X$^1$ is O, S, SO, SO$_2$, or NR$^3$;

n is 1 to 5; and m is 1 to 8.

The present invention also relates to a compound represented by formula (II) having the following structure:

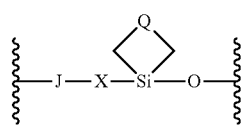

(II)

wherein the wavy lines indicate point of attachment sites and wherein:

J is a linker group;

X is independently selected from the group consisting of:

(1) a bond;

(2) O;

(3)

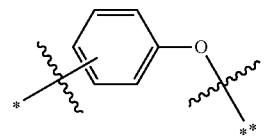

which is independently and optionally substituted from 1 to 2 times with R$^8$, wherein the wavy lines indicate point of attachment sites and * is the point of attachment to J and ** is the point of attachment to Si; and (4)

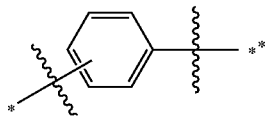

which is independently and optionally substituted from 1 to 2 times with R$^8$, wherein the wavy lines indicate point of attachment sites and * is the point of attachment to J and ** is the point of attachment to Si;

Q is —(CH$_2$)$_n$—, —CH$_2$CHR$^1$CH$_2$—, —CH$_2$CR$^5$R$^6$CH$_2$—, —CH$_2$CHR$^1$CH$_2$CH$_2$—, —CH$_2$CH$_2$CHR$^1$CH$_2$CH$_2$—, —CH$_2$X$^1$CH$_2$—, or —CH$_2$CH$_2$X$^1$CH$_2$CH$_2$—;

R$^1$ is C$_{1-6}$ alkyl, aryl, heteroaryl, OR$^5$, NR$^5$R$^6$, or —N(COR$^2$)R$^7$, each of which is optionally substituted with R$^8$;

R$^2$ is H, C$_{1-6}$ alkyl, C$_{3-6}$ cycloalkyl, aryl, or heteroaryl, each of which is optionally substituted with R$^8$;

R$^3$ is H, C$_{1-6}$ alkyl, C$_{3-6}$ cycloalkyl, or —COR$^4$, each of which is optionally substituted with R$^8$;

R$^4$ is H, C$_{1-6}$ alkyl, or C$_{3-6}$ cycloalkyl, each of which is optionally substituted with R$^8$;

R$^5$ is H or C$_{1-6}$ alkyl optionally substituted with R$^8$;

R$^6$ is H or C$_{1-6}$ alkyl optionally substituted with R$^8$; or

R$^5$ and R$^6$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, C$_1$-C$_4$ alkyl, C$_1$-C$_4$ haloalkyl, and C$_1$-C$_4$ alkoxy;

R$^7$ is H, C$_{1-6}$ alkyl, C$_{3-6}$ cycloalkyl, aryl, or heteroaryl, each of which is optionally substituted with R$^8$;

R$^8$ is H, NO$_2$, CN, halogen, oxo, C$_{1-6}$ alkyl, C$_{1-6}$ haloalkyl, C$_{1-6}$ hydroxyalkyl, C$_{1-6}$ alkoxyalkyl, C$_{3-6}$ cycloalkyl, C$_{4-7}$ cycloalkylalkyl, aryl, heteroaryl, COOR$^9$, COR$^9$, C(O)NR$^9$R$^{10}$, COONR$^9$R$^{10}$, SO$_2$R$^9$, SO$_2$NR$^9$R$^{10}$, or OR$^9$;

R$^9$ is H, C$_{1-6}$ alkyl, C$_{3-6}$ cycloalkyl, aryl, or heteroaryl, wherein the C$_{1-6}$ alkyl, C$_{3-6}$ cycloalkyl, aryl, or heteroaryl is optionally substituted from 1 to 3 times with halogen, hydroxyl, cyano, oxo, C$_1$-C$_4$ alkyl, C$_1$-C$_4$ haloalkyl, or C$_1$-C$_4$ alkoxy;

$R^{10}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy; or $R^9$ and $R^{10}$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy;

$X^1$ is O, S, SO, $SO_2$, or $NR^3$; and n is 1 to 5.

A further aspect of the present invention relates to a conjugate compound represented by formula (III) having the following structure:

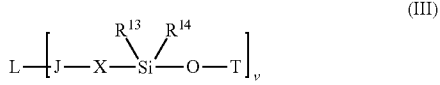

(III)

wherein

L is a cell-targeting ligand;

T is a therapeutic agent;

J is a linker group, with the proviso that when X is a bond, J cannot directly bond to the silicon atom with an O, NH, N—$CH_3$, S, or carboxyl and forms a hydrolytically stable carbon bond with the silicon atom;

X is independently selected from the group consisting of:

(1) a bond;

(2)

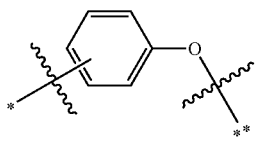

which is independently and optionally substituted from 1 to 2 times with $R^{15}$, wherein the wavy lines indicate point of attachment sites and * is the point of attachment to J and ** is the point of attachment to Si; and (3)

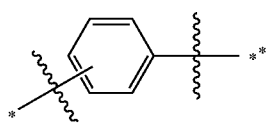

which is independently and optionally substituted from 1 to 2 times with $R^{15}$, wherein the wavy lines indicate point of attachment sites and * is the point of attachment to J and ** is the point of attachment to Si;

$R^{13}$ and $R^{14}$ are each independently selected from the group consisting of $C_{1-6}$ alkyl, $C_{3-6}$ cycloalkyl, aryl, and heteroaryl, each of which is optionally substituted with $R^{16}$;

$R^{15}$ is H, $C_{1-6}$ alkyl, $C_{1-6}$ haloalkyl, $C_{1-6}$ hydroxyalkyl, $C_{1-6}$ alkoxyalkyl, $C_{3-6}$ cycloalkyl, $C_{4-7}$ cycloalkylalkyl, CN, halogen, $NO_2$, oxo, aryl, heteroaryl, $OR^{17}$, $COOR^{17}$, $COR^{17}$, $CONR^{17}R^{18}$, $COONR^{17}R^{18}$, $SO_2R^{17}$, or $SO_2NR^{17}R^{18}$;

$R^{16}$ is H, $C_{1-6}$ alkyl, $C_{1-6}$ haloalkyl, $C_{1-6}$ alkoxyalkyl, $C_{3-6}$ cycloalkyl, $C_{4-7}$ cycloalkylalkyl, CN, halogen, $NO_2$, $OR^{17}$, $NR^{17}R^{18}$, $COOR^{17}$, $COR^{17}$, $CONR^{17}R^{18}$, $SO_2R^{17}$, —$SO_2NR^{17}R^{18}$, aryl, or heteroaryl;

$R^{17}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;

$R^{18}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy; or $R^{17}$ and $R^{18}$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy; and v is 1 to 8.

Another aspect of the present invention relates to a compound represented by formula (IV) having the following structure:

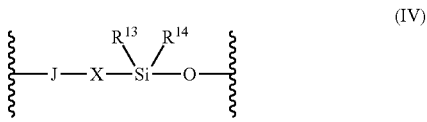

(IV)

wherein the wavy lines indicate point of attachment sites and wherein:

J is a linker group, with the proviso that when X is a bond, J cannot directly bond to the silicon atom with an O, NH, N—$CH_3$, S, or carboxyl and forms a hydrolytically stable carbon bond with the silicon atom;

X is independently selected from the group consisting of:

(1) a bond;

(2)

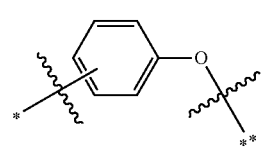

which is independently and optionally substituted from 1 to 2 times with $R^{15}$, wherein the wavy lines indicate point of attachment sites and * is the point of attachment to J and ** is the point of attachment to Si; and (3)

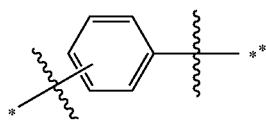

which is independently and optionally substituted from 1 to 2 times with $R^{15}$, wherein the wavy lines indicate point of attachment sites and * is the point of attachment to J and ** is the point of attachment to Si;

$R^{13}$ and $R^{14}$ are each independently selected from the group consisting of $C_{1-6}$ alkyl, $C_{3-6}$ cycloalkyl, aryl, and heteroaryl, each of which is optionally substituted with $R^{16}$;

$R^{15}$ is H, $C_{1-6}$ alkyl, $C_{1-6}$ haloalkyl, $C_{1-6}$ hydroxyalkyl, $C_{1-6}$ alkoxyalkyl, $C_{3-6}$ cycloalkyl, $C_{4-7}$ cycloalkylalkyl, CN, halogen, $NO_2$, oxo, aryl, heteroaryl, $OR^{17}$, $COOR^{17}$, $COR^{17}$, $CONR^{17}R^{18}$, $COONR^{17}R^{18}$, $SO_2R^{17}$, or $SO_2NR^{17}R^{18}$;

$R^{16}$ is H, $C_{1-6}$ alkyl, $C_{1-6}$ haloalkyl, $C_{1-6}$ alkoxyalkyl, $C_{3-6}$ cycloalkyl, $C_{4-7}$ cycloalkylalkyl, CN, halogen, $NO_2$, $OR^{17}$, $NR^{17}R^{18}$, $COOR^{17}$, $COR^{17}$, $CONR^{17}R^{18}$, $SO_2R^{17}$, —$SO_2NR^{17}R^{18}$, aryl, or heteroaryl;

$R^{17}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;

$R^{18}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy; or $R^{17}$ and $R^{18}$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy.

The present invention also relates to pharmaceutical compositions and methods of treating diseases, such as cancer, using the conjugate compounds and pharmaceutical compositions described herein.

In accordance with the present invention, the right balance between releasing group stability and lability is achieved for linkers useful in ligand-therapeutic agent conjugates. To use the common releasing technologies, the therapeutic agent may require a specific functional group or must be appended with the desired group without affecting the drug's potency. For example, PAB technology normally uses amine-bearing drugs. An alternative method to release a drug moiety is provided herein. Attachment of the therapeutic agent via a common functional group, such as a hydroxyl group, is ideal since such groups are often found on natural product or natural product-based cytotoxics. Although commonly used as intermediates in organic synthesis, the use of silyl ether compounds found in the present invention as releasing moieties in the field of immunotoxins (i.e. antibody drug conjugates) or more broadly to targeted drug delivery, such as folate conjugates, can overcome the above limitations in the field of drug delivery. In the ligand-therapeutic agent conjugates herein, the therapeutic agent is preferentially cleaved at a particular cell or tissue type targeted by the ligand.

DETAILED DESCRIPTION OF THE INVENTION

Figure 1:
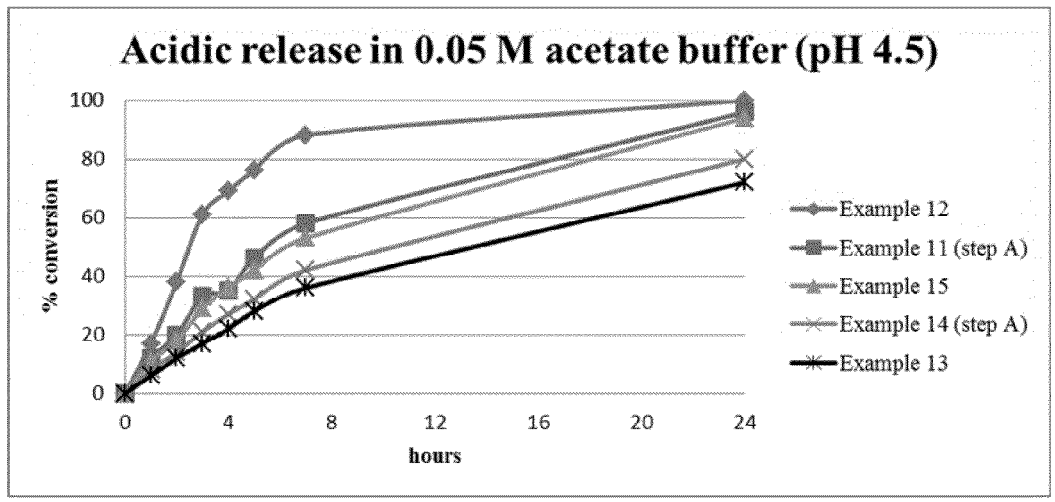
FIG. 1 is a graph showing percent conversion of benzyl ester derivatives to the desilylated parent vinca in acidic media as monitored by HPLC over 24 hours at pH 4.5.
Figure 1:
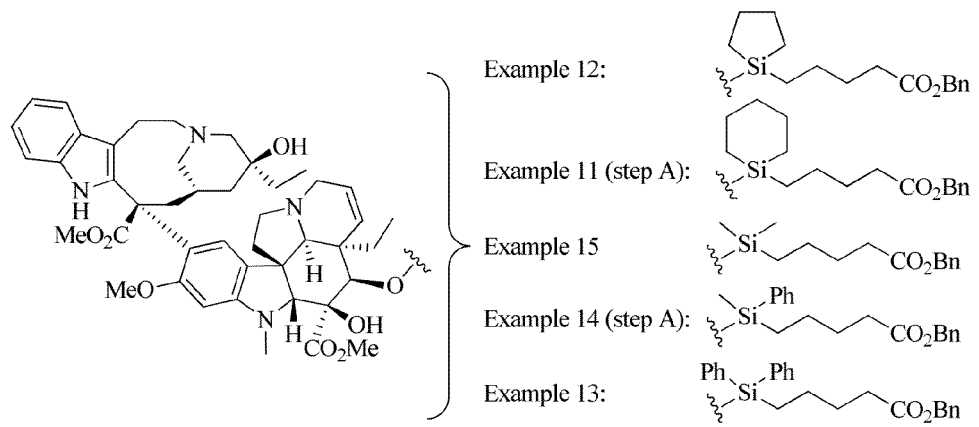

The present invention relates to conjugate compounds represented by formula (I) having the following structure:

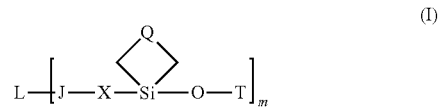

(I)

wherein
L is a cell-targeting ligand;
T is a therapeutic agent;
J is a linker group;
X is independently selected from the group consisting of:
(1) a bond;
(2) O;
(3)

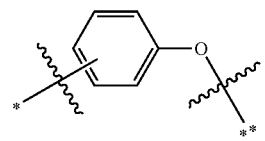

which is independently and optionally substituted from 1 to 2 times with $R^8$, wherein the wavy lines indicate point of attachment sites and * is the point of attachment to J and ** is the point of attachment to Si; and (4)

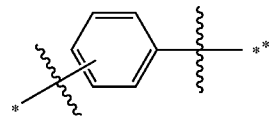

which is independently and optionally substituted from 1 to 2 times with $R^8$, wherein the wavy lines indicate point of attachment sites and * is the point of attachment to J and ** is the point of attachment to Si;

Q is —$(CH_2)_n$—, —$CH_2CHR^1CH_2$—, —$CH_2CR^5R^6CH_2$—, —$CH_2CHR^1CH_2CH_2$—, —$CH_2CH_2CHR^1CH_2CH_2$—, —$CH_2X^1CH_2$—, or —$CH_2CH_2X^1CH_2CH_2$—;

$R^1$ is $C_{1-6}$ alkyl, aryl, heteroaryl, $OR^5$, $NR^5R^6$, or —$N(COR^2)R^7$, each of which is optionally substituted with $R^8$;

$R^2$ is H, $C_{1-6}$ alkyl, $C_{3-6}$ cycloalkyl, aryl, or heteroaryl, each of which is optionally substituted with $R^8$;

$R^3$ is H, $C_{1-6}$ alkyl, $C_{3-6}$ cycloalkyl, or —$COR^4$, each of which is optionally substituted with $R^8$;

$R^4$ is H, $C_{1-6}$ alkyl, or $C_{3-6}$ cycloalkyl, each of which is optionally substituted with $R^8$;

$R^5$ is H or $C_{1-6}$ alkyl optionally substituted with $R^8$;

$R^6$ is H or $C_{1-6}$ alkyl optionally substituted with $R^8$; or $R^5$ and $R^6$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy;

$R^7$ is H, $C_{1-6}$ alkyl, $C_{3-6}$ cycloalkyl, aryl, or heteroaryl, each of which is optionally substituted with $R^8$;

$R^8$ is H, $NO_2$, CN, halogen, oxo, $C_{1-6}$ alkyl, $C_{1-6}$ haloalkyl, $C_{1-6}$ hydroxyalkyl, $C_{1-6}$ alkoxyalkyl, $C_{3-6}$ cycloalkyl, $C_{4-7}$ cycloalkylalkyl, aryl, heteroaryl, $COOR^9$, $COR^9$, $C(O)NR^9R^{10}$, $COONR^9R^{10}$, $SO_2R^9$, $SO_2NR^9R^{10}$, or $OR^9$;

$R^9$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;

$R^{10}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy; or $R^9$ and $R^{10}$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy;

$X^1$ is O, S, SO, $SO_2$, or $NR^3$;

n is 1 to 5; and m is 1 to 8.

As used above, and throughout the description of the invention, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 20 or fewer carbons. Lower alkyl refers to alkyl groups having about 1 to about 6 carbon atoms in the chain. Branched means that one or more lower alkyl groups such as methyl, ethyl or propyl are attached to a linear alkyl chain. Representative alkyl groups include methyl, ethyl, n-propyl, i-propyl, n-butyl, t-butyl, n-pentyl, 3-pentyl, and the like.

The term "haloalkyl" means both branched and straight-chain alkyl substituted with one or more halogen, wherein the alkyl group is as herein described.

When an alkyl is substituted from 1 to 3 times with halogen, the substituted groups include $CF_3$, $CF_2H$, $CH_2CF_3$, $CH_2CF_2H$, and the like.

The term "cycloalkyl" means a non-aromatic mono- or multicyclic ring system of about 3 to about 7 carbon atoms, preferably of about 5 to about 7 carbon atoms, and which may include at least one double bond. Exemplary cycloalkyl groups include, without limitation, cyclopropyl, cyclobutyl, cyclopentyl, cyclohexyl, cycloheptyl, cyclopropenyl, cyclobutenyl, cyclopentenyl, cyclophenyl, anti-bicyclopropane, and syn-tricyclopropane.

The term "cycloalkylalkyl" means a cycloalkyl-alkyl-group in which the cycloalkyl and alkyl are as defined herein. Representative cycloalkylalkyl groups include cyclopropylmethyl and cyclopentylmethyl. The alkyl radical and the cycloalkyl radical may be optionally substituted as defined herein.

The term "aryl" means an aromatic monocyclic or multicyclic (polycyclic) ring system (including fused, bridged, or spiro ring systems) of 6 to about 19 carbon atoms, preferably of 6 to about 10 carbon atoms, and includes arylalkyl groups. In the case of a multicyclic ring system, only one of the rings needs to be aromatic for the ring system to be defined as "aryl". The ring system of the aryl group may be optionally substituted. Representative aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "heteroaryl" means an aromatic monocyclic or multicyclic ring system (including fused, bridged, or spiro ring systems) of 5 to about 19 ring atoms, preferably of 5 to about 10 ring atoms, in which one or more of the atoms in the ring system is/are element(s) other than carbon, for example, nitrogen, oxygen or sulfur. In the case of a multicyclic ring system, only one of the rings needs to be aromatic for the ring system to be defined as "heteroaryl". A nitrogen, carbon, or sulfur atom in the heteroaryl ring may be optionally oxidized; the nitrogen may optionally be quaternized. Representative heteroaryl groups include pyridinyl, pyridyl, 2-oxo-pyridin-1(2H)-yl, pyrimidinyl, pyridazinyl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and 3-thio-[1,2,4]triazolo[4,3-a]pyridin-2(3H)-yl, and the like.

Heteroaryls may particularly include [1,2,4]triazolo[1,5-a]pyridin-6-yl, 7-methyl-[1,2,4]triazolo[1,5-a]pyridin-6-yl, [1,2,4]triazolo[4,3-a]pyridin-6-yl, 3-methyl-[1,2,4]triazolo[4,3-a]pyridin-6-yl, 3-(trifluoromethyl)-[1,2,4]triazolo[4,3-a]pyridin-6-yl, 3-oxo-[1,2,4]triazolo[4,3-a]pyridin-2(3H)-yl, 2-oxo-pyridin-1-yl, 6-aminopyridazin-3-yl, 6-(methoxy)pyridazin-3-yl, 6-(hydroxy)pyridazin-3-yl, 6-methylpyridazin-3-yl, 6-(trifluoromethyl)pyridazin-3-yl, 6-(difluoromethoxy)pyridazin-3-yl, 6-(hydroxy)pyridazin-3-yl, 4-cyanophenyl, 3-cyanophenyl, 4-(methylsulfonyl)phenyl, 2-oxo-2,3-dihydrobenzo[d]oxazol-6-yl, pyrimidin-5-yl, pyrazinyl, 5-aminopyrazinyl, quinoxalin-2-yl, 5-methyl-1,3,4-thiadiazol-2-yl, 4-(ethylsulfonyl)piperazin-1-yl, 6-(trifluoromethyl)pyridazin-3-yloxy, pyrazin-2-yloxy, 5-aminopyrazin-2-yloxy, 3-(pyridin-4-yl)propoxy, 3-(pyridin-3-yl)propoxy, 5-(methylsulfonyl)pyrimidin-2-yl, 6-(methylcarbamoyl)pyridazin-3-yl, and 6-carbamoylpyridazin-3-yl.

The term "heterocycle" or "heterocyclic" refers to a stable 3- to 18-membered ring (radical) which consists of carbon atoms and from one to five heteroatoms selected from the group consisting of nitrogen, oxygen, and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, butoxy, cyclopropyloxy, cyclohexyloxy, heptoxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

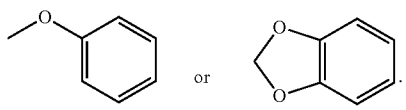

When the alkyl group of the "alkoxy" is substituted from 1 to 3 times with halogen, the "alkoxy" groups include $OCF_3$, $OCF_2H$, $OCH_2CF_3$, $OCH_2CF_2H$ and the like.

The term "halo" or "halogen" means fluoro, chloro, bromo, or iodo.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto or oxo (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent. As used herein, when an atom or group is optionally substituted multiple times, each such substitution is independently selected.

The term "compounds of the invention", and equivalent expressions, are meant to embrace compounds of general formulae (I)-(IV) as hereinbefore described. Also contemplated are the pharmaceutically acceptable salts and the solvates, e.g. hydrates, where the context so permits, as well as any stereoisomeric form, or a mixture of any such forms of that compound in any ratio. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Representative acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like. (See, for example Berge et al., *J Pharm Sci*, 66:1-sup.19 (1977) and *Remington's Pharmaceutical Sciences*, 17th ed, p. 1418, Mack Publishing Company, Easton, Pa. (1985), which are hereby incorporated by reference in their entirety.) Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide. Suitable amine base addition salts are prepared from amines which have sufficient basicity to form a stable salt, and preferably include the following amines which are frequently used in medicinal chemistry because of their low toxicity and acceptability for medical use: ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The term "therapeutically effective amounts" is meant to describe an amount of compound of the present invention effective in producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition and medical history, the particular compound used, as well as the carrier in which it is formulated and the route of administration selected for it; and, the nature and severity of the condition being treated.

The term "pharmaceutical composition" means a composition comprising compounds of formulae (I)-(IV) and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in *Remington's Pharmaceutical Sciences,* 17th ed, Easton, Pa., Mack Publishing Company (1985), which is hereby incorporated by reference in its entirety.

The term "monocyclic" used herein indicates a molecular structure having one ring. The term "polycyclic" or "multicyclic" used herein indicates a molecular structure having two or more rings, including, but not limited to, fused, bridged, or spiro rings.

Terminology related to "protecting", "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups." Suitable groups for that purpose are discussed in standard textbooks in the field of chemistry, such as Greene, *Protective Groups in Organic Synthesis,* John Wiley & Sons, New York (1991), which is hereby incorporated by reference in its entirety.

The term "solvate" refers to a compound in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "method of treating" means amelioration or relief from the symptoms and/or effects associated with the disorders described herein. As used herein, reference to "treatment" of a patient is intended to include prophylaxis.

This technology also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

The term "ligand" refers to a molecule that can be used to target a desired area or tissue. The ligand will have an affinity for the desired tissue based on intrinsic properties of the ligand and the target. As used herein, a "cell-targeting ligand" targets particular desired cells within an area or tissue of an organism.

The term "linker group" refers to a chemical moiety having a chain of atoms and two or more chemical functionalities. The functional groups can be used to connect (or "link") fragments responsible for the interaction with a biological target.

The term "spacer" refers to a connecting group of a predetermined length being at least divalent. The length of the spacer in a conjugate compound described herein is chosen to achieve the maximum release profile for the therapeutic agent and will be dictated by both hydrophilicity and steric considerations.

In accordance with the present invention, the compounds of the invention include a linker group J. The linker group can include any suitable chemical moiety which can link L to X. In one embodiment, J is a saturated or unsaturated, branched or unbranched carbon chain of from 1 to about 50 atoms in length, which can be optionally substituted throughout the chain and can include from 1 to 25 heteroatoms in the chain. Suitable optional substituents include, but are not limited to, $NO_2$, CN, halogen, oxo, $C_{1-6}$ alkyl, $C_{1-6}$ haloalkyl, $C_{1-6}$ hydroxyalkyl, $C_{1-6}$ alkoxy, $C_{1-6}$ alkoxyalkyl, $C_{3-6}$ cycloalkyl, $C_{4-7}$ cycloalkylalkyl, aryl, heteroaryl, $COOR^9$, $COR^9$, $C(O)NR^9R^{10}$, $COONR^9R^{10}$, $SO_2R^9$, $SO_2NR^9R^{10}$, and $OR^9$. Suitable heteroatoms include, but are not limited to, O, S, and N. A heteroatom, if present, may be directly bonded to X or within the carbon chain.

In one embodiment, J is —Z—$Y^2$—C(O)—$Y^1$—; Z is

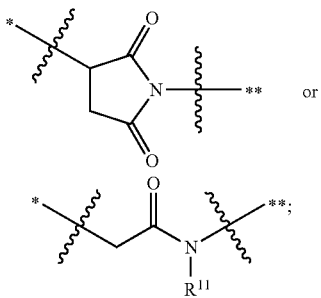

wherein the wavy lines indicate point of attachment sites and * is the point of attachment to L and ** is the point of attachment to $Y^2$;

$Y^1$ is $C_{1-6}$ alkylene or —($X^2$—$CH_2$—$CH_2$)$_l$—, each of which is optionally substituted with $R^8$;

$Y^2$ is $C_{1-6}$ alkylene or —($CH_2CH_2(X^3)$)$_q$—, each of which is optionally substituted with $R^8$;

$X^2$ is independently selected from the group consisting of:
(1) a bond;
(2) $(CH_2)_k$;
(3) O; and
(4) $NR^{12}$;

$X^3$ is independently selected from the group consisting of:
(1) a bond;
(2) $(CH_2)_k$;
(3) O; and
(4) $NR^{12}$;

$R^{11}$ is H, $C_{1-6}$ alkyl, $C_{1-6}$ hydroxyalkyl, $C_{3-6}$ cycloalkyl, $C_{4-7}$ cycloalkylalkyl, aryl, or heteroaryl, each of which is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;

$R^{12}$ is H, $C_{1-6}$ alkyl, $C_{1-6}$ haloalkyl, $C_{1-6}$ alkoxyalkyl, $C_{3-6}$ cycloalkyl, $C_{4-7}$ cycloalkylalkyl, or $C_{1-6}$ hydroxyalkyl;

k is 1 to 3;
l is 1 to 10; and
q is 1 to 10.

In a further embodiment, J is —Z—$Y^3$—, wherein Z is

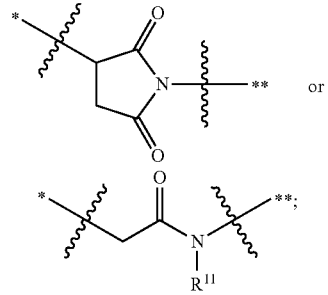

wherein the wavy lines indicate point of attachment sites and * is the point of attachment to L and ** is the point of attachment to $Y^3$;

$Y^3$ is selected from the group consisting of $C_{1-6}$ alkylene, $C_3$-$C_8$ carbocyclyl, O($CH_2$)$_r$, arylene, O($CH_2$)$_r$-arylene, -arylene-($CH_2$)$_r$—, ($CH_2$)$_r$—($C_{3-8}$ carbocyclyl), —($C_{3-8}$ carbocyclyl)-($CH_2$)$_r$, $C_{3-8}$ heterocyclyl, ($CH_2$)$_r$—($C_{3-8}$ heterocyclyl), —($C_{3-8}$ heterocyclyl)-($CH_2$)$_r$—(($X^4$)($X^5$)($CH_2$)$_r$($X^6$)($CH_2$)$_r$)$_s$, and —(($X^4$)($X^5$)($CH_2$)$_r$($X^6$)($X^7$)($CH_2$)$_r$)$_s$, — each of which is optionally substituted with $R^8$;

$X^4$, $X^5$, $X^6$, and $X^7$ are each independently selected from the group consisting of a bond, $(CH_2)_k$, O, C(O), S, $NR^{19}$, C(O)O, and C(O)$NR^{19}$;

$R^{11}$ is H, $C_{1-6}$ alkyl, $C_{1-6}$ hydroxyalkyl, $C_{3-6}$ cycloalkyl, $C_{4-7}$ cycloalkylalkyl, aryl, or heteroaryl, each of which is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;

$R^{19}$ is H, $C_{1-6}$ alkyl, $C_{1-6}$ haloalkyl, $C_{1-6}$ alkoxyalkyl, $C_{3-6}$ cycloalkyl, $C_{4-7}$ cycloalkylalkyl, or $C_{1-6}$ hydroxyalkyl;
each r is 0 to 16; and
s is 1 to 10.

In another embodiment, Q is —$(CH_2)_n$— and n is 1 to 5.

In yet another embodiment, J further comprises a thiol-containing spacer. Suitable examples of a thiol-containing spacer are described in Alley et al., "Antibody-Drug Conjugates: Targeted Drug Delivery for Cancer," *Curr Opin in Chem Biol*, 14:529-537 (2010), which is hereby incorporated by reference in its entirety.

In a further embodiment, L is a protein, a peptide, an amino acid, a receptor ligand, a hormone, or a growth factor. In particular, L can be selected from the group consisting of an antibody, an antibody fragment, scFv-Fc, minibody, diabody, scFv, folic acid, bombesin, EDG, transferrin, gastrin, gastrin-releasing peptide, platelet-derived growth factor, IL-2, IL-6, TFG-alpha, TFG-beta, VGF, insulin, and insulin-like growth factors I and II. Common methods of attachment for L utilize, for example, amines, thiols, lysines, and carboxylic acids.

The term "antibody" herein is used in the broadest sense and covers monoclonal antibodies, polyclonal antibodies, multispecfic antibodies (e.g., bispecifc antibodies), and antibody fragments which exhibit the desired biological activity. Antibodies may be murine, human, humanized, chimeric, or derived from other species.

An antibody is a protein generated by the immune system that is capable of recognizing and binding to a specific antigen (Janeway et al, "Immunobiology," 5th Ed., Garland Publishing, NY (2001), which is hereby incorporated by reference in its entirety). A target antigen generally has numerous binding sites, also called epitopes, recognized by complementary determining regions (CDR) on multiple antibodies. Each antibody that specifically binds to a different epitope has a different structure. Thus, one antigen may have more than one corresponding antibody.

The term "antibody" also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1, and IgA2), or subclass of immunoglobulin molecule. The immunoglobulin can be derived from any species. In one aspect, the immunoglobulin is of human, murine, or rabbit origin.

"Antibody fragments" comprise a portion of a full-length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR, ECD (extracellular domain), and epitope-binding fragments of any of the above which immunospecifically bind to cancer cell antigens, viral antigens, or microbial antigens; single-chain antibody molecules; and multispecific antibodies formed from antibody fragments.

In one particular embodiment, L is an antibody which binds to one or more tumor-associated antigens or cell-surface receptors selected from (1)-(35):

(1) BMPR1B (bone morphogenetic protein receptor-type IB, Genbank Accession No. NM_001203);

(2) E16 (LAT1, SLC7A5, Genbank Accession No. NM_003486);

(3) STEAP1 (six transmembrane epithelial antigen of prostate, Genbank Accession No. NM_012449);

(4) 0772P (CA125, MUC16, Genbank Accession No. AF361486);

(5) MPF (MPF, MSLN, SMR, megakaryocyte potentiating factor, mesothelin, Genbank Accession No. NM_005823);

(6) Napi3b (NAPI-3B, NPTIIb, SLC34A2, solute carrier family 34 (sodium phosphate), member 2, type II sodium-dependent phosphate transporter 3b, Genbank Accession No. NM_006424);

(7) Sema 5b (FLJ10372, KIAA1445, Mm.42015, SEMA5B, SEMAG, Semaphorin 5bHlog, sema domain, seven thrombospondin repeats (type 1 and type 1-like), transmembranedomain (TM) and short cytoplasmic domain, (semaphorin) 5B, Genbank Accession No. AB040878);

(8) PSCA hlg (2700050C12Rik, C530008O16Rik, RIKEN cDNA 2700050C12, RIKEN cDNA 2700050C12 gene, Genbank Accession No. AY358628);

(9) ETBR (Endothelin type B receptor, Genbank Accession No. AY275463);

(10) MSG783 (RNF124, hypotheticalproteinFLJ20315, Genbank Accession No. NM_017763);

(11) STEAP2 (HGNC_8639, IPCA-1, PCANAP1, STAMP1, STEAP2, STMP, prostatecancer associated gene 1, prostate cancer associated protein 1, six transmembrane epithelialantigen of prostate 2, six transmembrane prostate protein, Genbank Accession No. AF455138);

(12) TrpM4 (BR22450, FLJ20041, TRPM4, TRPM4B, transient receptor potentialcation channel, subfamily M, member 4, Genbank Accession No. NM_017636);

(13) CRIPTO (CR, CR1, CRGF, CRIPTO, TDGF1, teratocarcinoma-derived growth factor, Genbank Accession No. NP_003203 or NM_003212);

(14) CD21 (CR2 (Complement receptor 2) or C3DR (C3d/Epstein Barr virus receptor) or Hs.73792 Genbank Accession No. M26004);

(15) CD79b (CD79B, CD79β, IGb (immunoglobulin-associated beta), B29, Genbank Accession No. NM_000626);

(16) FcRH2 (IFGP4, IRTA4, SPAP1A (SH2 domain containing phosphatase anchorprotein 1a), SPAP1B, SPAP1C, Genbank Accession No. NM_030764);

(17) HER2 (Genbank Accession No. M11730);

(18) NCA (Genbank Accession No. M18728);

(19) MDP (Genbank Accession No. BC017023);

(20) IL20Rα, (Genbank Accession No. AF184971);

(21) Brevican (Genbank Accession No. AF229053);

(22) Ephb2R (Genbank Accession No. NM_004442);

(23) ASLG659 (Genbank Accession No. AX092328);

(24) PSCA (Genbank Accession No. AJ297436);

(25) GEDA (Genbank Accession No. AY260763);

(26) BAFF-R (B cell-activating factor receptor, BLyS receptor 3, BR3, Genbank Accession No. NP_443177.1);

(27) CD22 (B-cell receptor CD22-B isoform, Genbank Accession No. NP-001762.1);

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation, Genbank Accession No. NP_001774.1);

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia, Genbank Accession No. NP_001707.1);

(30) HLA-DOB (Beta subunit of MHC class II molecule (Ia antigen) that binds peptides and presents them to CD4+ T lymphocytes, Genbank Accession No. NP_002111.1);

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability, Genbank Accession No. NP_002552.2);

(32) CD72 (B-cell differentiation antigen CD72, Lyb-2, Genbank Accession No. NP_001773.1);

(33) LY64 (Lymphocyte antigen 64 (RP105), type I membrane protein of the leucine richrepeat (LRR) family, regulates B-cell activation and apoptosis, loss of function is associated with increased disease activity in patients with systemic lupus erythematosis, Genbank Accession No. NP_005573.1);

(34) FCRH1 (Fc receptor-like protein 1, a putative receptor for the immunoglobulin Fc domain that contains C2 type Ig-like and ITAM domains, may have a role in B-lymphocyte differentiation, Genbank Accession No. NP_443170.1); and

(35) IRTA2 (Immunoglobulin superfamily receptor translocation associated 2, a putative immunoreceptor with possible roles in B cell development and lymphomagenesis; deregulation of the gene by translocation occurs in some B cell malignancies, Genbank Accession No. NP_112571.1).

Other suitable antibodies are described, for example, in WO 2005/082023, which is hereby incorporated by reference in its entirety.

In a further embodiment, L is folic acid. In yet another embodiment, L is epidermal growth factor.

In one embodiment, T is a hydroxyl-containing drug moiety. The term "drug" or "therapeutic agent" as used herein means any active pharmaceutical ingredient ("API"), including its pharmaceutically acceptable salts (e.g. the hydrochloride salts, the hydrobromide salts, the hydroiodide salts, and the saccharinate salts), as well as in the anhydrous, hydrated, and solvated forms, in the form of prodrugs, and in the individually optically active enantiomers of the API as well as polymorphs of the API. Virtually any drug or therapeutic agent may be formed into the conjugate compounds described herein. In one embodiment, T is not CAS Registry No. 115834-23-6 (SF2446A1) or derivatives or analogues thereof.

In another embodiment, the drug moiety is an anticancer agent. Suitable examples of anticancer agents include, but are not limited to, N8-acetyl spermidine, actinomycin, 9-amino camptothecin, aminopterin, anguidine, anthracycline, auristatin, bleomycin, calicheamycin, camptothecin (lactone or ring-opened form of the lactone), carminomycin, CC-1065, clofaribine, 1-(2-chloroethyl)-1,2-dimethanesulfonyl hydrazide, cyclopropabenzindol-4-one (CBI), cytarabine, cytosine arabinoside, daunorubicin, dichloromethotrexate, n-(5,5-diacetoxy-pentyl) doxorubicin, 1,8-dihydroxy-bicyclo[7.3.1]trideca-4-9-diene-2,6-diyne-13-one, difluoronucleosides, doxorubicin, duocarmycin, epirubicin, esperamicin, etoposide, 5-fluorouracil, irinotecan, leurosideine, leurosine, maytansine, melphalan, 6-mercaptopurine, methopterin, methotrexate, mitomycin A, mitomycin C, morpholine-doxorubicin, butyric acid, cisplatin, diacetoxypentyldoxorubicin, maytansinol, capecitabine, leuprolide, bicalutamide, goserelin, 17-AAG, 17-DMAG, des-acetyl vinblastine, nemorubicin, podophyllotoxin and podophyllotoxin derivatives such as etoposide or etoposide phosphate, retinoic acid, saporin, tallysomycin, vinblastine, vincristine, vindesine, taxane, such as taxol or paclitaxel, taxotere or docetaxel, and taxotereretinoic acid, and isomers, salt forms, and analogues and derivatives thereof.

In one embodiment, the drug moiety is a hydroxyl-containing anticancer agent selected from the group consisting of anguidine, anthracycline, auristatin derivatives such as monomethyl auristatin E, bleomycin, calicheamycin, camptothecin (lactone or ring-opened form of the lactone), carminomycin, CC-1065, clofaribine, cytarabine, cytosine arabinoside, daunorubicin, difluoronucleosides, epirubicin, esperamicin, etoposide, 5-fluorouracil, irinotecan, leurosine, maytansine, maytansinol, capecitabine, leuprolide, bicalutamide, alpha-amanitin (or amatoxin family member), goserelin, 17-AAG, 17-DMAG, des-acetyl vinblastine, des-acetyl vinorelbine, des-acetyl vinflunine, nemorubicin, podophyllotoxin and podophyllotoxin derivatives such as etoposide, vinblastine, vincristine, vindesine, taxane, such as taxol or paclitaxel, taxotere or docetaxel, and taxotereretinoic acid, and isomers, salt forms, and analogues and derivatives thereof.

Non-limiting examples of drug moieties that may comprise T include the following: psychotherapeutic agents, such as anti-depressants (e.g., sertraline, venlafaxine, paroxetine, bupropion, citalopram, fluoxetine, mirtazapine, escitalopram, and the like), anti-schizophrenics (e.g., olanazapine, risperidone, quetiapine, aripiprazole, ziprasidone, and the like), and agents for treating attention deficit disorder (ADD) or attention deficit hyperactivity disorder (ADHD) (e.g., methylphenidate, atomoxetine, amphetamine, dextroamphetamine, and the like); anti-cholesterol drugs (e.g., atorvastatin, simvastatin, pravastatin, ezetimibe, rosuvastatin, fenofibrate fluvastatin, and the like); cardiovascular drugs (e.g., amlodipine, valsartan, losartan, hydrochlorothiazide, metoprolol, candesartan, ramipril, irbesartan, amlodipine, benazepril, nifedipine, carvedilol, enalapril, telemisartan, quinapril, doxazosin mesylate, felodipine, lisinopril, and the like); blood modifiers (e.g., epoetin alfa, darbepoetin alfa, epoetin beta, clopidogrel, pegfilgrastim, filgrastim, enoxaparin, Factor VIIA, antihemophilic factor, immune globulin, and the like); anti-infective agents, such as anti-bacterials (e.g., azithromycin, amoxicillin, clavulanic acid, levofloxacin, clarithromycin, ceftriaxone, ciprofloxacin, piperacillin, tazobactam sodium, imipenem, cilastatin, linezolid, meropenem, cefuroxime, moxifloxacin, and the like), anti-virals (e.g., lamivudine, zidovudine, valacyclovir, peginterferon, lopinavir, ritonavir, tenofovir, efavirenz, abacavir, lamivudine, zidovudine, atazanavir, and the like), and anti-fungals (e.g., terbinafine, fluconazole, itraconazole, caspofungin acetate, and the like); drugs for treating gastrointestinal disorders (e.g., esomeprazole, lansoprazole, omeprazole, antoprazole, rabeprazole, ranitidine, ondansetron, and the like); respiratory drugs (e.g., fluticasone, salmeterol, montelukast, budesonide, formoterol, fexofenadine, cetirizine, desloratadine, mometasone furoate, tiotropium, albuterol, ipratropium, palivizumab, and the like); antiarthritic drugs (e.g., celecoxib, infliximab, etanercept, rofecoxib, valdecoxib, adalimumab, meloxicam, diclofenac, fentanyl, and the like); anticancer agents (e.g., nitrogen mustard, cisplatin, doxorubicin, docetaxel, anastrozole, trastuzumab, capecitabine, letrozole, leuprolide, bicalutamide, goserelin, rituximab, oxaliplatin, bevacizumab, irinotecan, paclitaxel, carboplatin, imatinib, gemcitabine, temozolomide, gefitinib, and the like); diabetes drugs (e.g., rosiglitazone, pioglitazone, insulin, glimepiride, voglibose, and the like); anticonvulsants (e.g., gabapentin, topiramate, oxcarbazepine, carbamazepine, lamotrigine, divalproex, levetiracetam, and the like); bone metabolism regulators (e.g., alendronate, raloxifene, risedronate, zoledronic, and the like); multiple sclerosis drugs (e.g., interferon, glatiramer, copolymer-1, and the like); hormones (e.g., somatropin, norelgestromin, norethindrone, desogestrel, progestin, estrogen, octreotide, levothyroxine, testosterone, human growth hormone, and the like); urinary tract agents (e.g., tamsulosin, finasteride, tolterodine, and the like); immunosuppressants (e.g., mycophenolate mofetil, cyclosporine, tacrolimus, and the like); ophthalmic products (e.g., latanoprost, dorzolamide, botulinum, verteporfin, and the like); vaccines (e.g., pneumococcal, hepatitis, influenza, diphtheria, and the like); sedatives (e.g., Zolpidem, zaleplon, eszopiclone, and the like); Alzheimer disease therapies (e.g., donepexil, rivastigmine, tacrine, and the like); sexual dysfunction therapies (e.g., ildenafil, tadalafil, alprostadil, levothyroxine, and the like); anesthetics (e.g., sevoflurane, propofol, mepivacaine, bupivacaine, ropivacaine, lidocaine, nesacaine, etidocaine, and the like); migraine drugs (e.g., sumatriptan, almotriptan, rizatriptan, naratriptan, and the like); infertility agents (e.g., follitropin, choriogonadotropin, menotropin, follicle stimulating hormone (FSH), and the like); weight control products (e.g., orlistat, dexfenfluramine, sibutramine, and the like); and combinations of the above listed drugs. According to other embodiments, T may comprise one or more other drugs found in Physician's Desk Reference, Thomson Healthcare, 59th Bk&Cr edition (2004), which is incorporated herein by reference in its entirety.

It is also understood that chemical modifications can be made to the therapeutic agent in order to make reactions of that compound more convenient for purposes of preparing conjugates of the invention. For example, a functional group may be appended to the therapeutic agent in a location that has minimal or an acceptable effect on the activity or other properties of the therapeutic agent.

All stereoisomers of the drug moiety are contemplated for the compounds of the present invention, i.e., any combination of the R and S configurations at the chiral carbons of the drug moiety.

In a further embodiment, the conjugate compound of formula (I) has the structure:

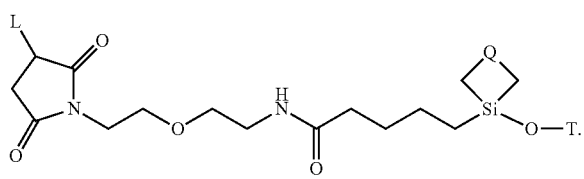

In another embodiment, the conjugate compound of formula (I) has the structure

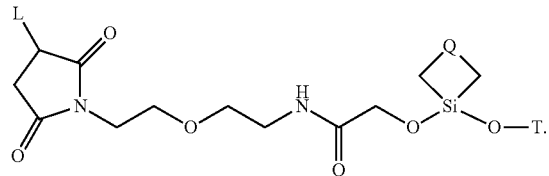

Another embodiment of the present invention relates to a compound having the formula:

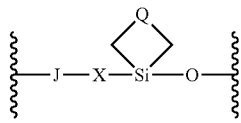
(II)

wherein the wavy lines indicate point of attachment sites and wherein:

J is a linker group;

X is independently selected from the group consisting of:

(1) a bond;

(2) O;

(3)

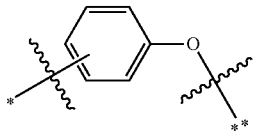

which is independently and optionally substituted from 1 to 2 times with $R^8$, wherein the wavy lines indicate point of attachment sites and * is the point of attachment to J and ** is the point of attachment to Si; and (4)

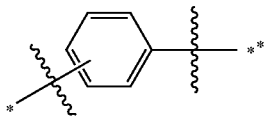

which is independently and optionally substituted from 1 to 2 times with $R^8$, wherein the wavy lines indicate point of attachment sites and * is the point of attachment to J and ** is the point of attachment to Si;

Q is $-(CH_2)_n-$, $-CH_2CHR^1CH_2-$, $-CH_2CR^5R^6CH_2-$, $-CH_2CHR^1CH_2CH_2-$, $-CH_2CH_2CHR^1CH_2CH_2-$, $-CH_2X^1CH_2-$, or $-CH_2CH_2X^1CH_2CH_2-$;

$R^1$ is $C_{1-6}$ alkyl, aryl, heteroaryl, $OR^5$, $NR^5R^6$, or $-N(COR^2)R^7$, each of which is optionally substituted with $R^8$;

$R^2$ is H, $C_{1-6}$ alkyl, $C_{3-6}$ cycloalkyl, aryl, or heteroaryl, each of which is optionally substituted with $R^8$;

$R^3$ is H, $C_{1-6}$ alkyl, $C_{3-6}$ cycloalkyl, or $-COR^4$, each of which is optionally substituted with $R^8$;

$R^4$ is H, $C_{1-6}$ alkyl, or $C_{3-6}$ cycloalkyl, each of which is optionally substituted with $R^8$;

$R^5$ is H or $C_{1-6}$ alkyl optionally substituted with $R^8$;

$R^6$ is H or $C_{1-6}$ alkyl optionally substituted with $R^8$; or $R^5$ and $R^6$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy;

$R^7$ is H, $C_{1-6}$ alkyl, $C_{3-6}$ cycloalkyl, aryl, or heteroaryl, each of which is optionally substituted with $R^8$;

$R^8$ is H, $NO_2$, CN, halogen, oxo, $C_{1-6}$ alkyl, $C_{1-6}$ haloalkyl, $C_{1-6}$ hydroxyalkyl, $C_{1-6}$ alkoxyalkyl, $C_{3-6}$ cycloalkyl, $C_{4-7}$ cycloalkylalkyl, aryl, heteroaryl, $COOR^9$, $COR^9$, $C(O)NR^9R^{10}$, $COONR^9R^{10}$, $SO_2R^9$, $SO_2NR^9R^{10}$, or $OR^9$;

$R^9$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;

$R^{10}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy; or $R^9$ and $R^{10}$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy;

$X^1$ is O, S, SO, $SO_2$, or $NR^3$; and n is 1 to 5.

Yet another embodiment of the present invention relates to a conjugate compound of formula (III):

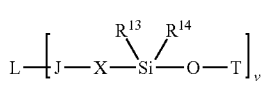
(III)

wherein

L is a cell-targeting ligand;

T is a therapeutic agent;

J is a linker group, with the proviso that when X is a bond, J cannot directly bond to the silicon atom with an O, NH, N—CH$_3$, S, or carboxyl and forms a hydrolytically stable carbon bond with the silicon atom;

X is independently selected from the group consisting of:
(1) a bond;
(2)

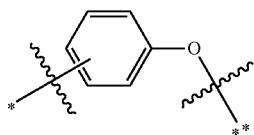

which is independently and optionally substituted from 1 to 2 times with $R^5$, wherein the wavy lines indicate point of attachment sites and * is the point of attachment to J and ** is the point of attachment to Si; and
(3)

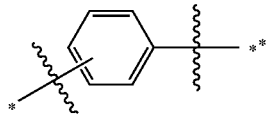

which is independently and optionally substituted from 1 to 2 times with $R^{15}$, wherein the wavy lines indicate point of attachment sites and * is the point of attachment to J and ** is the point of attachment to Si;

$R^{13}$ and $R^{14}$ are each independently selected from the group consisting of $C_{1-6}$ alkyl, $C_{3-6}$ cycloalkyl, aryl, and heteroaryl, each of which is optionally substituted with $R^{16}$;

$R^{15}$ is H, $C_{1-6}$ alkyl, $C_{1-6}$ haloalkyl, $C_{1-6}$ hydroxyalkyl, $C_{1-6}$ alkoxyalkyl, $C_{3-6}$ cycloalkyl, $C_{4-7}$ cycloalkylalkyl, CN, halogen, $NO_2$, oxo, aryl, heteroaryl, $OR^{17}$, $COOR^{17}$, $COR^{17}$, $CONR^{17}R^{18}$, $COONR^{17}R^{18}$, $SO_2R^{17}$, or $SO_2NR^{17}R^{18}$;

$R^{16}$ is H, $C_{1-6}$ alkyl, $C_{1-6}$ haloalkyl, $C_{1-6}$ alkoxyalkyl, $C_{3-6}$ cycloalkyl, $C_{4-7}$ cycloalkylalkyl, CN, halogen, $NO_2$, $OR^{17}$, $NR^{17}R^{18}$, $COOR^{17}$, $COR^{17}$, $CONR^{17}R^{18}$, $SO_2R^{17}$, $-SO_2NR^{17}R^{18}$, aryl, or heteroaryl;

$R^{17}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;

$R^{18}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy; or $R^{17}$ and $R^{18}$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy; and v is 1 to 8.

In one embodiment, X is a bond and J forms a hydrolytically stable carbon bond with the Si. As used herein, a hydrolytically stable carbon bond will not undergo hydrolysis in a cell, in particular, at low pH.

In one embodiment, $R^{13}$ and $R^{14}$ are each $C_{1-6}$ alkyl or phenyl.

In another embodiment, the conjugate compound of formula (III) has the structure:

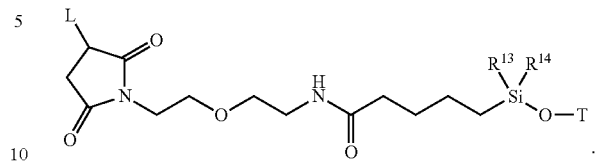

In a further embodiment, the conjugate compound of formula (III) has the structure:

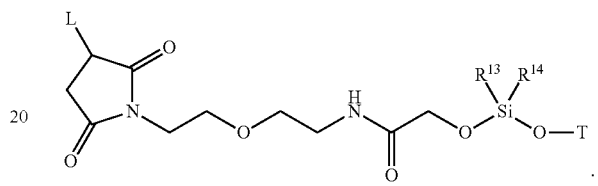

Another aspect of the present invention relates to a compound having the formula:

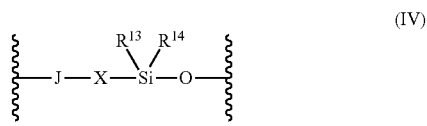

(IV)

wherein the wavy lines indicate point of attachment sites and wherein:

J is a linker group, with the proviso that when X is a bond, J cannot directly bond to the silicon atom with an O, NH, N—$CH_3$, S, or carboxyl and forms a hydrolytically stable carbon bond with the silicon atom;

X is independently selected from the group consisting of:
(1) a bond;
(2)

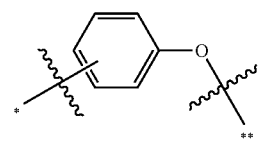

which is independently and optionally substituted from 1 to 2 times with $R^{15}$, wherein the wavy lines indicate point of attachment sites and * is the point of attachment to J and ** is the point of attachment to Si; and
(3)

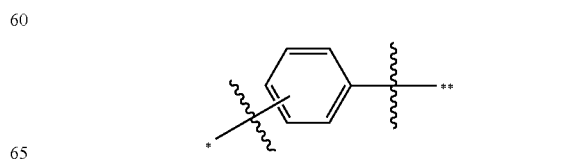

which is independently and optionally substituted from 1 to 2 times with $R^{15}$, wherein the wavy lines indicate point of attachment sites and * is the point of attachment to J and ** is the point of attachment to Si;

$R^{13}$ and $R^{14}$ are each independently selected from the group consisting of $C_{1-6}$ alkyl, $C_{3-6}$ cycloalkyl, aryl, and heteroaryl, each of which is optionally substituted with $R^{16}$;

$R^{15}$ is H, $C_{1-6}$ alkyl, $C_{1-6}$ haloalkyl, $C_{1-6}$ hydroxyalkyl, $C_{1-6}$ alkoxyalkyl, $C_{3-6}$ cycloalkyl, $C_{4-7}$ cycloalkylalkyl, CN, halogen, $NO_2$, oxo, aryl, heteroaryl, $OR^{17}$, $COOR^{17}$, $COR^{17}$, $CONR^{17}R^{18}$, $COONR^{17}R^{18}$, $SO_2R^{17}$, or $SO_2NR^{17}R^{18}$;

$R^{16}$ is H, $C_{1-6}$ alkyl, $C_{1-6}$ haloalkyl, $C_{1-6}$ alkoxyalkyl, $C_{3-6}$ cycloalkyl, $C_{4-7}$ cycloalkylalkyl, CN, halogen, $NO_2$, $OR^{17}$, $NR^{17}R^{18}$, $COOR^{17}$, $COR^{17}$, $CONR^{17}R^{18}$, $SO_2R^{17}$, —$SO_2NR^{17}R^{18}$, aryl, or heteroaryl;

$R^{17}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;

$R^{18}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy; or $R^{17}$ and $R^{18}$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy.

Within these embodiments, the selection of a particular preferred substituent at any one of $R^1$-$R^{19}$, L, T, J, X, $X^1$-$X^7$, Q, Z, $Y^1$, $Y^2$, and $Y^3$ does not affect the selection of a substituent at any of the others of $R^1$-$R^{19}$, L, T, J, X, $X^1$-$X^7$, Q, Z, $Y^1$, $Y^2$, and $Y^3$. That is, preferred compounds provided herein have any of the preferred substituents at any of the positions.

One embodiment relates to pharmaceutically acceptable salts, or non-salt forms, of any of the compounds of formulae (I)-(IV) described herein. In one embodiment, the salt is a HCl salt.

The compounds of the invention are stable under defined conditions but are degradable under specified conditions, such as, for example, physiological temperature (e.g., about 37° C.) or acidic conditions. In one embodiment, the compound is stable extracellularly; however, upon entry into a cell degrades to thereby effect release of the therapeutic agent in its underivatized or pharmacologically active form. Thus, the conjugate compound or pharmaceutical composition thereof provides for delivery and release of the therapeutic agent through degradation of the conjugate compound. The terms "degradable" and "labile" merely are used to describe the nature of the compounds, in that the inventive compounds are stable under one or more defined conditions but, under one or more different specified conditions, the compounds will undergo a chemical transformation (e.g. cleavage). This transformation may be exemplified by the breaking of one or more bonds within the compound that causes the compound to become fragmented. The transformation also may be exemplified by the partial or complete solubilization of the compound under the specified conditions. Accordingly, the terms "degradable" or "labile" may mean the compounds are subject to being transformed by a variety of ways, and a skilled person viewing the present description would be able to envision a variety of methods whereby the inventive compounds could be degraded according to the various uses described herein, and all of such methods are encompassed by the present invention. In various embodiments, the degradation may be dependant upon one or more of the following conditions: enzymatic cleavage; pH; radiation; ionic strength; oxidation; reduction; temperature; an alternating magnetic field; an alternating electric field; combinations thereof; or the like.

In one embodiment, the compounds of the invention may be described as "pH labile compounds" or "acid labile compounds." A pH labile compound is understood to mean a compound that may be chemically transformed (as described above) in relation to a change in pH. Accordingly, a pH labile compound may be predominantly stable at a pH below a certain value but degrade when pH is raised above the certain value. Likewise, a pH labile compound may be predominantly stable at a pH above a certain value but degrade when pH is lowered below the certain value. In a specific embodiment, an acid labile compound is predominantly stable above a pH of 7.9, 7.8, 7.7, 7.6, 7.5, 7.4, 7.3, 7.2, 7.1, or 7.0 but degrades below the specified value. In other embodiments, an acid labile compound can comprise a compound that is predominantly stable at a pH above about 7.5, above about 7, or above about 6.5 but degrades below this value.

In specific embodiments, a pH labile compound according to the invention may be described as being degradable at cellular pH conditions. For example, in some embodiments, the compounds of the invention (and compositions incorporating the compounds) particularly may be designed to degrade under pH conditions typically found in cell endosomes or lysosomes.

In accordance with the present invention, the ligand in the conjugate compound may be linked to J via a carbon, amide, amine, or thioether bond. The therapeutic agent is connected to oxygen of the conjugate compound via a chemically reactive functional group pending from the therapeutic agent.

This technology also includes compounds of formulae (I)-(IV), wherein one or more of the atoms, e.g., C or H, are replaced by the corresponding radioactive isotopes of that atom (e.g., C replaced by $^{14}C$ and H replaced by $^{3}H$), or a stable isotope of that atom (e.g., C replaced by $^{13}C$ or H replaced by $^{2}H$). Radioisotopes of hydrogen, carbon, phosphorous, fluorine, iodine and chlorine include $^{3}H$, $^{14}C$, $^{35}S$, $^{18}F$, $^{32}P$, $^{33}P$, $^{125}I$, and $^{36}Cl$, respectively. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent. Such compounds have a variety of potential uses, e.g., as standards and reagents in determining the ability of a potential pharmaceutical to bind to particular proteins. In addition, in the case of stable isotopes, such compounds may have the potential to favorably modify the biological properties, e.g., pharmacological and/or pharmacokinetic properties, of compounds of formula (I)-(IV). The details concerning selection of suitable sites for incorporating radioactive isotopes into the compounds are known to those skilled in the art.

Another embodiment relates to a pharmaceutical composition containing a therapeutically effective amount of the compound of formula (I)-(IV) and a pharmaceutically acceptable carrier.

Another aspect of this technology relates to a method of treating cancer. The method involves administering to a patient in need of such treatment a therapeutically effective amount of a compound of formula (I) or (III), or a pharmaceutically acceptable salt thereof.

In one embodiment, the patient is a mammal. As used herein the term "mammal" refers to humans as well as all other mammalian animals. As further used herein, the term "mammal" includes a "subject" or "patient" and refers to a warm blooded animal. In a further embodiment, the patient is a non-human mammal.

As used herein, the terms "cancer" and "cancerous" refer to or describe the physiological condition in mammals that is typically characterized by unregulated cell growth. Examples of cancer include, but are not limited to, melanoma, carcinoma, lymphoma, blastoma, sarcoma, and leukemia or lymphoid malignancies. More particular examples of cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

In one embodiment, the method relates to the treatment of 5T4-positive cancer. Suitable cell-targeting ligands and therapeutic agents for use in a conjugate described herein for the treatment of 5T4-positive cancer are described, for example, in WO 2012/131527, which is hereby incorporated by reference in its entirety.

As used herein, the term "therapeutically effective" and "effective amount," is defined as the amount of the pharmaceutical composition that produces at least some effect in treating a disease or a condition. For example, an effective amount is the amount required to inhibit the growth of cells of a neoplasm in vivo. The effective amount of active compound(s) used to practice the present invention for therapeutic treatment of neoplasms (e.g., cancer) varies depending upon the manner of administration, the age, body weight, and general health of the subject. It is within the skill in the art for an attending physician or veterinarian to determine the appropriate amount and dosage regimen. Such amounts may be referred to as "effective" amounts.

A "drug moiety" in reference to a conjugate of the invention, refers to the portion or residue of the unmodified parent active agent up to the covalent linkage resulting from covalent attachment of the drug (or an activated or chemically modified form thereof) to the remainder of the conjugate compound of the invention. Upon hydrolysis of the linkage between the drug moiety and the remainder of the conjugate compound, the active agent per se is released.

In another embodiment, the conjugate compounds of formula (I) or (III) of present invention can be administered to a patient in need of treatment for any disorder treatable with the therapeutic agents described above. Such disorders include, but are not limited to, inflammatory disorders, depressive disorders, allergies, anemia, autoimmune diseases, back and neck injuries, birth defects, blood disorders, bone diseases, cancers, circulation diseases, dental conditions, diabetes, digestions and nutrition disorders, dissociative disorders, ear conditions, eating disorders, eye conditions, foodborne illnesses, gastrointestinal diseases, genetic disorders, heart diseases, heat and sun related conditions, hormonal disorders, impulse control disorders, infectious diseases, insect bites and stings, epilepsy, gout, hypertension, malaria, migraines, erectile dysfunction, anxiety disorders, kidney diseases, leukodystrophies, liver diseases, mental health disorders, metabolic diseases, mood disorders, neurological disorders, personality disorders, phobias, pregnancy complications, prion diseases, prostate diseases, respiratory diseases, sexual disorders, sexually transmitted diseases, skin conditions, sleep disorders, speech-language disorders, sports injuries, thyroid diseases, tropical diseases, vestibular disorders, waterborne illnesses, and other diseases.

A combination drug or fixed-dose combination (FDC) is a formulation of two or more active ingredients combined in a single dosage form, available in certain fixed doses. Fixed-dose combination drug products may improve medication compliance by reducing the pill burden of patients, as well as any usual advantages of combination therapy.

Multiple drug moieties as described herein can be co-delivered using the conjugate compounds of the present invention, for example, when m or v is greater than one, or by administering more than one conjugate compound. For example, delivery of a chemotherapeutic that induces DNA damage, such as cisplatin along with a DNA repair-blocking drug such as a cdk-inhibitor therapy can improve the efficacy of the chemotherapeutic. In another example, the co-delivery of anti-nausea or pain medication with a chemotherapeutic could provide benefits as the release of these drugs can be individually tuned to release at the same time or at staggered times.

According to some embodiments of the present invention, the drug concentration available at a target biologic system or location is increased through use of the conjugates of the present invention. According to such embodiments, the present invention provides a system for controlled delivery.

Another aspect of the present invention relates to a process for preparation of a product compound of formula (I) or (II) which includes treating a first intermediate compound of formula V:

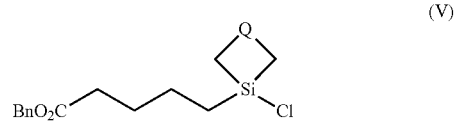

(V)

under conditions effective to form the product compound of formula (I) or (II).

In one embodiment, the first intermediate (V) is reacted with a therapeutic agent (T) having a hydroxyl group, a linker group (J), and cell-targeting ligand (L) under conditions effective to form the product compound of formula (I).

Yet another aspect of the present invention relates to a process for preparation of a product compound of formula (III) or (IV) which includes treating a first intermediate compound of formula VI:

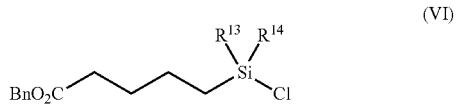

(VI)

under conditions effective to form the product compound of formula (III) or (IV).

In one embodiment, the first intermediate (VI) is reacted with a therapeutic agent (T) having a hydroxyl group, a linker group (J), and cell-targeting ligand (L) under conditions effective to form the product compound of formula (I).

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Compounds according to the invention, for example, starting materials, intermediates, or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example, those described by Larock, *Comprehensive Organic Transformations*, 2$^{nd}$ Edition, Wiley-VCH publishers, New York (1999), which is hereby incorporated by reference in its entirety.

The reagents and reaction conditions described in this invention by no means limit alternative reagents and reaction conditions such as temperature, concentrations and choices of solvents. One skilled in the art may use alternative reagents and alternation reaction conditions taught by the literature, for example, those described by Larock, *Comprehensive Organic Transformations*, 2$^{nd}$ Edition, Wiley-VCH publishers, New York (1999) to achieve the chemical transformations needed for compounds in this invention.

A compound of formula (I)-(IV) including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxy, amino, imino, thio, carboxy or other groups, where these are desired in the final product, to avoid their unwanted participation in the reactions. Conventional protecting groups may be used in accordance with standard practice (e.g., Wuts et al., *Protective Groups in Organic Chemistry* (4$^{th}$ Edition), Wiley (2006) and McOmie, *Protective Groups in Organic Chemistry*, Plenum Press (1973), which are hereby incorporated by reference in their entirety).

Removal of Ns protecting group in compounds below may be achieved by treatment with thiophenol and base, such as potassium carbonate.

Compounds described below where a substituent is hydrogen may be diversified to other compounds where the substituent is alkyl, etc. via alkylation, reductive amination or other methods.

Compounds may be obtained in enantiomerically pure (R) and (S) form by crystallization with chiral salts as well known to one skilled in the art, or alternatively, may be isolated though chiral HPLC employing commercially available chiral column.

Compounds of formula (I)-(IV) may be converted to their salt form.

The intermediate (V) can be prepared by the general schemes outlined below (Schemes 1 and 2).

Scheme 1

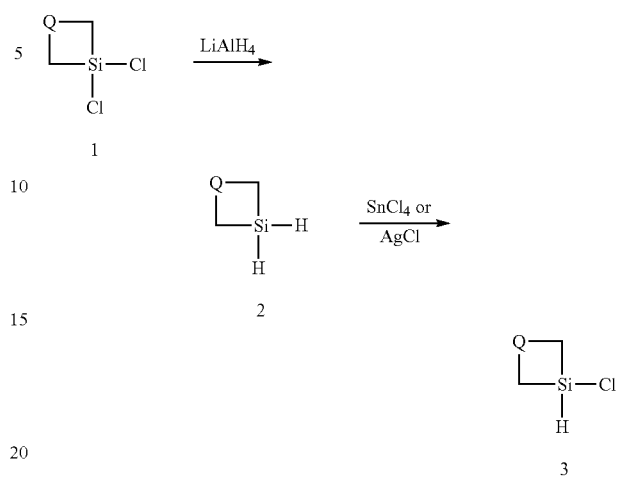

Dichlorosiletane intermediate 1 is converted to siletane intermediate 2 with a reducing agent, such as LiAlH$_4$. Siletane intermediate 2 can then be converted to the intermediate 3 using either SnCl$_4$ according to the technique disclosed in Doklady, *Akademii Nauk SSSR*, 198(1):112-114 (1971), which is hereby incorporated by reference in its entirety, or using AgCl according to the technique disclosed in Harthcock et al., *J. Phys. Chem.*, 86(22):4335-4342 (1982), which is hereby incorporated by reference in its entirety.

Intermediate 3 can then be treated using Karstedt's catalyst (Pt$^0$) at 60° C. to give chlorosilane intermediate (V), as shown below in Scheme 2:

Scheme 2

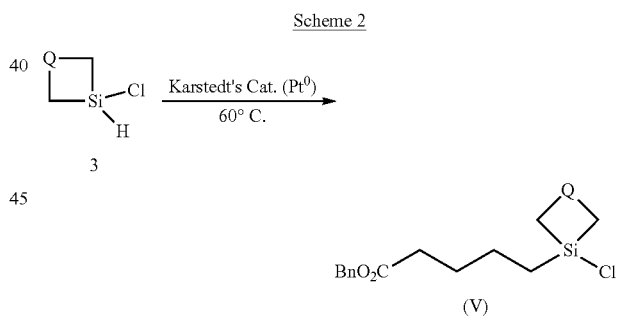

Alternatively, the intermediate (V) can be prepared by the general scheme outlined below (Scheme 3):

Scheme 3

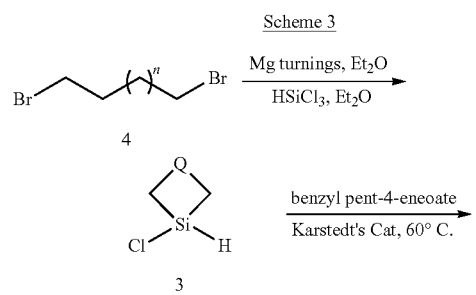

-continued (V)

Compound 4 is commercially available from Sigma-Aldrich Co. LLC, St. Louis, Mo. (n=1, catalog #140805; n=2, catalog #128007). Compound 3 can be achieved by a method reported by West, *J. Am. Chem. Soc.*, 76:6012 (1954), which is hereby incorporated by reference in its entirety. The general procedure for hydrosilylation includes the following: to a mixture of benzyl pent-4-enoate (1 eq.) and cyclic silyl chloride B is added Karstedt's catalyst (CAS Number: 68478-92-2) solution (in xylenes; ~2% Pt). The reaction vessel is sealed and the mixture heated to 60° C. The crude liquid is used without purification.

The intermediate (VI) can be prepared by the general scheme outlined below (Scheme 4).

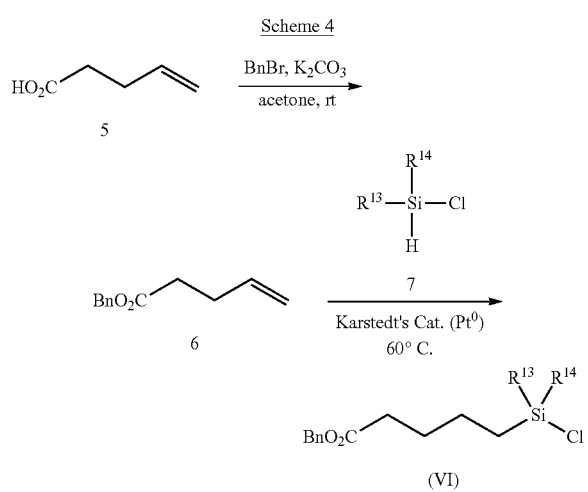

Treatment of pent-4-enoic acid 5 with (bromomethyl)benzene and potassium carbonate in the presence of acetone at room temperature gives intermediate 6. Intermediate 6 is then reacted with 7 in the presence of Karstedt's catalyst (Pt⁰) at 60° C. to give chlorosilane intermediate (VI). Compound 7, where $R_{13}$ =$R_{14}$ =$CH_3$ or $R_{13}$ =$R_{14}$=Ph or $R_{13}$=Ph, $R_{14}$ =$CH_3$ are commercially available from Sigma-Aldrich Co. LLC, St. Louis, Mo. ($R_{13}$ =$R_{14}$ =$CH_3$, catalog #144207; $R_{13}$ =$R_{14}$=Ph, catalog #673935; $R_{13}$=Ph, $R_{14}$ =$CH_3$, catalog #68645). Intermediate (VI) can be achieved following the hydrosilylation procedure described above with regard to Scheme 3.

Silyl chloride V or VI can be coupled with an alcohol group as described in Scheme 6 or first converted to a silanol using aqueous acid or base. The resulting silanol can then be subsequently activated by any of a variety of literature methods to provide a silicon reagent capable of further reaction with an alcohol group to provide a silyl ether product. Silyl triflates, silyl trichloroacetimidates, silyl cyanides are examples of such activated silyl reagents known to be effective for preparing silyl ethers. Greene et al, PGM Protective Groups in Organic Synthesis 3$^{rd}$Edition (1999) and references therein describe silicon reagents and methods useful for making silyl ethers and is incorporated by reference in its entirety.

Intermediate (VII) can be prepared by the general scheme outlined below (Scheme 5):

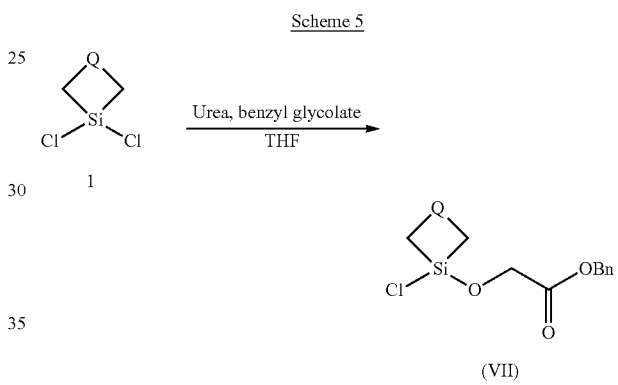

Intermediate (VII) is commercially available from Gelest, Inc., Morrisville, Pa. (n=1, catalog #SIC2524.0; n=2, catalog #SIC2564.0). Or, as in Scheme 5, to an ice-cold solution of dichlorosilane 1 in THF is added urea and benzyl glycolate. After stirring at room temperature for 1-4 hours, the mixture is concentrated and then diluted with chloroform. Drying agent is added and the mixture filtered and the filtrate concentrated under reduced pressure.

Compounds of formula (I) can be prepared by the general scheme outlined below (Scheme 6).

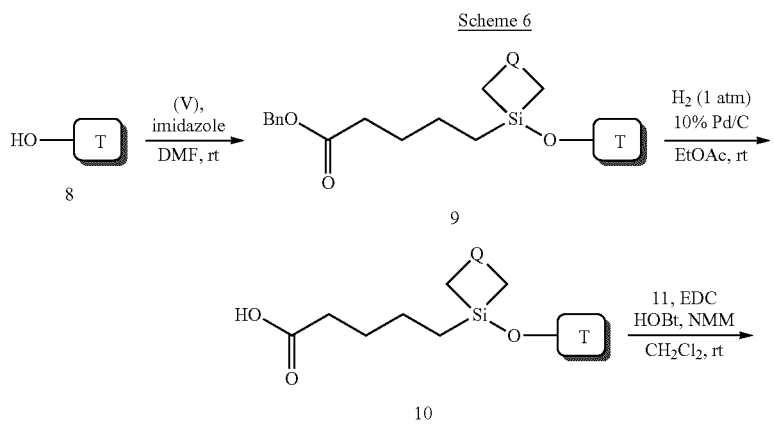

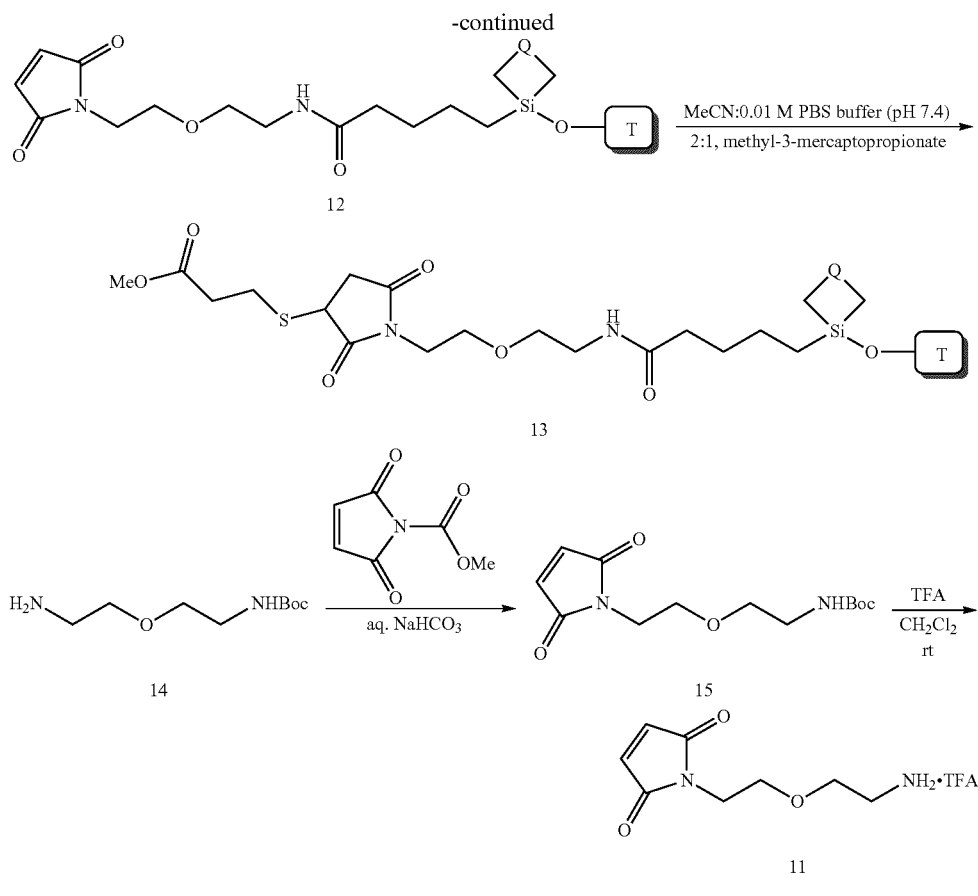

In accordance with Scheme 6, therapeutic agent T having a hydroxyl group 8 can be reacted with intermediate (V) and imidazole in solvent (dimethylformamide) at room temperature to produce intermediate 9. One example of a therapeutic agent T is 4-desacetylvinblastine which can be achieved by a method reported in PCT Publication No. WO 2008/120098, which is hereby incorporated by reference in its entirety. As shown in Scheme 6, to a mixture of therapeutic agent T and imidazole in DMF was added crude silyl chloride intermediate (V) or (VI). Following an aqueous workup, the material can be purified either by silica gel or C18 chromatography. The product structure is verified by mass analysis and $^1$H NMR. Intermediate 9 is then subject to hydrogenation in the presence of a catalyst (10% Pd/C) to produce intermediate 10. In particular, to a solution of intermediate 9 in ethyl acetate is added palladium on carbon. The reaction mixture is stirred approximately 1-5 hours under an atmosphere of hydrogen prior to being filtered and concentrated. The crude residue is used without further purification. Intermediate 10 is reacted with intermediate 11 to produce intermediate 12, which corresponds to formula (I) where X is a bond, J is —Z—Y$^2$—C(O)—Y$^1$—, Z is

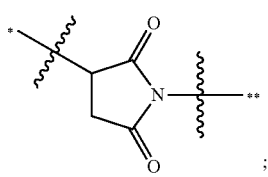 [SMILES: *C1CC(=O)N(*)C1=O]

;

wherein the wavy lines indicate point of attachment sites and * is the point of attachment to L and ** is the point of attachment to Y$^2$; Y$^1$ is C$_{1-6}$ alkylene, Y$^2$ is —(CH$_2$CH$_2$(X$^3$))$_2$—, and X$^3$ is independently O and NR$^{12}$, where R$^{12}$ is H. In particular, for coupling of the amine salt, to prepare the amide bond, acid 10 is combined with an excess of base (N-methyl morpholine), EDCI and the TFA salt of 1-(2-(2-aminoethoxy)ethyl)-1H-pyrrole-2,5-dione (11) in methylene chloride. The TFA salt of 1-(2-(2-aminoethoxy)ethyl)-1H-pyrrole-2,5-dione can be achieved by a method reported by Weber et al., *Bioconjugate Chem.*, 1:431 (1990), which is hereby incorporated by reference in its entirety, and as described in Scheme 6. Alternatively, activated esters of acid 10 can be prepared and then reacted with an amine in a suitable solvent (e.g. DMF, CH$_2$Cl$_2$). Treatment of acid 10 with EDCI, catalytic DMAP and base (e.g. DIPEA) and suitable ROH moiety (e.g. pentafluorophenol, N-hydroxysuccinimide, or p-nitrophenol) provides the activated ester. In order to produce compounds of formula (I), the malemide moiety of intermediate 12 is reacted with the desired cell-targeting ligand L. To trap the maleimide and produce 13, to a mixture of 12 in acetonitrile:0.01M PBS buffer (2:1) is added an excess of methyl-3-mercaptopropionate. After stirring for 10 minutes the reaction mixture is concentrated and subjected to an aqueous workup. The resulting crude residue is purified by C18 chromatography. The product structure is verified by mass analysis and $^1$H NMR.

Compounds of formula (III) can be prepared by the general scheme outlined below (Scheme 7) and as described in detail with regard to Scheme 6.

Scheme 7

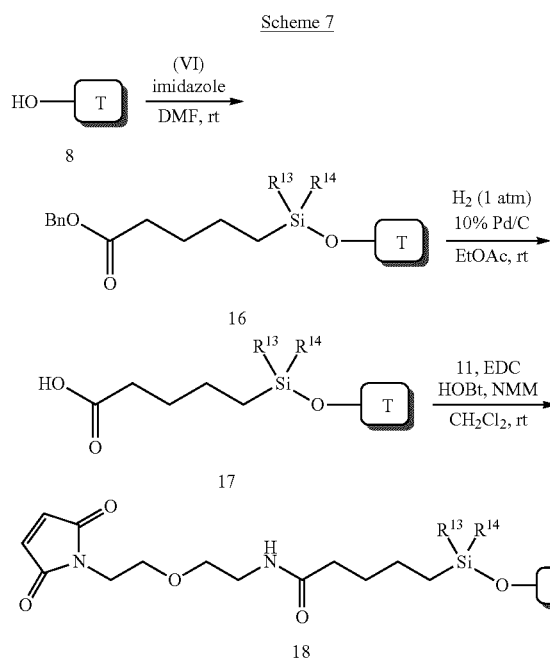

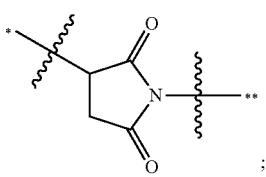 [SMILES: *C1CC(=O)N(*)C1=O]

In accordance with Scheme 7, therapeutic agent T having a hydroxyl group (8) can be reacted with intermediate (VI) and imidazole in solvent (dimethylformamide) at room temperature to produce intermediate 16. Intermediate 16 is then subjected to hydrogenation in the presence of a catalyst (10% Pd/C) to produce intermediate 17. Intermediate 17 is reacted with intermediate 11 to produce intermediate 18, which corresponds to formula (III) where X is a bond, J is —Z—Y²—C(O)—Y¹—, Z is wherein the wavy lines indicate point of attachment sites and * is the point of attachment to L and ** is the point of attachment to $Y^2$; $Y^1$ is $C_{1-6}$ alkylene, $Y^2$ is —($CH_2CH_2$($X^3$))$_2$—, and $X^3$ is independently O and $NR^{12}$, where $R^{12}$ is H. In order to produce compounds of formula (III), the maleimide moiety of intermediate 18 is reacted with the desired cell-targeting ligand L.

As shown in Scheme 8 below:

Scheme 8

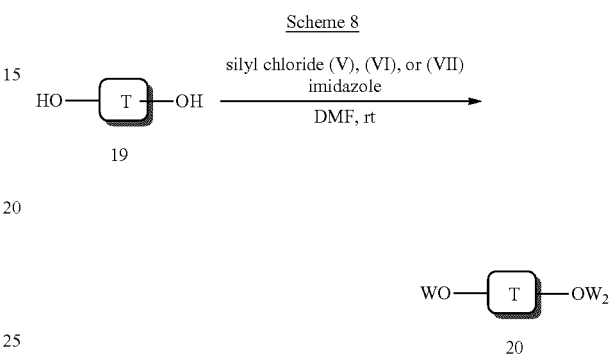

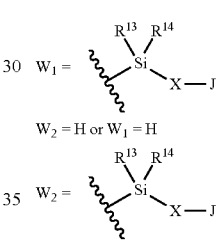

for O-silylation, to a mixture of 19 and imidazole in DMF is added silyl chloride (V), (VI), or (VII). Following either concentration or an aqueous workup, the material is purified either by silica gel or C18 chromatography. The product structure is verified by mass analysis and $^1H$ NMR. An example of O-silylation in accordance with Scheme 8 is shown in Scheme 9 below:

Scheme 9

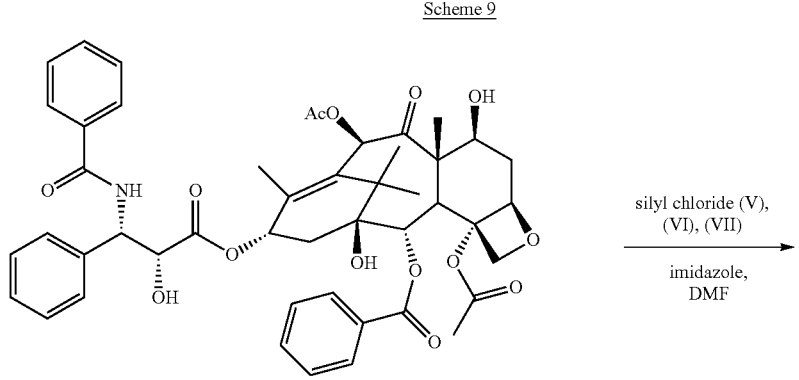

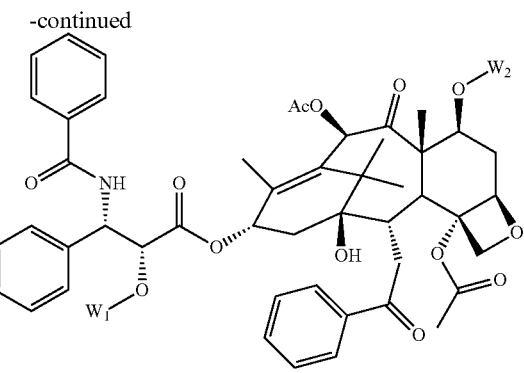
20
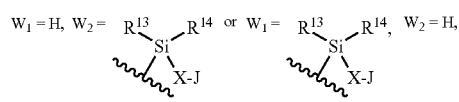
Although Schemes 8 and 9 show W based on intermediate VI (for brevity), intermediates V or VII could also be used.
An example of a scheme for making a compound of formula (III) is shown in Scheme 10 below:
Scheme 10
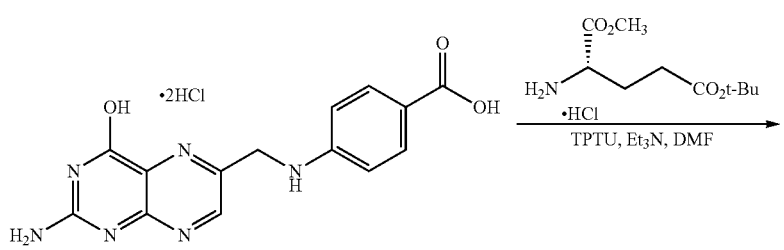
21
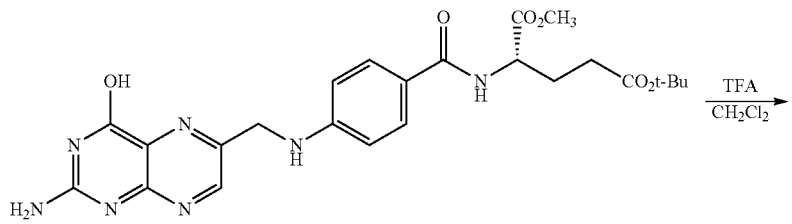
22
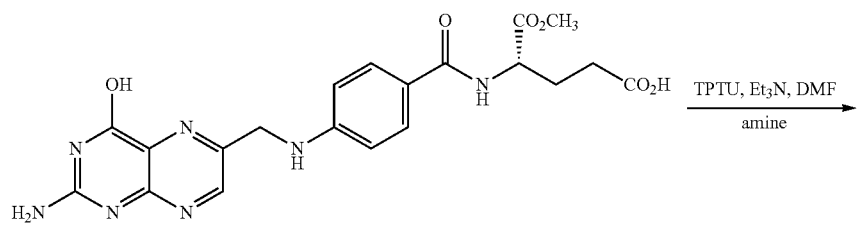
23

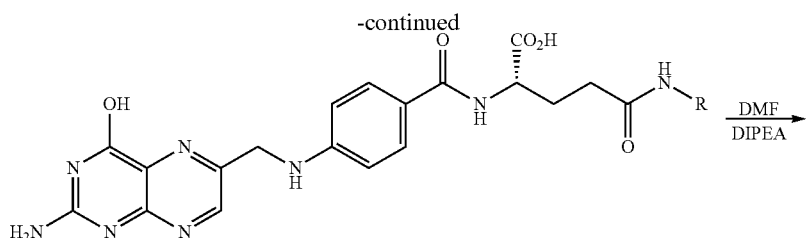

24

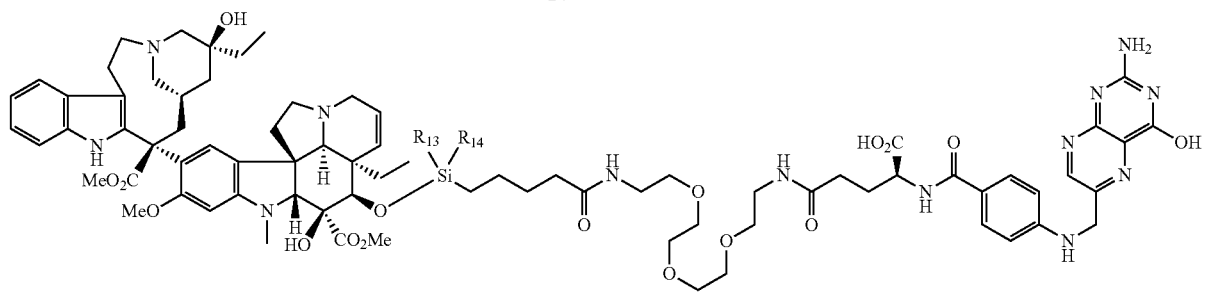

25

25

Carboxylic acid 21 can be activated with a coupling agent for amide synthesis (e.g. 2-(2-pyridon-1-yl)-1,1,3,3-tetramethyluronium tetrafluoroborate: TPTU) and treated (S)-5-tert-butyl 1-methyl 2-aminopentanedioate hydrochloride with a base as needed (e.g. triethylamine) in a solvent (DMF) at room temperature. Following an aqueous workup, the material is purified either by silica gel or C18 chromotography. The product structure is verified by mass analysis and $^1$H NMR. Ester 22 can be deprotected by treatment with acid (trifluoroacetic acid) in a solvent ($CH_2Cl_2$) at room temperature. Following an aqueous workup, the material is purified either by silica gel or C18 chromotography. The product structure is verified by mass analysis and $^1$H NMR. Carboxylic acid 23 can be activated with a coupling agent for amide synthesis (e.g. 2-(2-pyridon-1-yl)-1,1,3,3-tetramethyluronium tetrafluoroborate) and treated with a mono-protected diamine (e.g. tert-butyl (2-(2-(2-aminoethoxy)ethoxy)ethyl) carbamate) with a base as needed ($Et_3N$) in a solvent (DMF) at room temperature. The amine protecting group is then cleaved with acid (e.g. aq. HCl). Using the method described with regard to Scheme 6 for coupling of the amine salt, activated esters of acid 10 or 17 (Scheme 10 shows an activated ester of acid 17) can be coupled with amine 24 in a solvent (e.g. DMF) and base (e.g. DIPEA) to provide the product 25.

It will be appreciated that compounds according to the present invention may contain asymmetric centers. These asymmetric centers may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of formula (I)-(IV) herein above. Such isomers can be separated from their mixtures, by the application or adaptation of known methods, for example chromatographic techniques and recrystallization techniques, or they are separately prepared from the appropriate isomers of their intermediates.

Radiolabelled compounds of the invention are synthesized by a number of techniques well known to those of ordinary skill in the art, e.g., by using starting materials incorporating therein one or more radioisotopes. Compounds of the present invention where a stable radioisotope, such as carbon-14, tritium, iodine-121, or another radioisotope, has been introduced synthetically are useful diagnostic agents.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining two or more active ingredients useful in treating the disease. A kit may provide (alone or in combination with a pharmaceutically acceptable diluent or carrier) the compounds of formula (I)-(IV) and an additional active ingredient.

In practice, the compounds of the present invention may generally be administered parenterally, intravenously, subcutaneously, intramuscularly, colonically, nasally, intraperitoneally, rectally, or orally.

The products according to the present invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate, and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol, and chloroform or mixtures thereof may also be used.

For parenteral administration, emulsions, suspensions, or solutions of the products according to the invention in vegetable oil, for example sesame oil, groundnut oil, or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride, and that they are sterilized by heating, irradiation, or microfiltration.

Suitable compositions containing the compounds of the present invention may be prepared by conventional means. For example, compounds of the present invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula (I)-(IV).

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.5 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health, and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

EXAMPLES

The following examples are provided to illustrate embodiments of the present invention but are by no means intended to limit its scope. The present invention is not limited to the compounds found in the examples, and many other compounds falling within the scope of the invention may also be prepared using the procedures set forth in the above synthetic schemes. The preparation of additional compounds of the present invention using these methods will be apparent to one of ordinary skill in the chemical arts

Example 1

General Procedures

Unless otherwise noted, reagents and solvents were used as received from commercial suppliers. Proton nuclear magnetic resonance (NMR) spectra were obtained on Bruker spectrometers at 300 or 500 MHz. Spectra are given in ppm ($\delta$) and coupling constants, J, are reported in Hertz. Tetramethylsilane (TMS) was used as an internal standard. Mass spectra were collected using a Waters SQ Detector single quadripole mass spectrometer (ESI). High performance liquid chromatograph (HPLC) analyses were obtained using a Luna C18(2) column (250×4.6 mm, Phenomenex, Torrance, Calif.) with UV detection at 254 nm using the standard solvent gradient programs Method A or Method B:

| Method A: | | | |
|---|---|---|---|
| Time (min) | Flow (mL/min) | % A | % B |
| 0.0 | 1.0 | 90.0 | 10.0 |
| 20.0 | 1.0 | 0.0 | 100.0 |
| 25.0 | 1.0 | 0.0 | 100.0 |
| 27.0 | 1.0 | 90.0 | 10.0 |
| 32.0 | 1.0 | 90.0 | 10.0 |

A = Water with 0.1% Trifluoroacetic Acid
B = Acetonitrile with 0.1% Trifluoroacetic Acid

| Method B: | | | |
|---|---|---|---|
| Time (min) | Flow (mL/min) | % A | % B |
| 0.0 | 8 | 80.0 | 20.0 |
| 10.0 | 1.0 | 0.0 | 100.0 |

-continued

Method B:

| Time (min) | Flow (mL/min) | % A | % B |
| --- | --- | --- | --- |
| 12.0 | 1.0 | 0.0 | 100.0 |
| 14.0 | 1.0 | 80.0 | 20.0 |
| 16.0 | 1.0 | 80.0 | 20.0 |

A = Water with 0.1% Trifluoroacetic Acid
B = Acetonitrile with 0.1% Trifluoroacetic Acid Example 2

Preparation of benzyl 5-(chlorodimethylsilyl)pentanoate

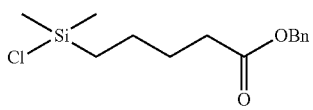 [SMILES: C[Si](C)(Cl)CCCCC(=O)OCc1ccccc1]

To a mixture of chlorodimethylsilane (0.730 g; 6.57 mmol) and benzyl pent-4-enoate (1.25 g; 6.57 mmol) under argon was added one drop of Karstedt's catalyst solution (in xylenes; ~2% Pt). The reaction vessel was sealed and the mixture was heated to 60° C. for 13.5 hours. The crude liquid was used without purification.

Example 3

Preparation of benzyl 5-(chlorodiphenylsilyl)pentanoate

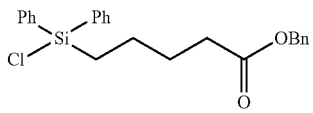 [SMILES: O=C(CCCC[Si](Cl)(c1ccccc1)c1ccccc1)OCc1ccccc1]

To a mixture of chlorodiphenylsilane (0.49 g; 2.58 mmol) and benzyl pent-4-enoate (0.50 g; 2.58 mmol) under argon was added two drops of Karstedt's catalyst solution (in xylenes; ~2% Pt). The reaction vessel was sealed and the mixture was heated to 60° C. for 15 hours. The crude liquid was used without purification.

Example 4

Preparation of benzyl 5-(1-chlorosilinan-1-yl)pentanoate

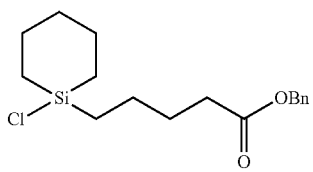 [SMILES: O=C(CCCC[Si]1(Cl)CCCCC1)OCc1ccccc1]

To a mixture of crude 1-chlorosilinane (0.35 g) and benzyl pent-4-enoate (0.50 g; 2.63 mmol) under argon was added two drops of Karstedt's catalyst solution (in xylenes; ~2% Pt). The reaction vessel was sealed and the mixture was heated to 60° C. for 16 hours. The crude liquid was used without purification.

Example 5

Preparation of benzyl 5-(1-chlorosilolan-1-yl)pentanoate

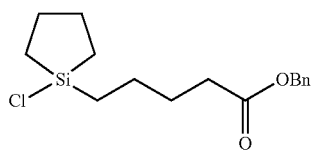 [SMILES: O=C(CCCC[Si]1(Cl)CCCC1)OCc1ccccc1]

To a mixture of crude 1-chlorosilolane (0.317 g) and benzyl pent-4-enoate (0.50 g; 2.63 mmol) under argon was added two drops of Karstedt's catalyst solution (in xylenes; ~2% Pt). The reaction vessel was sealed and the mixture was heated to 60° C. for 18 hours. The crude liquid was used without purification.

Example 6

Preparation of benzyl 2-((1-chlorosilinan-1-yl)oxy)acetate

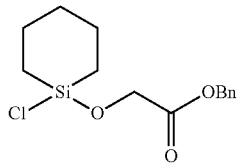 [SMILES: O=C(CO[Si]1(Cl)CCCCC1)OCc1ccccc1]

To a solution of cyclopentamethylenedichlorosilane (0.5 mL; 3.42 mmol) in dry THF (10 mL) was added urea (0.246 g; 4.10 mmol). The mixture was then cooled to 0° C. and benzyl glycolate (0.48 mL; 3.42 mmol) was added dropwise over a 15 minute span. The mixture was then taken off the ice bath and allowed to stir at room temperature for 40 minutes. The mixture was then concentrated under high vacuum and diluted with chloroform. The aqueous layer was soaked up with excess $Na_2SO_4$ and the mixture was filtered. The filtrate was concentrated to a light yellow crude liquid which was used without further purification.

Example 7

Preparation of benzyl 2-((1-chlorosilolan-1-yl)oxy)acetate

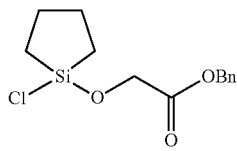 [SMILES: O=C(CO[Si]1(Cl)CCCC1)OCc1ccccc1]

To a solution of cyclotetramethylenedichlorosilane (0.5 mL; 3.82 mMol) in dry THF (5 mL) was added urea (0.275 g; 4.58 mmol). The mixture was then cooled to 0° C. and benzyl glycolate (0.54 mL; 3.82 mmol) was then added dropwise over a 7 minute span. The mixture was then taken off the ice bath and allowed to stir at room temperature for 1 hour. The biphasic mixture was then concentrated under high vacuum and diluted with chloroform. The aqueous layer was then soaked up with excess $Na_2SO_4$ and the mixture was filtered. The filtrate was concentrated to a light yellow crude liquid which was used without further purification.

Example 8

Preparation of 1-(2-(2-aminoethoxy)ethyl)-1H-pyrrole-2,5-dionetrifluoroacetate

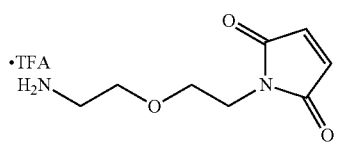 [SMILES: "·TFA" ; NCCOCCN1C(=O)C=CC1=O]

1-(2-(2-aminoethoxy)ethyl)-1H-pyrrole-2,5-dione trifluoroacetate made by a method reported by Weber et al. in *Bioconjugate Chem.*, 1:431 (1990) and in U.S. Pat. No. 5,053,503, which are hereby incorporated by reference in their entirety.

Example 9

Preparation of (S)-2-(4-((2-amino-4-hydroxypteridin-6-yl)methylamino)benzamido)-5-(2-(2-(2-aminoethoxy)ethoxy)ethylamino)-5-oxopentanoic acid

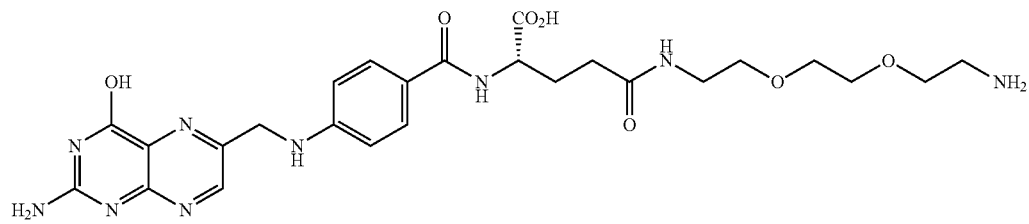 [SMILES: NCCOCCOCCNC(=O)CC[C@H](NC(=O)c1ccc(NCc2cnc3nc(N)nc(O)c3n2)cc1)C(=O)O]

Step A. To pteroic acid dihydrochloride (100 mg, 0.26 mmol), triethylamine (1.5 mL, 11 mmol), and (S)-5-tert-butyl 1-methyl 2-aminopentanedioate hydrochloride (162 mg, 0.64 mmol) in N,N-dimethylformamide (3 mL), 2-(2-pyridon-1-yl)-1,1,3,3-tetramethyluronium tetrafluoroborate (190 mg, 0.64 mmol) was added in one portion. The reaction was stirred at ambient temperature for 16 hours. After this time, the reaction was purified by semi-preparative HPLC (1:4 to 0:100 $H_2O/CH_3CN$ over 25 minutes) to afford(S)-5-tert-butyl 1-methyl 2-(4-((2-amino-4-hydroxypteridin-6-yl)methylamino)benzamido)pentanedioate (55 mg, 34%) as a yellow solid: $^1H$ NMR (300 MHz, DMSO-$d_6$) δ 8.56 (s, 1H), 8.26 (d, J=6.6 Hz, 1H), 7.65 (d, J=8.0 Hz, 2H), 6.94 (bs, 4H), 6.65 (d, J=8.0 Hz, 2H), 4.58-4.34 (m, 3H), 3.61 (s, 3H), 2.36-2.25 (m, 2H), 2.10-1.88 (m, 2H), 1.37 (s, 9H); MM-APCI MS m/z=510 [M−H]$^-$.

Step B. To a suspension of (S)-5-tert-butyl 1-methyl 2-(4-((2-amino-4-hydroxypteridin-6-yl)methylamino)benzamido)pentanedioate (230 mg, 0.45 mmol) in methylene chloride (10 mL) chilled to 0° C. trifluoroacetic acid (5 mL) was added. The reaction was gradually warmed to ambient temperature and stirred for 18 hours. After this time, the reaction was concentrated under reduced pressure to afford crude(S)-4-(4-(((2-amino-4-hydroxypteridin-6-yl)methyl)amino)benzamido)-5-methoxy-5-oxopentanoic acid (242 mg, >100%) as a brown oil, which was used in the next step without further purification: MM-APCI MS m/z=456 [M+H]$^+$.

Step C. To (S)-4-(4-((2-amino-4-hydroxypteridin-6-yl)methylamino)benzamido)-5-methoxy-5-oxopentanoic acid (240 mg, 0.53 mmol, crude), triethylamine (0.3 mL, 2.2 mmol), and tert-butyl 2-(2-(2-aminoethoxy)ethoxy)ethylcarbamate (150 mg, 0.60 mmol) in N,N-dimethylformamide (3 mL), 2-(2-pyridon-1-yl)-1,1,3,3-tetramethyluronium tetrafluoroborate (261 mg, 0.88 mmol) was added in one portion. The reaction was stirred at ambient temperature for 16 hours. After this time, the product was crashed out with diethyl ether and collected by suction filtration. The solids were washed with methylene chloride (30 mL) to afford crude (S)-methyl 18-(4-((2-amino-4-hydroxypteridin-6-yl)methylamino)benzamido)-2,2-dimethyl-4,15-dioxo-3,8,11-trioxa-5,14-diazanonadecan-19-oate (225 mg, 62%) as an orange-brown solid, which was used in the next step without further purification: MM-APCI MS m/z=684 [M−H]$^-$.

Step D. (S)-methyl 18-(4-((2-amino-4-hydroxypteridin-6-yl)methylamino)benzamido)-2,2-dimethyl-4,15-dioxo-3,8,11-trioxa-5,14-diazanonadecan-19-oate (225 mg, 0.33 mmol, crude) in 6 M aqueous hydrochloric acid (20 mL) was stirred at ambient temperature for 2 hours. After this time, the reaction was purified by semi-preparative HPLC (0-70% $H_2O/CH_3CN$ with 0.05% TFA over 25 minutes) to give a mixture of the desired acid and the methyl ester (190 mg) as a yellow solid. To this mixture lithium hydroxide (30 mg, 1.25 mmol) was added along with a 1:1 THF/$H_2O$ mixture (6 mL). This mixture was stirred at ambient temperature for 2 hours. After this time, the THF was removed under reduced pressure, and the reaction was purified by semi-preparative HPLC (0-70% $H_2O/CH_3CN$ with 0.05% TFA over 25 min) to afford (S)-2-(4-((2-amino-4-hydroxypteridin-6-yl)methylamino)benzamido)-5-(2-(2-(2-aminoethoxy)ethoxy)ethylamino)-5-oxopentanoic acid (185 mg, 100%) as a yellow solid that was obtained from lyophilization: $^1H$ NMR (500 MHz, DMSO-$d_6$) δ 12.47 (vbs, 1H), 11.44 (vbs, 1H), 8.64 (s, 1H), 8.17 (d, J=7.5 Hz, 1H), 7.87 (t, J=5.5 Hz, 1H), 7.72 (bs, 2H), 7.65 (d, J=9.0 Hz, 2H), 6.93 (bs, 2H), 6.64 (d, J=9.0 Hz, 2H), 4.48 (s, 2H), 4.30-4.26 (m, 1H), 3.57-3.49 (m, 6H), 3.37 (t, J=6.0 Hz, 2H), 3.22-3.13 (m, 2H), 2.99-2.94 (m, 2H), 2.19 (t, J=7.5 Hz, 2H), 2.08-2.01 (m, 1H), 1.93-1.85 (m, 1H), exchangeable proton not observed (1H); ESI MS m/z=570 [M−H]$^-$.

Example 10

Preparation of (S)-1-amino-16-(4-((2-amino-4-hydroxypteridin-6-yl)methylamino)benzamido)-13-oxo-3,6,9-trioxa-12-azaheptadecan-17-oic acid

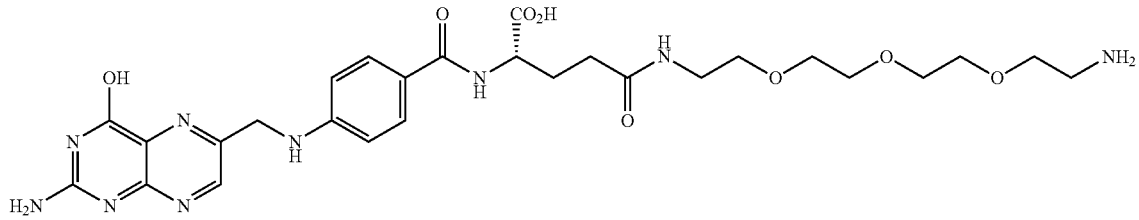 [SMILES: NCCOCCOCCOCCNC(=O)CC[C@H](NC(=O)c1ccc(NCc2cnc3nc(N)nc(O)c3n2)cc1)C(=O)O]

Step A. To (S)-4-amino-5-tert-butoxy-5-oxopentanoic acid (1.50 g, 7.38 mmol) in 1,4-dioxane (40 mL) chilled to 0° C., sodium carbonate (196 mg, 1.85 mmol) in water (20 mL) was added followed by Fmoc chloride (2.11 g, 8.16 mmol). The reaction was gradually warmed to ambient temperature and stirred at ambient temperature for 16 hours. After this time, the reaction was made slightly acidic (pH=6) with 2 M hydrochloric acid and the pH adjusted to ~3 with 1 M citric acid (~80 mL). The resulting mixture was extracted with ethyl acetate (3×100 mL). The combined organics were dried over sodium sulfate, filtered, and the filtrate concentrated under reduced pressure. The residue obtained was purified by silica gel column chromatography eluting with hexanes to a 3:2 ethyl acetate/hexane mixture to afford (S)-4-(((9H-fluoren-9-yl)methoxy)carbonylamino)-5-tert-butoxy-5-oxopentanoic acid (3.10 g, 99%) as a white solid: $^1$H NMR (300 MHz, CDCl$_3$) δ carboxylic acid peak (1H) not observed as it was too broadened out, 7.76 (d, J=7.5 Hz, 2H), 7.61-7.58 (m, 2H), 7.42-7.26 (m, 4H), 5.45 (d, J=7.8 Hz, 1H), 4.48-4.19 (m, 4H), 2.51-2.34 (m, 2H), 2.28-2.14 (m, 1H), 1.99-1.88 (m, 1H), 1.47 (s, 9H); ESI MS m/z=448 [M+Na]$^+$.

Step B. To (S)-4-(((9H-fluoren-9-yl)methoxy)carbonylamino)-5-tert-butoxy-5-oxopentanoic acid (721 mg, 1.69 mmol), tert-butyl 2-(2-(2-(2-aminoethoxy)ethoxy)ethoxy)ethylcarbamate (595 mg, 2.04 mmol), and N,N-diisopropylethylamine (0.9 mL, 5.2 mmol) in THF (20 mL), N,N,N',N'-tetramethyl-O-(1H-benzotriazol-1-yl)uroniumhexafluorophosphate (1.29 g, 3.40 mmol) was added in one portion. The reaction was stirred at ambient temperature for 16 hours. After this time, the reaction was dry loaded onto silica and purified by silica gel column chromatography eluting with hexanes to ethyl acetate to afford (S)-tert-butyl 1-(9H-fluoren-9-yl)-24,24-dimethyl-3,8,22-trioxo-2,12,15,18,23-pentaoxa-4,9,21-triazapentacosane-5-carboxylate (1.17 g, 99%) as an off-white solid: $^1$H NMR (300 MHz, CDCl$_3$) δ 7.77 (d, J=7.5 Hz, 2H), 7.62-7.59 (m, 2H), 7.44-7.38 (m, 2H), 7.36-7.26 (m, 2H), 6.78 (bs, 1H), 6.07 (bs, 2H), 5.77 (bs, 1H), 4.42-4.38 (m, 2H), 4.27-4.17 (m, 2H), 3.80-3.70 (m, 2H), 3.68-3.46 (m, 9H), 3.31-3.12 (m, 4H), 2.37-2.13 (m, 3H), 2.00-1.87 (m, 1H), 1.47 (s, 9H), 1.45 (s, 9H); ESI MS m/z=700 [M+H]$^+$.

Step C. To (S)-tert-butyl 1-(9H-fluoren-9-yl)-24,24-dimethyl-3,8,22-trioxo-2,12,15,18,23-pentaoxa-4,9,21-triazapentacosane-5-carboxylate (1.18 g, 1.69 mmol), in 1,4-dioxane (45 mL) chilled to 0° C. concentrated ammonia hydroxide (9.5 mL, 133 mmol) was added dropwise over 15 minutes. The reaction was stirred at 0° C. for 2 hours and then at ambient temperature for 16 hours. After this time, the reaction was dry loaded onto silica and purified by silica gel column chromatography eluting with methylene chloride to 3:17 methanol/methylene chloride to afford (S)-tert-butyl 21-amino-2,2-dimethyl-4,18-dioxo-3,8,11,14-tetraoxa-5,17-diazadocosan-22-oate (802 mg, 99%) as an off-white solid: $^1$H NMR (300 MHz, CDCl$_3$) δ 6.92 (bs, 1H), 5.14 (bs, 3H), 3.90-3.85 (m, 1H), 3.80-3.54 (m, 9H), 3.49-3.45 (m, 2H), 3.34-3.29 (m, 2H), 3.23-3.15 (m, 3H), 2.61-2.41 (m, 2H), 2.33-2.23 (m, 1H), 2.15-2.03 (m, 1H), 1.48 (s, 9H), 1.46 (s, 9H); ESI MS m/z=478 [M+H]$^+$.

Step D. To pteroic acid dihydrochloride (424 mg, 1.10 mmol) and triethylamine (0.75 mL, 5.50 mmol) in N,N-dimethylformamide (10 mL), propanephosphonic anhydride 50% solution in N,N-dimethylformamide (1.30 mL, 2.23 mmol) was added. After the reaction stirred for 45 minutes at ambient temperature, (S)-tert-butyl 21-amino-2,2-dimethyl-4,18-dioxo-3,8,11,14-tetraoxa-5,17-diazadocosan-22-oate (802 mg, 1.68 mmol) in N,N-dimethylformamide (5 mL) was added, and the reaction was stirred for 16 h at ambient temperature. After this time, the reaction was diluted with diethyl ether (150 mL) and the filtered to give (S)-tert-butyl 21-(4-((2-amino-4-hydroxypteridin-6-yl)methylamino)benzamido)-2,2-dimethyl-4,18-dioxo-3,8,11,14-tetraoxa-5,17-diazadocosan-22-oate (849 mg, obtained as a 1:1 mixture with pteroic acid, 50%) as a brown solid that was used in the next step without further purification: MM-APCI MS m/z=794 [M+Na]$^+$.

Step E. To (S)-tert-butyl 21-(4-((2-amino-4-hydroxypteridin-6-yl)methylamino)benzamido)-2,2-dimethyl-4,18-dioxo-3,8,11,14-tetraoxa-5,17-diazadocosan-22-oate (425 mg, 0.551 mmol) aqueous 6 M hydrochloric acid (10 mL) was added. The reaction was stirred at ambient temperature for 16 hours. After this time, the reaction was not complete. The reaction was concentrated under reduced pressure and dissolved in N,N-dimethylformamide (5 mL). To the resulting mixture TFA (7 mL) was added and reaction mixture stirred at ambient temperature for 16 hours. After this time, the reaction was diluted with 6 M aqueous hydrochloric acid (50 mL) and filtered through diatomaceous earth. The filter cake was rinsed with methanol (40 mL), and the filtrate obtained was concentrated under reduced pressure. The residue obtained was purified by semi-preparative HPLC (100:0 to 3:7 H$_2$O/CH$_3$CN with 0.05% TFA over 25 min). Further purification by semi-preparative HPLC (100:0 to 3:7 H$_2$O/CH$_3$CN with 0.05% TFA over 25 min) was required to obtain pure (S)-1-amino-16-(4-((2-amino-4-hydroxypteridin-6-yl)methylamino)benzamido)-13-oxo-3,6,9-trioxa-12-azaheptadecan-17-oic acid (121 mg, 36%) as a yellow solid that was obtained via lyophilization: $^1$H NMR (300 MHz, DMSO-d$_6$) δ 10.88 (vbs, 1H), 8.65 (s, 1H), 8.20 (d, J=6.6 Hz, 1H), 7.95-7.89 (m, 1H), 7.78 (bs, 2H), 7.65 (d, J=8.7 Hz, 2H), 7.00-6.90 (m, 2H), 6.64 (d, J=8.7 Hz, 2H), 4.49 (s, 2H), 4.31-4.28 (m, 1H), 3.78-3.45 (m, 12H), 3.43-3.35 (m, 2H), 3.28-3.20 (m, 2H), 3.02-2.98 (m, 2H), 2.23-2.17 (m, 2H), 2.12-2.00 (m, 1H), 1.99-1.87 (m, 1H); ESI MS m/z=614 [M−H]⁻.

Example 11

Preparation of (3aR,3a¹R,4R,5S,10bR)-methyl 4-((1-(5-((2-(2-(2,5-dioxo-2,5-dihydro-1H-pyrrol-1-yl)ethoxy)ethyl)amino)-5-oxopentyl)silinan-1-yl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate

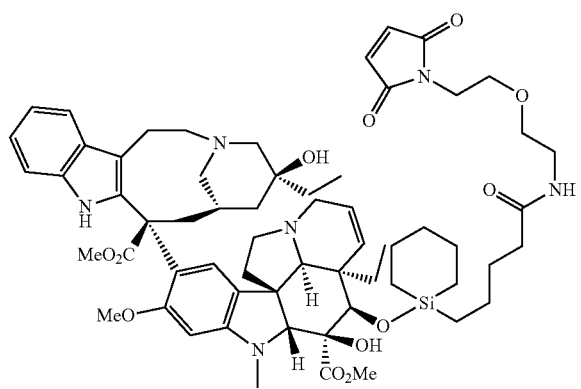

Step A. To a solution of 4-desacetylvinblastine (100 mg; 0.130 mmol) and imidazole (111 mg; 1.625 mmol) in 0.7 mL of dry DMF under nitrogen was added a crude sample of benzyl 5-(1-chlorosilinan-1-yl)pentanoate of undetermined titre. A total of 233 mg of crude silyl chloride was added in 3 portions over a 3 hour period. After stirring for an additional 1.5 hours, the reaction was quenched with H₂O and extracted with CH₂Cl₂ (3×5 mL). The combined organic layers were dried, filtered and concentrated. The residue was purified by column chromatography (C18, 10-100% acetonitrile in water, 35 minute gradient) to give 54 mg (39%) of (3aR,3a¹R,4R,5S,10bR)-methyl 4-((1-(5-(benzyloxy)-5-oxopentyl)silinan-1-yl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate as a white solid. ¹H NMR (500 MHz, CDCl₃) δ 9.41 (brd s, 1H), 8.17 (s, 1H), 7.53 (d, J=7.9 Hz, 1H), 7.37-7.33 (m, 4H), 7.34-7.27 (m, 1H), 7.20-7.13 (m, 2H), 7.10 (ddd, J=7.9, 6.0, 1.8 Hz, 1H), 6.62 (s, 1H), 6.09 (s, 1H), 5.78 (dd, J=10.1, 5.0 Hz, 1H), 5.47 (d, J=10.3 Hz, 1H), 5.14-5.08 (m, 2H), 4.17 (s, 1H), 3.95 (t, J=14.0 Hz, 1H), 3.78 (s, 3H), 3.76 (s, 3H), 3.70-3.63 (m, 1H), 3.62 (s, 1H), 3.60 (s, 3H), 3.38 (d, J=13.6 Hz, 1H), 3.34-3.27 (m, 2H), 3.23 (dt, J=5.2, 4.7 Hz, 1H), 3.16-3.08 (m, 2H), 2.84-2.75 (m, 3H), 2.70 (s, 3H), 2.66 (s, 1H), 2.43-2.33 (m, 4H), 2.27 (d, J=15.4 Hz, 1H), 2.06 (ddd, J=13.8, 8.6, 5.6 Hz, 1H), 1.99-1.90 (m, 2H), 1.76-1.65 (m, 3H), 1.63-1.52 (m, 3H), 1.51-1.42 (m, 3H), 1.42-1.34 (m, 3H), 1.34-1.28 (m, 2H), 1.27-1.17 (m, 2H), 0.93-0.84 (m, 7H), 0.83-0.69 (m, 6H); MS (ESI+) m/z 1057.5 (M+H); HPLC 98.6% (AUC), t_R 17.54 min (Method A).

Step B. To a solution of (3aR,3a¹R,4R,5S,10bR)-methyl 4-((1-(5-(benzyloxy)-5-oxopentyl)silinan-1-yl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate (90 mg; 0.085 mmol) in 7 mL of ethyl acetate was added excess 10% palladium on carbon (90 mg) with stirring. The suspension was stirred under an atmosphere of hydrogen (balloon pressure) for 2 hours prior to filtration through a celite plug. The celite plug was washed with ethyl acetate then methanol. The filtrate was concentrated under reduced pressure and the resultant crude 5-(1-(((3aR,3a¹R,4R,5S,10bR)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-5-(methoxycarbonyl)-6-methyl-3a,3a¹,4,5,5a,6,11,12-octahydro-1H-indolizino[8,1-cd]carbazol-4-yl)oxy)silinan-1-yl)pentanoic acid (72 mg; 88% crude yield) was carried on without further purification. MS (ESI+) m/z 967.5 (M+H).

Step C. To an ice cold solution of crude 5-(1-(((3aR,3a¹R,4R,5S,10bR)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-5-(methoxycarbonyl)-6-methyl-3a,3a1,4,5,5a,6,11,12-octahydro-1H-indolizino[8,1-cd]carbazol-4-yl)oxy)silinan-1-yl)pentanoic acid (39 mg; est. 0.040 mmol) in 9 mL CH₂Cl₂ was added 4-methylmorpholine (0.443 mL; 4.03 mmol) with stirring. Added sequentially were then EDCI-HCl (31 mg; 0.161 mmol) and HOBt (22 mg; 0.161 mmol). A solution of crude 1-(2-(2-aminoethoxy)ethyl)-1H-pyrrole-2,5-dionetrifluoroacetate (120 mg) in 4 mL of CH₂Cl₂ was then added dropwise to the mixture. Following the addition, the mixture was allowed to warm to room temperature and then stirred for 18 hours before being quenched with H₂O. The mixture was extracted with CH₂Cl₂ (3×10 mL). The combined organic layers were dried, filtered and concentrated under reduced pressure. The resultant residue was purified by column chromatography (C18, 10-100% acetonitrile in water, 40 minute gradient) to give 21 mg (37% two-steps) of (3aR,3a¹R,4R,5S,10bR)-methyl 4-((1-(5-((2-(2-(2,5-dioxo-2,5-dihydro-1H-pyrrol-1-yl)ethoxy)ethyl)amino)-5-oxopentyl)silinan-1-yl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate as a white solid. ¹H NMR (500 MHz, CDCl₃) δ 9.41 (brd s, 1H), 8.15 (s, 1H), 7.53 (d, J=7.8 Hz, 1H), 7.19-7.14 (m, 2H), 7.10 (ddd, J=7.9, 5.1, 2.9 Hz, 1H), 6.72 (s, 2H), 6.62 (s, 1H), 6.16 (brd t, J=4.8 Hz, 1H), 6.10 (s, 1H), 5.79 (dd, J=10.2, 4.9 Hz, 1H), 5.47 (d, J=10.3 Hz, 1H), 4.17 (s, 1H), 3.95 (t, J=14.2 Hz, 1H), 3.79 (s, 3H), 3.79 (s, 3H), 3.71 (t, J=5.3 Hz, 2H), 3.71-3.66 (m, 1H), 3.64-3.57 (m, 6H), 3.51 (t, J=5.2 Hz, 2H), 3.42-3.35 (m, 3H), 3.35-3.27 (m, 2H), 3.23 (dt, J=5.3, 4.6 Hz, 1H), 3.17-3.09 (m, 2H), 2.84-2.76 (m, 3H), 2.70 (s, 3H), 2.66 (s, 1H), 2.44-2.35 (m, 2H), 2.28 (d, J=15.4 Hz, 1H), 2.19 (t, J=7.6 Hz, 2H), 2.09-2.01 (m, 1H), 1.99-1.91 (m, 2H), 1.76-1.69 (m, 1H), 1.70-1.64 (m, 2H), 1.62-1.52 (m, 3H), 1.51-1.43 (m, 3H), 1.43-1.35 (m, 3H), 1.32 (quart, J=7.4 Hz, 2H), 1.28-1.17 (m, 2H), 0.94-0.82 (m, 8H), 0.82-0.69 (m, 5H); MS (ESI+) m/z 1133.5 (M+H); HPLC 97.6% (AUC), t_R 14.15 min (Method A).

Example 12

Preparation of (3aR,3a¹R,4R,5S,10bR)-methyl 4-((1-(5-(benzyloxy)-5-oxopentyl)silolan-1-yl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate

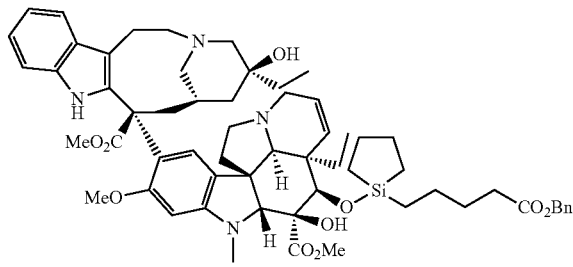

To a solution of 4-desacetylvinblastine (100 mg; 0.130 mmol) and imidazole (111 mg; 1.625 mmol in 0.7 mL of dry DMF under nitrogen was added a crude sample of benzyl 5-(1-chlorosilolan-1-yl)pentanoate of undetermined titre. A total of 200 mg of crude silyl chloride was added in 2 portions over a 4 hour period. After stirring for an additional 1.5 hours at room temperature, the reaction was quenched with $H_2O$ and extracted with $CH_2Cl_2$ (3×5 mL). The combined organic layers were dried, filtered and concentrated. The residue was purified by column chromatography (C18, 10-100% acetonitrile in water, 55 minute gradient) to give 25 mg (18%) of (3aR,3a¹R,4R,5S,10bR)-methyl 4-((1-(5-(benzyloxy)-5-oxopentyl)silolan-1-yl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate as a white solid. ¹H NMR (500 MHz, $CDCl_3$) δ 9.44 (brd s, 1H), 8.14 (s, 1H), 7.53 (d, J=7.8 Hz, 1H), 7.37-7.30 (m, 5H), 7.17-7.14 (m, 2H), 7.13-1.07 (m, 1H), 6.62 (s, 1H), 6.09 (s, 1H), 5.79 (dd, J=10.1, 5.0 Hz, 1H), 5.50 (d, J=10.3 Hz, 1H), 5.14-5.08 (m, 2H), 4.20 (s, 1H), 3.95 (t, J=14.2 Hz. 1H), 3.77 (s, 6H), 3.69-3.63 (m, 1H), 3.63 (s, 1H), 3.61 (s, 3H), 3.38 (d, J=13.9 Hz, 1H), 3.34-3.21 (m, 3H), 3.17-3.07 (m, 2H), 2.83-2.76 (m, 3H), 2.70 (s, 3H), 2.66 (s, 1H), 2.44-2.33 (m, 4H), 2.27 (dd, J=15.0, 2.9 Hz, 1H), 2.09-2.03 (m, 1H), 1.79-1.66 (m, 5H), 1.52-1.43 (m, 4H), 1.41-1.28 (m, 6H), 1.28-1.18 (m, 2H), 0.92-0.83 (m, 7H), 0.80-0.98 (m, 3H), 0.63-0.52 (m, 3H); MS (ESI+) m/z 1043.5 (M+H); HPLC 94.4% (AUC), $t_R$ 16.92 min (Method A).

Example 13

Preparation of (3aR,3a¹R,4R,5S,10bR)-methyl 4-(((5-(benzyloxy)-5-oxopentyl)diphenylsilyl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate

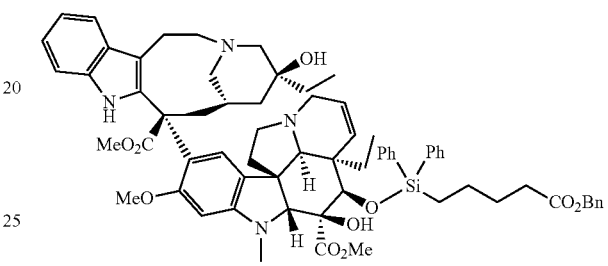

To a solution of 4-desacetylvinblastine (71 mg; 0.092 mmol) and imidazole (78 mg; 1.15 mmol) in 0.5 mL of dry DMF under nitrogen was added a crude sample of benzyl 5-(chlorodiphenylsilyl)pentanoate (113 mg; 0.277 mMol) of undetermined titre. After stirring for 2 hours at room temperature under $N_2$, the reaction was quenched with $H_2O$ and extracted with $CH_2Cl_2$ (3×5 mL). The combined organic layers were dried, filtered and concentrated. The residue was purified by column chromatography (C18, 10-100% acetonitrile in water, 55 minute gradient) to give 77 mg (73%) of (3aR,3a¹R,4R,5S,10bR)-methyl 4-(((5-(benzyloxy)-5-oxopentyl)diphenylsilyl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate as a white solid. ¹H NMR (500 MHz, $CDCl_3$) δ 9.08 (brd s, 1H), 7.96 (s, 1H), 7.70 (d, J=7.2 Hz, 2H), 7.55 (d, J=7.1 Hz, 2H), 7.50 (d, J=8.1 Hz, 1H), 7.41-7.28 (m, 11H), 7.15-7.05 (m, 3H), 6.52 (s, 1H), 6.02 (s, 1H), 5.69 (dd, J=10.0, 4.2 Hz, 1H), 5.33 (d, J=10.2 Hz, 1H), 5.06 (s, 2H), 4.37 (s, 1H), 3.94 (t, J=14.0 Hz, 1H), 3.76 (s, 3H), 3.68-3.58 (m, 5H), 3.42-3.35 (m, 4H), 3.32 (d, J=15.7, 4.4 Hz, 1H), 3.30-3.20 (m, 2H), 3.14-3.06 (m, 2H), 2.79 (s, 2H), 2.71 (d, J=15.8 Hz, 1H), 2.64 (s, 3H), 2.52 (s, 1H), 2.40-2.28 (m, 4H), 2.24 (d, J=15.1 Hz, 1H), 2.07 (ddd, J=14.0, 8.2, 6.2 Hz, 1H), 1.75-1.66 (m, 3H), 1.47-1.23 (m, 9H), 1.18 (q, J=7.0 Hz, 1H), 0.94-0.85 (m, 4H), 0.80 (brd s, 1H), 0.58 (t, J=7.2 Hz, 3H); MS (ESI+) m/z 1141.5 (M+H); HPLC 98.6% (AUC), $t_R$ 17.81 min (Method A).

Example 14

Preparation of (3aR,3a¹R,4R,5S,10bR)-methyl 4-(((5-((2-(2-(2,5-dioxo-2,5-dihydro-1H-pyrrol-1-yl)ethoxy)ethyl)amino)-5-oxopentyl)(methyl)(phenyl)silyl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹4,5,5a,6,11,12-octahydro-1H-indolizino[8,1-cd]carbazole-5-carboxylate (mixture of diastereomers)

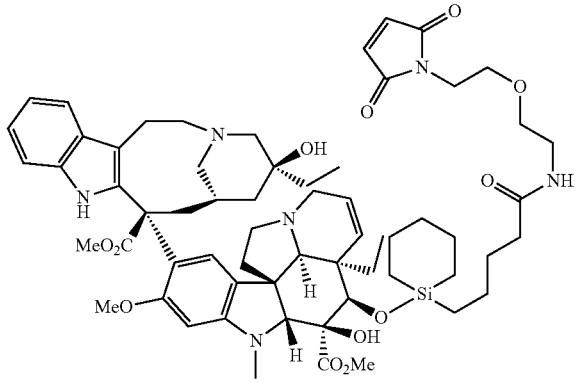

Step A. To a solution of 4-desacetylvinblastine (45 mg; 0.058 mmol) and imidazole (50 mg; 0.73 mmol) in 0.6 mL of dry DMF under nitrogen was added a crude sample of racemic benzyl 5-(chloro(methyl)(phenyl)silyl)pentanoate of undetermined titre. A total of 181 mg of crude silyl chloride was added in 3 portions over a 4.5 hour period. After stirring for an additional 1.5 hours at room temperature, the reaction was quenched with H$_2$O and extracted with CH$_2$Cl$_2$ (3×5 mL). The combined organic layers were dried, filtered and concentrated. The residue was purified by column chromatography (silica, 0-10% methanol in methylene chloride, 30 minute gradient) to give 52 mg (82%) of a diastereomeric mixture of (3aR,3a¹R,4R,5S,10bR)-methyl 4-(((5-(benzyloxy)-5-oxopentyl)(methyl)(phenyl)silyl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate as a yellow solid. LCMS indicated the sample was a 1:1 mixture of both stereoisomers. ¹H NMR (500 MHz, CDCl$_3$) key resonances: δ 5.76 (dd, J=10.2, 4.2 Hz, 1H; disubstituted olefin for diastereomer 'a'), 5.66 (dd, J=10.2, 4.3 Hz, 1H; disubstituted olefin for diastereomer 'b'), 5.42 (dd, J=10.1 Hz, 1H; disubstituted olefin for diastereomer 'a'), 5.20 (dd, J=10.0 Hz, 1H; disubstituted olefin for diastereomer 'b') 5.08 (s, 2×2H; benzyl methylene CH$_2$s overlapping for both diastereomers), 4.28 (s, 1H; H$_4$ for diastereomer 'a'), 4.23 (s, 1H; H$_4$ for diastereomer 'b'), MS (ESI+) m/z 1079.9 (M+H); HPLC 88.9% (AUC), t$_R$ 10.26 min (Method B).

Step B. To a solution of a diastereomeric mixture of (3aR,3a¹R,4R,5S,10bR)-methyl 4-(((5-(benzyloxy)-5-oxopentyl)(methyl)(phenyl)silyl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate (34 mg; 0.0315 mMol) in 8 mL of EtOAc, 10% Pd/C (25 mg) was added with stirring. The reaction vessel atmosphere was purged with argon gas followed by a subsequent purge with H$_2$. The H$_2$ atmosphere was maintained via a balloon attachment and the mixture was allowed to stir at room temperature. After 5 hours the reaction vessel atmosphere was purged with argon before being exposed to air and the mixture was filtered through a celite plug. The plug was washed with EtOAc and the filtrate was concentrated under reduced pressure to obtain 5-((((3aR,3a¹R,4R,5S,10bR)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-5-(methoxycarbonyl)-6-methyl-3a,3a¹,4,5,5a,6,11,12-octahydro-1H-indolizino[8,1-cd]carbazol-4-yl)oxy)(methyl)(phenyl)silyl)pentanoic acid (25 mg; 80% crude yield) as a crude solid.

Step C. Crude 5-((((3aR,3a¹R,4R,5S,10bR)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-5-(methoxycarbonyl)-6-methyl-3a,3a¹,4,5,5a,6,11,12-octahydro-1H-indolizino[8,1-cd]carbazol-4-yl)oxy)(methyl)(phenyl)silyl)pentanoic acid (25 mg, est. 0.025 mmol) was dissolved in CH$_2$Cl$_2$ (9 mL) and cooled to 0° C. To this solution was added 4-methylmorpholine (0.277 mL; 2.52 mmol) with stirring. Added sequentially were then EDCI.HCl (19 mg; 0.101 mmol) and HOBt (14 mg; 0.101 mmol). A solution of crude 1-(2-(2-aminoethoxy)ethyl)-1H-pyrrole-2,5-dionetrifluoroacetate (75 mg) in 2 mL of CH$_2$Cl$_2$ was then added dropwise to the mixture. Following the addition, the reaction mixture was allowed to warm to room temperature and stir for 16 hours before being quenched with H$_2$O (10 mL) and extracted with CH$_2$Cl$_2$ (3×10 mL). The combined organic layers were dried, filtered and concentrated under reduced pressure. The resultant residue was subjected to silica chromatography to give 15.5 mg of a diastereomeric mixture of (3aR,3a¹R,4R,5S,10bR)-methyl 4-(((5-((2-(2-(2,5-dioxo-2,5-dihydro-1H-pyrrol-1-yl)ethoxy)ethyl)amino)-5-oxopentyl)(methyl)(phenyl)silyl)oxy)-3a-ethyl-945S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate as a yellow, glassy solid. ¹H NMR (300 MHz, CDCl$_3$) key resonances: δ 6.69 (s, 2H, maleimide olefin for diastereomer 'a'), 6.68 (s, 2H, maleimide olefin for diastereomer 'b'); MS (ESI+) m/z 1155.5 (M+H); HPLC 67.7% (AUC), t$_R$ 8.32/8.40 min (Method B).

Example 15

Preparation of (3aR,3a¹R,4R,5S,10bR)-methyl 4-(((5-(benzyloxy)-5-oxopentyl)dimethylsilyl)oxy)-3a-ethyl-9-((5S,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a¹,4,5,5a,6,11,12-octahydro-1H-indolizino[8,1-cd]carbazole-5-carboxylate

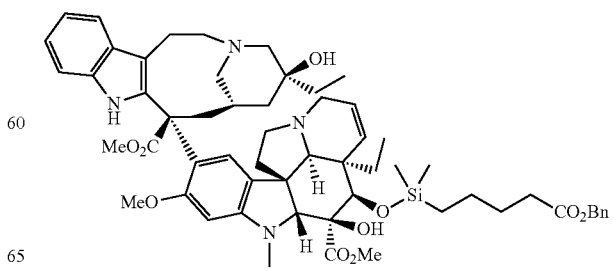

A mixture of 4-desacetylvinblastine (80 mg, 0.10 mmol), imidazole (17 mg, 0.25 mmol) and benzyl 5-(chlorodimethylsilyl)pentanoate (33 mg, 0.11 mmol) in DMF (0.2 mL) was stirred at room temperature for 17.5 hours. The reaction mixture was quenched with water (2 mL) and extracted with EtOAc (3×4 mL). The combined organic layers were washed with water, dried over $Na_2SO_4$ and concentrated. The residue was purified by flash column chromatography (12 g Gold column; 0-10% MeOH in $CH_2Cl_2$ gradient) to give the title compound as a white solid (56 mg, 53%): $^1$H NMR (500 MHz, $CDCl_3$) δ 9.50 (br s, 1H), 8.11 (s, 1H), 7.53 (d, J=7.9 Hz, 1H), 7.38-7.32 (m, 4H), 7.18-7.13 (m, 2H), 7.12-7.08 (m, 1H), 6.62 (s, 1H), 6.09 (s, 1H), 5.80 (dd, J=10.2, 3.8 Hz, 1H), 5.48-5.46 (m, 1H), 5.12 (s, 2H), 4.17 (s, 1H), 3.95 (t, J=14.0 Hz, 1H), 3.78 (s, 6H), 3.70-3.60 (m, 2H), 3.62 (s, 3H), 3.40-3.23 (m, 4H), 3.16-3.10 (m, 2H), 2.84-2.78 (m, 3H), 2.70 (s, 3H), 2.67 (s, 1H), 2.44-2.34 (m, 4H), 2.29-2.26 (m, 1H), 2.09-2.03 (m, 1H), 1.76-1.65 (m, 3H), 1.54-1.44 (m, 3H), 1.40-1.29 (m, 5H), 1.27-1.20 (m, 2H), 0.91-0.85 (m, 6H), 0.77-0.62 (m, 3H), 0.17 (s, 3H), 0.14 (s, 3H); ESI-MS: (M+H)=1017 m/z.

Example 16

Preparation of (2aR,4S,4aS,6R,9S,11S,12S,12bS)-9-(((2R,3S)-3-benzamido-2-hydroxy-3-phenylpropanoyl)oxy)-12-(benzoyloxy)-4-((1-(2-(benzyloxy)-2-oxoethoxy)silolan-1-yl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate

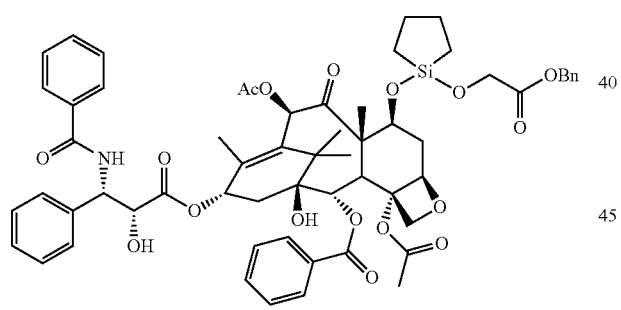

To a solution of paclitaxel (36 mg; 0.042 mmol) and imidazole (34 mg; 0.505 mmol) in 0.35 mL of dry DMF under nitrogen, was added a crude sample of benzyl 2-((1-chlorosilolan-1-yl)oxy)acetate of undetermined titre. A total of 103 mg of crude silyl chloride was added in 2 portions over a 3 hour period. After another 3 hours at room temperature, the reaction was quenched with $H_2O$ and extracted with $CH_2Cl_2$ (3×5 mL). The combined organic layers were dried, filtered and concentrated. The residue was purified by column chromatography to give 33 mg (71%) of (2aR,4S,4aS,6R,9S,11S,12S,12bS)-9-(((2R,3S)-3-benzamido-2-hydroxy-3-phenylpropanoyl)oxy)-12-(benzoyloxy)-4-((1-(2-(benzyloxy)-2-oxoethoxy)silolan-1-yl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate as a white solid. $^1$H NMR (300 MHz, $CDCl_3$) δ 8.13-8.10 (m, 2H), 7.77-7.74 (m, 2H), 7.61 (dddd, J=1.5, 1.5, 7.4, 7.4 Hz, 1H), 7.52-7.46 (m, 5H), 7.41-7.32 (m, 10H), 7.16 (d, J=9.0 Hz, 1H), 6.40 (s, 1H), 6.18 (dd, J=8.8, 8.8 Hz, 1H), 5.79 (dd, J=9.0, 2.4 Hz, 1H), 5.68 (d, J=7.0 Hz, 1H), 5.19 (s, 2H), 4.90 (dd, J=9.4, 1.4 Hz, 1H), 4.81-4.77 (m, 1H), 4.57 (dd, J=10.5, 6.7 Hz, 1H), 4.40-4.27 (m, 2H), 4.30 (d, J=8.4 Hz, 1H), 4.18 (d, J=9.1 Hz, 1H), 3.88 (d, J=5.3 Hz, 1H), 3.83 (d, J=6.9 Hz, 1H), 2.62-2.49 (m, 1H), 2.38 (s, 3H), 2.34-2.27 (m, 2H), 2.13 (s, 3H), 1.94 (ddd, J=14.0, 11.0, 2.0 Hz, 1H), 1.84 (s, 3H), 1.69 (s, 3H), 1.62-1.48 (m, 4H), 1.20 (s, 3H), 1.18 (s, 3H), 0.67-0.56 (m, 2H), 0.55-0.42 (m, 2H). MS (ESI+) m/z 1124.5 (M+Na).

Example 17

Preparation of (2aR,4S,4aS,6R,9S,11S,12S,12bS)-9-((02R,3S)-3-benzamido-2-((1-(2-(benzyloxy)-2-oxoethoxy)silinan-1-yl)oxy)-3-phenylpropanoyl)oxy)-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate

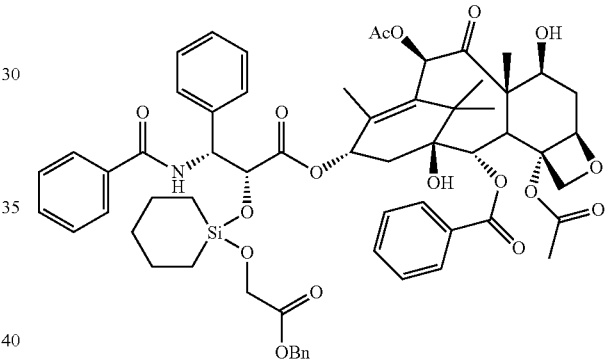

To a solution of paclitaxel (38 mg; 0.044 mmol) and imidazole (38 mg; 0.0556 mMol) in 0.3 mL of dry DMF under nitrogen, was added a crude sample of benzyl 2-((1-chlorosilinan-1-yl)oxy)acetate of undetermined titre. A total of 135 mg of crude silyl chloride was added in 3 portions over a 21 hour period. After stirring for another hour, the reaction was concentrated under reduced pressure and the residue was directly purified via column chromatography to give 32.8 mg of (2aR,4S,4aS,6R,9S,11S,12S,12bS)-9-(((2R,3S)-3-benzamido-2-((1-(2-(benzyloxy)-2-oxoethoxy)silinan-1-yl)oxy)-3-phenylpropanoyl)oxy)-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate (66%) as a colorless glassy solid. $^1$H NMR (500 MHz, $CDCl_3$) δ 8.13-8.12 (m, 2H), 7.78-7.77 (m, 2H), 7.61 (dddd, J=1.4, 1.4, 7.4, 7.4 Hz, 1H), 7.53-7.50 (m, 2H), 7.46 (dddd, J=1.4, 1.4, 7.4, 7.4 Hz, 1H), 7.41-7.31 (m, 12H), 7.28-7.24 (m, 1H), 6.27 (s, 1H), 6.24 (dd, J=9.4, 9.4 Hz, 2H), 5.75 (dd, J=8.7, 3.6 Hz, 1H), 5.67 (d, J=7.2 Hz, 1H), 5.18-5.09 (m, 2H), 5.04 (d, J=3.6 Hz, 1H), 4.96 (dd, J=9.7, 2.0 Hz, 1H), 4.43 (ddd, J=10.8, 6.5, 4.2 Hz, 1H), 4.30 (d, J=8.4 Hz, 1H), 4.20 (d, J=8.5 Hz, 1H), 4.20-4.11 (m, 2H), 3.80 (d, J=6.9 Hz, 1H), 2.54 (ddd, J=14.8, 9.6, 6.4

Hz, 1H), 2.48 (s, 3H), 2.31 (dd, J=15.3, 9.5 Hz, 1H), 2.22 (s, 3H), 2.03 (dd, J=15.7, 8.8 Hz, 1H) 1.91-1.82 (m, 4H), 1.68 (s, 3H), 1.65-1.52 (m, 4H), 1.37-1.27 (m, 2H), 1.23 (s, 3H), 1.12 (s, 3H), 0.72-0.67 (m, 1H), 0.65-0.58 (m, 2H), 0.48 (ddd, J=14.6, 9.1, 5.2 Hz, 1H). MS (ESI+) m/z 1138.4 (M+Na); HPLC 80% (AUC), $t_R$ 22.11 min (Method A).

Example 18

Preparation of (2aR,4S,4aS,6R,9S,11S,12S,12bS)-9-(((2R,3S)-3-benzamido-2-hydroxy-3-phenylpropanoyl)oxy)-12-(benzoyloxy)-4-(((5-(benzyloxy)-5-oxopentyl)dimethylsilyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate

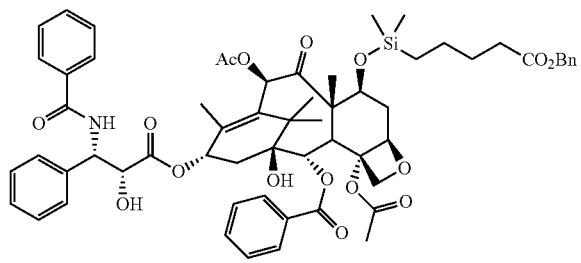 [SMILES: CC(=O)O[C@H]1C(=O)[C@@]2(C)C([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O[Si](C)(C)CCCCC(=O)OCc1ccccc1]

To a solution of Paclitaxel (52.5 mg; 0.061 mmol) and imidazole (40.1 mg; 0.590 mmol) in 0.25 mL of dry DMF under nitrogen was added the crude benzyl 5-(chlorodimethylsilyl)pentanoate of undetermined titre. A total of 197 mg of crude silyl chloride was added in 4 portions along with an additional 12 mg portion of imidazole over a 29 hour period. After stirring for an additional 12 hours, the reaction mixture was concentrated under reduced pressure and the resulting crude material was purified by column chromatography (silica gel, 0-50% ethyl acetate in hexanes, 40 minute gradient) to give 33 mg (27%) of (2aR,4S,4aS,6R,9S,11S,12S,12bS)-9-(((2R,3S)-3-benzamido-2-hydroxy-3-phenylpropanoyl)oxy)-12-(benzoyloxy)-4-(((5-(benzyloxy)-5-oxopentyl)dimethylsilyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate as a white waxy solid. $^1$H NMR (500 MHz, CDCl$_3$) δ 8.14-8.10 (m, 2H), 7.77-7.74 (m, 2H), 7.61 (dddd, J=1.3, 1.3, 7.4, 7.4 Hz, 1H), 7.52-7.46 (m, 5H), 7.43-7.38 (m, 4H), 7.36-7.29 (m, 6H), 7.07 (d, J=8.9 Hz, 1H), 6.38 (s, 1H), 6.17 (dd, J=9.6, 8.4 Hz, 1H), 5.80 (dd, J=9.0, 2.4 Hz, 1H), 5.67 (d, J=7.0 Hz, 1H), 5.11 (s, 2H), 4.90 (d, J=9.4 Hz, 1H), 4.79 (s, 1H), 4.37 (dd, J=10.3, 6.9 Hz, 1H), 4.29 (d, J=8.4 Hz, 1H), 4.18 (d, J=8.4 Hz, 1H), 3.80 (d, J=6.9 Hz, 1H) 3.63 (s, 1H), 2.45 (ddd, J=14.4, 9.5, 6.8 Hz, 1H), 2.37 (s, 3H), 2.37-2.33 (m, 2H), 2.31 (dd, J=8.8, 5.4 Hz, 1H), 2.16 (s, 3H), 1.88-1.81 (m, 3H), 1.68 (s, 3H), 1.66-1.61 (m, 3H), 1.34-1.27 (m, 2H), 1.21 (s, 3H), 1.18 (s, 3H), 0.92-0.82 (m, 2H), 0.60-0.48 (m, 2H), 0.08 (s, 3H), 0.07 (s, 3H). MS (ESI+) m/z 1102.4 (M+1); HPLC 96% (AUC), $t_R$ 22.72 min (Method A).

Example 19

Preparation of (3aR,3a$^1$R,4R,5S,10bR)-methyl 3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-4-((1-(5-((2-(2-(3-((3-methoxy-3-oxopropyl)thio)-2,5-dioxopyrrolidin-1-yl)ethoxy)ethyl)amino)-5-oxopentyl)silinan-1-yl)oxy)-6-methyl-3a,3a$^1$,4,5,5a,6,11,12-octahydro-1H-indolizino[8,1-cd]carbazole-5-carboxylate

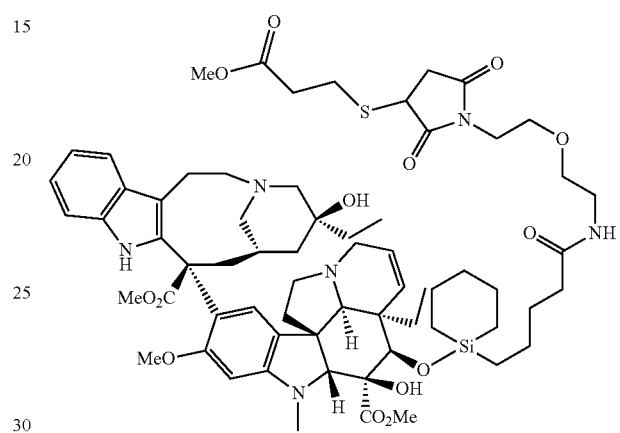

To a mixture of (3aR,3a$^1$R,4R,5S,10bR)-methyl 4-((1-(5-((2-(2-(2,5-dioxo-2,5-dihydro-1H-pyrrol-1-yl)ethoxy)ethyl)amino)-5-oxopentyl)silinan-1-yl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a$^1$,4,5,5a,6,11,12-octahydro-1H-indolizino[8,1-cd]carbazole-5-carboxylate (0.019 mg; 0.0167 mmol) inacetonitrile:0.01M PBS buffer (2:1) was added methyl-3-mercaptopropionate (0.036 mL; 0.335 mmol) with stirring. After stirring for 2 hours the reaction mixture was concentrated under reduced pressure before being extracted with ethyl acetate (3×5 mL). The combined organic layers were dried, filtered and concentrated under reduced pressure. The resultant residue was purified by column chromatography (C18, 10-100% acetonitrile in water, 50 minute gradient) to give 0.015 mg (72%) of (3aR,3a$^1$R,4R,5S,10bR)-methyl 3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-4-((1-(5-((2-(2-(3-((3-methoxy-3-oxopropyl)thio)-2,5-dioxopyrrolidin-1-yl)ethoxy)ethyl)amino)-5-oxopentyl)silinan-1-yl)oxy)-6-methyl-3a,3a$^1$,4,5,5a,6,11,12-octahydro-1H-indolizino[8,1-cd]carbazole-5-carboxylate as a white solid. $^1$H NMR (500 MHz, CDCl$_3$) δ 9.39 (brd s, 1H), 8.15 (s, 1H), 7.53 (d, J=7.8 Hz, 1H), 7.19-7.14 (m, 2H), 7.10 (ddd, J=7.9, 5.4, 2.5 Hz, 1H), 6.62 (s, 1H), 6.21 (brd t, J=5.2 Hz, 1H), 6.10 (s, 1H), 5.79 (ddd, J=10.1, 5.0, 1.0 Hz, 1H), 5.47 (d, J=10.3 Hz, 1H), 4.16 (s, 1H), 3.94 (t, J=14.0 Hz, 1H), 3.81 (ddd, J=9.2, 3.7, 1.0 Hz, 1H), 3.79 (s, 3H), 3.79 (s, 3H), 3.74-3.69 (m, 5H), 3.69-3.60 (m, 6H), 3.51 (t, J=5.2 Hz, 2H), 3.42-3.34 (m, 3H), 3.34-3.22 (m, 3H), 3.22-3.08 (m, 4H), 3.01 (dt, J=13.8, 6.9 Hz, 1H), 2.83-2.76 (m, 3H), 2.75-2.68 (m, 5H), 2.66 (s, 1H), 2.51 (ddd, J=18.7, 3.7, 1.0 Hz, 1H), 2.44-2.35 (m, 2H), 2.28 (dd, J=15.0, 2.3 Hz, 1H), 2.20 (t, J=7.6 Hz, 2H), 2.09-2.02 (m, 1H), 1.99-1.91 (m, 2H), 1.76-1.64 (m, 3H), 1.62-1.52 (m, 3H), 1.50-

1.43 (m, 3H), 1.42-1.35 (m, 3H), 1.32 (quart, J=7.5 Hz, 2H), 1.28-1.17 (m, 3H), 0.94-0.85 (m, 7H), 0.85-0.69 (m, 6H); MS (ESI+) m/z 1254.6 (M+H); HPLC 98.6% (AUC), $t_R$ 14.53 min (Method A).

Example 20

Preparation of (2S)-2-(4-(((2-amino-4-hydroxypteridin-6-yl)methyl)amino)benzamido)-20-(1-(((3aR,4R,5S,5aR,10bR)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-5-(methoxycarbonyl)-6-methyl-3a,3a1,4,5,5a,6,11,12-octahydro-1H-indolizino[8,1-cd]carbazol-4-yl)oxy)silinan-1-yl)-5,16-dioxo-9,12-dioxa-6,15-diazaicosan-1-oic acid

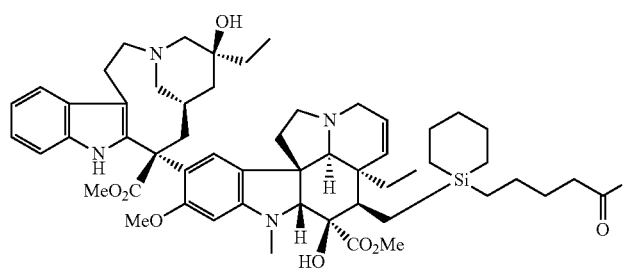

To a solution of (3aR,4R,5S,5aR,10bR)-methyl 3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-4-((1-(5-oxo-5-(perfluorophenoxy)pentyl)silinan-1-yl)oxy)-3a,3a1,4,5,5a,6,11,12-octahydro-1H-indolizino[8,1-cd]carbazole-5-carboxylate (25 mg, 0.022 mmol) in DMF (1 mL) at 0° C. under nitrogen was added N,N-diisopropylethylamine (0.012 mL, 0.07 mmol) followed by the addition of (S)-2-(4-(((2-amino-4-hydroxypteridin-6-yl)methyl)amino)benzamido)-5-((2-(2-(2-aminoethoxy)ethoxy)ethyl)amino)-5-oxopentanoic acid (25 mg, 0.044 mmol) and N,N-diisopropylethylamine (0.012 mL, 0.07 mmol) in DMF (1 mL). The reaction was warmed to room temperature and stirred under nitrogen for 5 hours. C18 solid support was added to the reaction and the solvent was removed in vacuo. The mixture was purified by reversed-phase silica gel chromatography (5-100% acetonitrile/water with 0.05% TEA in each). The product was isolated by direct lyopholyzation of the fractions to afford the title compound as a yellow solid: $^1$H NMR (500 MHz, CDCl$_3$) δ (select peaks) 9.45 (br s, 1H), 8.64 (s, 1H), 8.02-7.80 (m, 3H), 7.66-7.58 (m, 2H), 7.37 (d, J=7.7 Hz, 1H), 7.27 (d, J=7.9 Hz, 1H), 7.03-6.75 (m, 4H), 6.63 (d, J=8.7 Hz, 2H), 3.73 (s, 3H), 3.66 (s, 3H), 3.46 (s, 3H), 3.50-3.43 (m, 4H), 3.40-3.35 (m, 5H), 0.79 (t, J=7.4 Hz, 3H), 0.73 (t, J=7.1 Hz, 3H); ESI MS m/z=1521 [M+H]$^+$; HRMS: 1521.7621 (calculated 1520.7650 for C$_{79}$H$_{106}$N$_{13}$O$_{16}$Si; Δ=−2.0 PPM); HPLC (Method A, 254 nm) 15.8% (AUC), $t_R$=11.14 min.

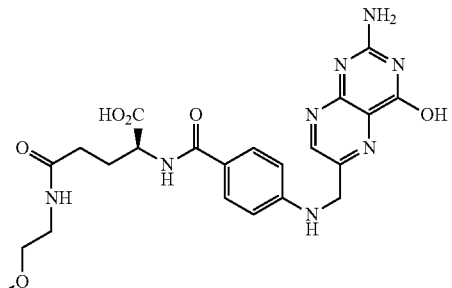

Example 21

Preparation of (2R)-2-(4-(((2-amino-4-hydroxypteridin-6-yl)methyl)amino)benzamido)-23-(1-(((3aR,4R,5S,5aR,10bR)-3a-ethyl-9-45S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-5-(methoxycarbonyl)-6-methyl-3a,3a1,4,5,5a,6,11,12-octahydro-1H-indolizino[8,1-cd]carbazol-4-yl)oxy)silinan-1-yl)-5,19-dioxo-9,12,15-trioxa-6,18-diazatricosan-1-oic acid

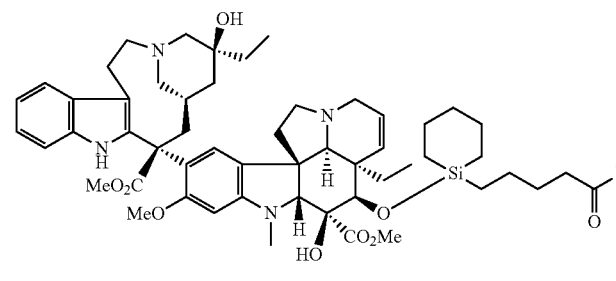

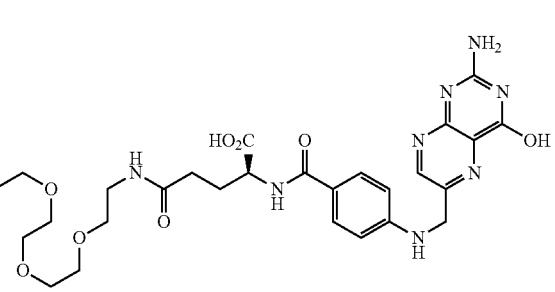

To a solution of (3aR,4R,5S,5aR,10bR)-methyl 4-((1-(5-((2,5-dioxopyrrolidin-1-yl)oxy)-5-oxopentyl)silinan-1-yl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8- methoxy-6-methyl-3a,3a1,4,5,5a,6,11,12-octahydro-1H-indolizino[8,1-cd]carbazole-5-carboxylate (25 mg, 0.023 mmol) in DMF (0.5 mL) at 0° C. under nitrogen was added N,N-diisopropylethylamine (0.02 mL, 0.1 mmol), (R)-1-amino-16-(4-(((2-amino-4-hydroxypteridin-6-yl)methyl)amino)benzamido)-13-oxo-3,6,9-trioxa-12-azaheptadecan-17-oic acid (14 mg, 0.023 mmol), and DMAP (~1 mg). The cooling bath was removed after 5 minutes and the reaction was stirred at room temperature for an additional 48 hours. The reaction was loaded directly onto a C18 silica gel column which was eluted with 5-100% acetonitrile/water with 0.05% TEA in each. The product was isolated by direct lyopholyzation of the fractions to afford Example 21 as a yellow solid: $^1$H NMR (500 MHz, CDCl$_3$) δ (select peaks) 9.45 (s, 1H), 8.62 (s, 1H), 8.00-7.72 (m, 2H), 7.61-7.59 (m, 1H), 7.37-7.27 (m, 1H), 6.99-6.88 (m, 2H), 6.64 (d, J=8.8 Hz, 1H), 6.51 (d, J=5.1 Hz, 1H), 6.31 (s, 1H), 5.81-5.60 (m, 1H), 5.44-5.22 (m, 1H), 4.47 (d, J=6.3 Hz, 2H) 3.73 (s, 2H), 3.67 (s, 3H), 3.55 (s, 1H), 3.39-3.35 (m, 2H), 3.17 (s, 3H), 3.16 (s, 3H), 0.79 (t, J=7.4 Hz, 3H), 0.74 (t, J=7.1 Hz, 3H); ESI MS m/z=1565 [M+H]$^+$; HPLC (Method A, 254 nm) 34.0% (AUC), $t_R$=11.08 min.

Example 22

Preparation of (3aR,4R,5S,5aR,10bR)-methyl 3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-4-((1-(5-oxo-5-(perfluorophenoxy)pentyl)silinan-1-yl)oxy)-3a,3a1,4,5,5a,6,11,12-octahydro-1H-indolizino[8,1-cd]carbazole-5-carboxylate

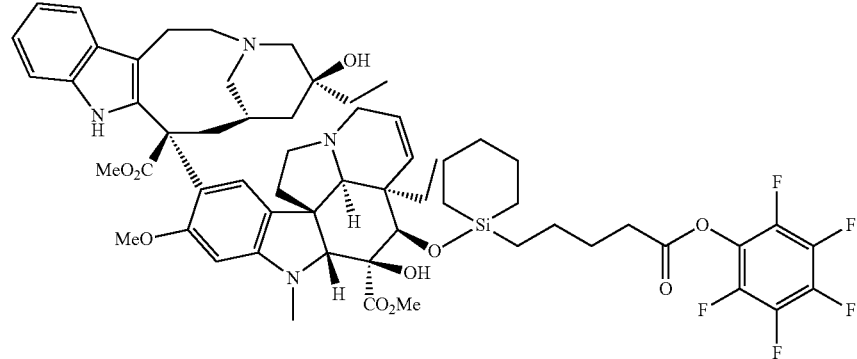

Step A. A solution of (3aR,4R,5S,5aR,10bR)-methyl 4-((1-(5-(benzyloxy)-5-oxopentyl)silinan-1-yl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a1,4,5,5a,6,11,12-octahydro-1H-indolizino[8,1-cd]carbazole-5-carboxylate (100 mg, 0.095 mmol) in ethyl acetate (18 mL) was purged with nitrogen for 10 minutes. Palladium on carbon (75 mg, 10% Pd/C, 50% water) was added and the mixture was purged for an additional 2 minutes. The reaction was capped with a hydrogen balloon and stirred for 2.5 hours at room temperature. The reaction was purged with nitrogen and N, N-diisopropylethylamine (0.2 mL) was added. The mixture was filtered through Celite and the filter cake was rinsed with ethyl acetate and methanol. The filtrate was concentrated in vacuo to afford 5-(1-(((3aR,4R,5S,5aR,10bR)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-5-(methoxycarbonyl)-6-methyl-3a,3a1,4,5,5a,6,11,12-octahydro-1H-indolizino[8,1-cd]carbazol-4-yl)oxy)silinan-1-yl)pentanoic acid (94 mg, 100% yield) as a tan solid: $^1$H NMR (500 MHz, CDCl$_3$) δ 8.90 (br s, 1H), 7.49 (d, J=8.9 Hz, 1H), 7.31 (d, J=8.0 Hz, 1H), 7.15 (td, J=7.1, 0.9 Hz, 1H), 7.05 (ddd, J=7.8, 7.1, 0.8 Hz, 1H), 6.61 (s, 1H), 6.05 (s, 1H), 5.79 (dd, J=10.3, 4.2 Hz, 1H), 5.50 (d, J=10.3 Hz, 1H), 3.98 (dd, J=4.5, 3.4 Hz, 1H), 3.78 (s, 3H), 3.76 (s, 3H), 3.65 (s, 3H), 3.62 (s, 2H), 3.48 (d, J=13.1 Hz, 1H), 3.39-3.21 (m, 3H), 3.18-3.10 (m, 2H), 2.84-2.65 (m, 4H), 2.73 (s, 3H), 2.41-2.32 (m, 3H), 2.30-2.17 (m, 3H), 2.00-1.86 (m, 4H), 1.73-1.51 (m, 8H), 1.42-1.24 (m, 13H), 1.21-1.12 (m, 2H), 1.06-0.96 (m, 4H), 0.94-0.86 (m, 4H), 0.79-0.72 (m, 7H), 0.67-0.54 (m, 3H); ESI MS m/z=967 [M+H]$^+$; HPLC (Method A, 254 nm) 91.1% (AUC), $t_R$=12.33 min.

Step B. To a solution of 5-(1-(((3aR,4R,5S,5aR,10bR)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-5-(methoxycarbonyl)-6-methyl-3a,3a1,4,5,5a,6,11,12-octahydro-1H-indolizino[8,1-cd]carbazol-4-yl)oxy)silinan-1-yl)pentanoic acid (35 mg, 0.036 mmol) in methylene chloride (1 mL) at 0° C. was added N, N-diisopropylethylamine (0.031 mL, 0.18 mmoL), DMAP (~1 mg), pentafluorophenol (13 mg, 0.072 mmol), and EDCI (10 mg, 0.054 mmol). The reaction was warmed to room temperature and stirred for 18 hours. The reaction mixture was diluted with ethyl acetate (30 mL) and washed successively with water, saturated sodium bicarbonate, and brine. The organic layer was dried with sodium sulfate, filtered, and concentrated in vacuo to afford crude (3aR,4R,5S,5aR,10bR)-methyl 3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-4-((1-(5-oxo-5-(perfluorophenoxy)pentyl)silinan-1-yl)oxy)-3a,3a1,4,5,5a,6,11,12-octahydro-1H-indolizino[8,1-cd]carbazole-5-carboxylate (60 mg, 150% of theoretical yield) which was used directly in the next step: $^1$H NMR (500 MHz, CDCl$_3$) δ (select peaks) 8.16 (br s, 1H), 8.12 (d, J=7.1 Hz, 1H), 7.46 (dd, J=8.0, 1.5 Hz, 1H), 7.18-7.12 (m, 2H), 7.08 (dd, J=6.8, 6.6 Hz, 1H), 6.61 (d, J=7.2 Hz, 1H), 6.56 (s, 1H), 6.10 (s, 1H), 5.78 (d, J=10.1, 4.3 Hz, 1H), 5.45 (d, J=10.2 Hz, 1H), 4.16 (s, 1H), 3.98-3.87 (m, 2H), 3.79 (s, 3H), 3.78 (s, 3H), 3.63 (s, 3H), 3.58 (dd, J=6.7, 6.6 Hz, 2H), 3.50 (d, J=14.4 Hz, 1H), 3.40 (dd, J=14.2, 10.3 Hz, 1H), 3.32-3.28 (*m, 1H), 3.25-3.16 (m, 3H), 3.14 (s, 3H), 2.90-2.88 (m, 2H), 2.79 (d, J=6.3 Hz, 1H), 2.71 (s, 3H), 2.69-2.65 (m, 3H), 2.50 (dd, J=13.7, 4.3 Hz, 1H), 2.42-2.34 (m, 2H), 2.07-2.01 (m, 4H), 1.84-1.77 (m, 2H), 1.71 (td, J=13.3, 5.6 Hz, 1H); ESI MS m/z=1133 [M+H]$^+$.

Example 23

Preparation of (3aR,4R,5S,5aR,10bR)-methyl 4-((1-(5-((2,5-dioxopyrrolidin-1-yl)oxy)-5-oxopentyl)silinan-1-yl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a1,4,5,5a,6,11,12-octahydro-1H-indolizino[8,1-cd]carbazole-5-carboxylate

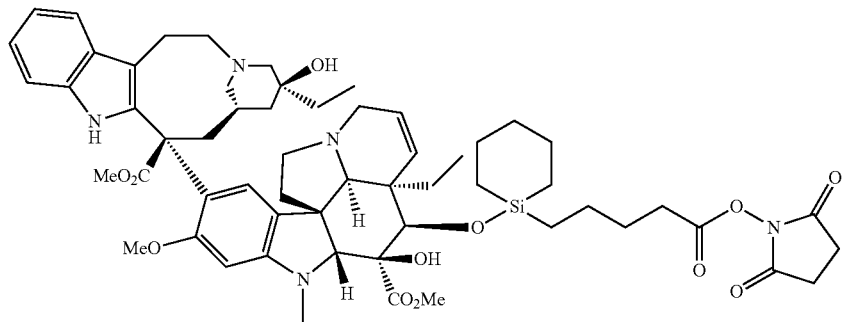

To a solution of 5-(1-(((3aR,4R,5S,5aR,10bR)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-5-(methoxycarbonyl)-6-methyl-3a,3a1,4,5,5a,6,11,12-octahydro-1H-indolizino[8,1-cd]carbazol-4-yl)oxy)silinan-1-yl)pentanoic acid (100 mg, 0.10 mmol) in methylene chloride (2 mL) at 0° C. under nitrogen was added N, N-diisopropylethylamine (0.09 mL, 0.5 mmoL), DMAP (~1 mg), N-hydroxysuccinimide (18 mg, 0.15 mmol), and EDCI (18 mg, 0.15 mmol). The reaction was warmed to room temperature and stirred for 17 hours. The reaction mixture was diluted with ethyl acetate (30 mL) and washed successively with water, saturated sodium bicarbonate, and brine. The organic layer was dried with sodium sulfate, filtered, and concentrated in vacuo to afford crude (3aR,4R,5S,5aR,10bR)-methyl 4-((1-(5-((2,5-dioxopyrrolidin-1-yl)oxy)-5-oxopentyl)silinan-1-yl)oxy)-3a-ethyl-9-((5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a1,4,5,5a,6,11,12-octahydro-1H-indolizino[8,1-cd]carbazole-5-carboxylate (146 mg, 140% of theoretical) which was used directly in the next step: $^1$H NMR (500 MHz, CDCl$_3$) δ (select peaks) 8.17 (br s, 1H), 8.14 (d, J=6.0 Hz, 1H), 7.51 (d, J=7.9 Hz, 1H), 7.36-7.32 (m, 1H), 7.20-7.15 (m, 2H), 7.13-7.08 (m, 1H), 6.60-6.58 (m, 2H), 6.12-6.08 (m, 1H), 5.81-5.77 (m, 1H), 5.47 (d, J=10.1 Hz, 1H), 3.92 (dd, J=14.4, 13.8 Hz, 2H), 3.79 (s, 3H), 3.78 (s, 3H), 3.62 (s, 3H), 3.70-3.57 (m, 3H), 3.44 (d, J=14.0 Hz, 2H), 3.37-3.22 (m, 4H), 3.16 (d, J=13.3 Hz, 2H), 3.12 (s, 3H), 2.87-2.76 (m, 5H), 2.71 (s, 4H), 2.46-2.17 (m, 5H), 2.04 (s, 3H); ESI MS m/z=1064 [M+H]$^+$.

Example 24

Cleavage Studies on Silyl Conjugates

To study the release properties of the silyl conjugates, the conjugates were subject to hydrolysis conditions at both pH 7.4 and pH 4.5 to simulate blood and endosomes/lysosome environments, respectively.

The benzyl ester intermediates from Example 11 (step A), Example 12, Example 13, Example 14 (step A), and Example 15 were each dissolved in a 1:1 mixture of THF:0.05 M acetate buffer (pH 4.5) and heated to 37° C. with stirring. The mixture was analyzed with HPLC at T=1, 2, 3, 4, 5, 7 and 24 hours via Method B (see General Procedures in Example 1). Aliquots were quenched in a 1:1 acetonitrile:triethylamine solvent mixture to halt the hydrolysis reaction and allowed to stand up to 48 hours before HPLC analysis. Control stability studies on the benzyl ester intermediate from Example 12 in 1:1 acetonitrile:triethylamine reveal no evidence of hydrolysis over a 48 hour period, demonstrating the triethylamine quench was effective at halting the hydrolysis reaction during the period of analysis. A range of different hydrolysis rates were observed over a 24 hour time period for the various derivatives, thereby demonstrating the tunability of the silicon ether-based linker technology (see FIG. 1).

Figure 2:
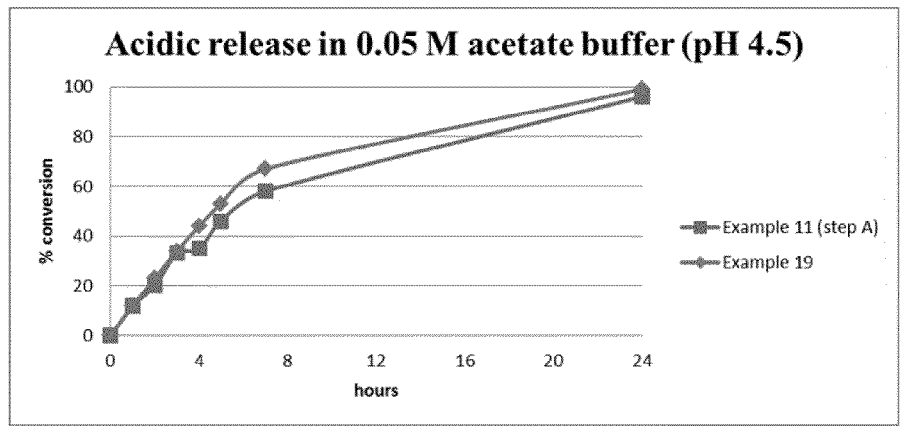
FIG. 2 is a graph showing a hydrolysis rate comparison of the compound of Example 19 with that of the corresponding compound of Example 11 (step A).
Figure 2:
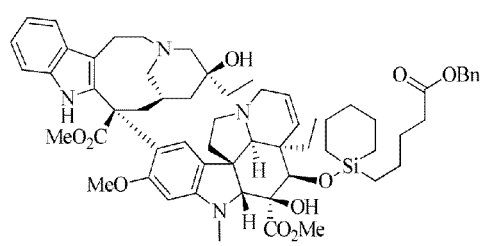
Figure 2:
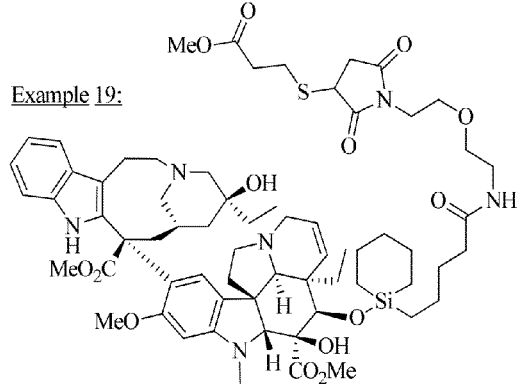

Example 12 and Example 15 were dissolved in THF:0.01 M PBS buffer (pH 7.4) and heated to 37° C. with stirring for over 20 hours. No evidence of hydrolysis (e.g. parent vinca) was observed, predicting good stability for the conjugate at pH 7.4. Additionally, Example 11 was trapped with methyl-3-mercaptopropionate to approximate a bioconjugate. The resulting compound, Example 19, was subjected to hydrolysis conditions and found to undergo parent vinca release at a rate comparable to the corresponding benzyl ester from Example 11 (step A) (see FIG. 2), supporting that the hydrolysis rates for each benzyl ester fragment can approximate that of the corresponding model bioconjugate.

When Example 19 was treated at pH 7.4 (as above for Example 12 and 15), no desilylation was observed after 24 hours.

Example 25

Cell Proliferation Studies

Cell Lines and Maintenance

Folate receptor (FR)-positive KB cells (Human) from European Collection of Cell Cultures (ECACC) [Catalogue #94050408] or FR-negative human lung carcinoma A549 cells from American Type Culture Collection (ATCC) [Catalogue # CCL-185] were maintained in T75 flasks in folic acid-free RPMI 1640 medium (Invitrogen, catalogue no. 27016021) containing 10% fetal bovine serum (FBS; Invitrogen, catalogue no. 16140-071) and penicillin/streptomycin (Invitrogen, catalogue no. 15140-122) at 37° C., 5% $CO_2$.

Cell Proliferation Assay

Cells were harvested from their maintenance cultures and seeded in 96-well plates at a density of 10000 cells per well in 100 μL folic acid-free RPMI 1640 medium and incubated at 37° C., 5% $CO_2$ for 20-24 hours. Thirty minutes prior to compound treatment, spent medium was removed and replaced with 100 μL fresh folic acid-free RPMI 1640 medium either as such, or supplemented with 100 μmol/L folic acid. The test compounds were diluted to three times their desired final concentrations in the culture medium from their DMSO stocks. Fifty microliters of the compound solutions in medium or just the DMSO in medium were then added to the wells and the cells were incubated for 2 hours at 37° C. Following compound treatment, the cells were washed thrice with 100 μL medium and incubated with 180 μL fresh medium for 72 hours. To assess cell viability, 20 μL of PrestoBlue reagent (Invitrogen, catalogue # A-13261) was added to the wells and the plates were further incubated for 1 hour at 37° C. The PrestoBlue reagent contains a cell-permeant dye, resazurin, which is blue in color and virtually nonfluorescent. When added to cells, it is reduced by the mitochondrial enzymes in viable cells to red, highly fluorescent resorufin. Resazurin reduction is proportional to the number of metabolically active cells and therefore can be measured quantitatively. Following incubation with the PrestoBlue reagent for 1 hour, fluorescence corresponding to the resorufin dye was read on a Synergy 4 multimode microplate reader (Biotek Instruments) with the excitation and emission wavelengths set at 540 nm and 590 nm respectively. The data was analysed using XLFit and the percentage inhibition of cell proliferation was calculated.

Preparation of Control Compound Z—(S)-2-(4-(((2-amino-4-hydroxypteridin-6-yl)methyl)amino)benzamido)-20-(1-hydroxysilinan-1-yl)-5,16-dioxo-9,12-dioxa-6,15-diazaicosan-1-oic acid triethylammonium salt Compound Z, the hydrolytic cleavage product, was prepared as a control compound in the cellular assays as set forth in Scheme 11 below:

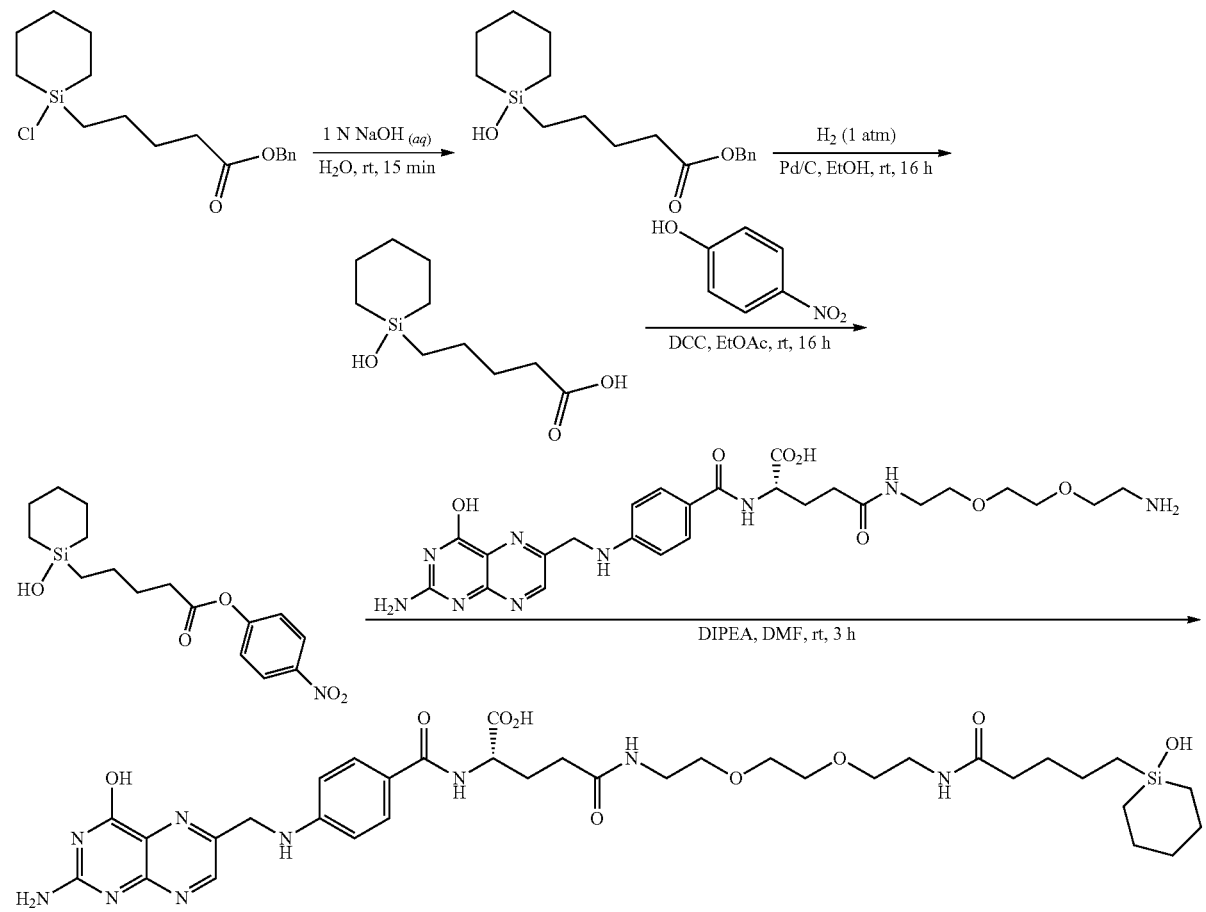

Step A. To crude benzyl 5-(1-chlorosilinan-1-yl)pentanoate (400 mg, 1.23 mmol) 1 N aqueous sodium hydroxide (0.3 mL, 0.3 mmol) was added and the contents sonicated for 10 minutes. After this time, the reaction was diluted with water (1 mL) and sonicated for 5 minutes. After this time, the reaction mixture was diluted further with water (10 mL) and ethyl acetate (25 mL). The organic layer was separated from the aqueous layer, and the aqueous layer was back extracted with ethyl acetate (2×25 mL). The combined organics were dried over sodium sulfate, filtered, and the filtrate concentrated under reduced pressure. The residue obtained was purified by silica gel column chromatography eluting with hexanes to 1:4 ethyl acetate/hexanes over 40 minutes to afford benzyl 5-(1-hydroxysilinan-1-yl)pentanoate (209 mg, 55%) as a colorless oil: $^1$H NMR (300 MHz, CDCl$_3$) δ 7.38-7.27 (m, 5H), 5.10 (s, 2H), 2.74 (bs, 1H), 2.39-2.29 (m, 2H), 1.76-1.57 (m, 6H), 1.48-1.30 (m, 4H), 0.72-0.47 (m, 6H).

Step B. To benzyl 5-(1-hydroxysilinan-1-yl)pentanoate (205 mg, 0.669 mmol) in ethanol (6 mL), palladium on activated carbon (10%, wet, 41 mg) was added. The reaction was stirred under hydrogen (1 atm) at room temperature for 16 hours. After this time, the reaction was filtered through Celite® and the filter cake washed with methanol. The filtrate was concentrated under reduced pressure to afford 5-(1-hydroxysilinan-1-yl)pentanoic acid (140 mg, 97%) as a colorless oil. $^1$H NMR (500 MHz, CDCl$_3$) δ Exchangeable protons not observed (2H), 2.38-2.32 (m, 2H), 1.78-1.61 (m, 6H), 1.48-1.31 (m, 4H), 0.80-0.54 (m, 6H); ESI MS m/z=215 [M−H]$^−$.

Step C. To 5-(1-hydroxysilinan-1-yl)pentanoic acid (130 mg, 0.601 mmol) in ethyl acetate (5 mL), N,N′-dicyclohexylcarbodiimide (186 mg, 0.901 mmol) was added. The reaction was stirred under nitrogen at ambient temperature for 30 minutes. After this time, 4-nitrophenol (100 mg, 0.719 mmol) was added, and the reaction was stirred for 16 hours at ambient temperature. After this time, the reaction was filtered to remove any solids, the filter cake was washed with ethyl acetate, and the filtrate was concentrated under reduced pressure. The residue obtained was purified by silica gel column chromatography eluting with hexanes to 1:3 ethyl acetate/hexanes to afford 4-nitrophenyl 5-(1-hydroxysilinan-1-yl)pentanoate (106 mg, 52%) as a colorless oil. $^1$H NMR (500 MHz, CDCl$_3$) δ 8.26 (dt, J=9.0, 2.5 Hz, 2H), 7.27 (dt, J=9.0, 2.5 Hz, 2H), 2.61 (t, J=7.5 Hz, 2H), 1.84-1.78 (m, 2H), 1.76-1.67 (m, 4H), 1.56-1.44 (m, 4H), 1.40-1.33 (m, 1H), 0.75-0.63 (m, 6H).

Step D. To (5)-2-(4-(((2-amino-4-hydroxypteridin-6-yl)methyl)amino)benzamido)-5-((2-(2-(2-aminoethoxy)ethoxy)ethyl)amino)-5-oxopentanoic acid, trifluoroacetic acid salt (32 mg, 0.048 mmol) and N,N-diisopropylethylamine (0.06 mL, 0.34 mmol) in N,N-dimethylformamide (1 mL), 4-nitrophenyl 5-(1-hydroxysilinan-1-yl)pentanoate (19 mg, 0.056 mmol) in N,N-dimethylformamide (2 mL) was added. The reaction was stirred at ambient temperature for 7 hours. After this time, the solvent was removed by azeotrope with water (4×4 mL) under reduced pressure. The residue obtained was diluted in water (2 mL) and extracted with ethyl acetate (3 mL ×3). The organic layers were removed and the aqueous layer concentrated under reduced pressure. The resulting solid was washed with water (3×6 mL), filtered, and then dissolved in water (8 mL) containing 0.1% triethylamine. The resulting solution was purified by reverse phase column chromatography eluting with 5:95 acetonitrile/water (with 0.1% triethylamine) to acetonitrile over 15 minutes to afford (10 mg, 24%) as a light yellow solid. $^1$H NMR (500 MHz, DMSO-d$_6$) δ 11.58 (vbs, 1H), 8.63 (s, 1H), 8.04 (d, J=3.5 Hz, 1H), 7.91 (t, J=5.5 Hz, 1H), 7.82 (t, J=5.5 Hz, 1H), 7.62 (d, J=9.0 Hz, 2H), 7.07-6.73 (vbs, 1H), 6.90 (t, J=6.0 Hz, 1H), 6.64 (d, J=9.0 Hz, 2H), 5.33 (bs, 1H), 4.47 (d, J=6.0 Hz, 2H), 4.20-4.19 (m, 1H), 3.47 (s, 4H), 3.38-3.35 (m, 4H), 3.18-3.14 (m, 4H), 2.58-2.57 (m, 4H), 2.16 (t, J=7.5 Hz, 2H), 2.08-1.98 (m, 3H), 1.91-1.87 (m, 1H), 1.70-1.62 (m, 2H), 1.57-1.45 (m, 4H), 1.37-1.25 (m, 4H), 0.98 (t, J=7.0 Hz, 7H), 0.55-0.46 (m, 6H), exchangeable proton not observed (1H); ESI MS m/z=768 [M−H]$^−$; HPLC (254 nm) 98.5% (AUC), $t_R$=12.18 min.

Results

The results from the cell proliferation studies are shown in Table 1, below:

TABLE 1

Inhibition of Cell Growth by the PrestoBlue Method[a]

| ID | Incubation (h) | A549 cells (FR negative) | | KB cells (FR positive) | |
|---|---|---|---|---|---|
| | | No FA | 100 μM FA | No FA | 100 μM FA |
| Example 20 | 2 | >10 (20%) | >10 (44%) | 3.5 | 4.2 |
| Example 21 | | >10 (8%) | >10 (40%) | 4.1 | 6.0 |
| Compound Z | | >10 (7%) | >10 (9%) | >10 (≤0%) | >10 (1%) |
| 4-desacetylvinblastine | | 4.6[b] | | 0.045 | |
| Example 20 | 4 | >10 (46%) | 6.6 | 2.6 | 3.4 |
| Example 21 | | >10 (24%) | 8.6 | 3.1 | 4.0 |
| Compound Z | | >10 (≤0%) | >10 (≤0%) | >10 (≤0%) | >10 (≤0%) |
| 4-desacetylvinblastine | | 0.633 | | 0.010 | |
| Example 20 | 8 | 6.7 | 4.1 | 1.8 | 3.1 |
| Example 21 | | >10 (47%) | 5.3 | 2.3 | 3.1 |
| Compound Z | | >10 (≤0%) | >10 (≤0%) | >10 (≤0%) | >10 (≤0%) |
| 4-desacetylvinblastine | | 0.129 | | 0.002 | |
| Example 20 | 16 | 1.4 | 1.4 | 0.3 | 1.5 |
| Example 21 | | 4.4 | 1.8 | 1.5 | 1.7 |
| Compound Z | | >10 (≤0%) | >10 (3.5%) | >10 (1%) | >10 (2%) |
| 4-desacetylvinblastine | | 0.057 | | 0.003 | |

[a]IC$_{50}$ values reported in μM. Percentage inhibition at the highest concentration tested (10 μM) is given in parentheses where the IC$_{50}$ values could not be generated.
[b]60% maximum inhibition achieved.

FA = folic acid.

Incubation is the time test article was incubated with the cells prior to a 4x wash with fresh media.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A conjugate compound of formula (I):

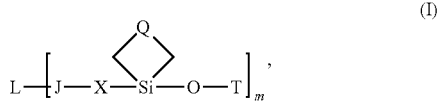

(I)

wherein
L is a cell-targeting ligand;
T is a therapeutic agent, with the proviso that T is not CAS Registry No. 115834-23-6(SF2446A1) or derivatives or analogues thereof;
J is a linker group;
X is independently selected from the group consisting of:
(1) a bond;
(2) O;
(3)

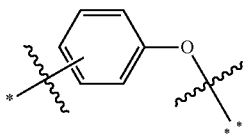

which is independently and optionally substituted from 1 to 2 times with $R^8$, wherein the wavy lines indicate point of attachment sites and * is the point of attachment to J and ** is the point of attachment to Si; and
(4)

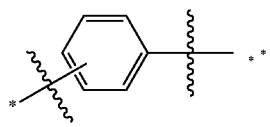

which is independently and optionally substituted from 1 to 2 times with $R^8$, wherein the wavy lines indicate point of attachment sites and * is the point of attachment to J and ** is the point of attachment to Si;
Q is $-(CH_2)_n-$, $-CH_2CHR^1CH_2-$, $-CH_2CR^5R^6CH_2-$, $-CH_2CHR^1CH_2CH_2-$, $-CH_2CH_2CHR^1CH_2CH_2-$, $-CH_2X^1CH_2-$, or $-CH_2CH_2X^1CH_2CH_2-$;
$R^1$ is $C_{1-6}$ alkyl, aryl, heteroaryl, $OR^5$, $NR^5R^6$, or $-N(COR^2)R^7$, each of which is optionally substituted with $R^8$;
$R^2$ is H, $C_{1-6}$ alkyl, $C_{3-6}$ cycloalkyl, aryl, or heteroaryl, each of which is optionally substituted with $R^8$;
$R^3$ is H, $C_{1-6}$ alkyl, $C_{3-6}$ cycloalkyl, or $-COR^4$, each of which is optionally substituted with $R^8$;
$R^4$ is H, $C_{1-6}$ alkyl, or $C_{3-6}$ cycloalkyl, each of which is optionally substituted with $R^8$,
$R^5$ is H or $C_{1-6}$ alkyl optionally substituted with $R^8$;
$R^6$ is H or $C_{1-6}$ alkyl optionally substituted with $R^8$; or
$R^5$ and $R^6$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy;
$R^7$ is H, $C_{1-6}$ alkyl, $C_{3-6}$ cycloalkyl, aryl, or heteroaryl, each of which is optionally substituted with $R^8$;
$R^8$ is H, $NO_2$, CN, halogen, oxo, $C_{1-6}$ alkyl, $C_{1-6}$ haloalkyl, $C_{1-6}$ hydroxyalkyl, $C_{1-6}$ alkoxyalkyl, $C_{3-6}$ cycloalkyl, $C_{4-7}$ cycloalkylalkyl, aryl, heteroaryl, $COOR^9$, $COR^9$, $C(O)NR^9R^{10}$, $COONR^9R^{10}$, $SO_2R^9$, $SO_2NR^9R^{10}$, or $OR^9$;
$R^9$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;
$R^{10}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy; or
$R^9$ and $R^{10}$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy;
$X^1$ is O, S, SO, $SO_2$, or $NR^3$;
n is 1 to 5; and
m is 1 to 8.

2. The conjugate compound according to claim 1, wherein J is $-Z-Y^2-C(O)-Y^1-$;
Z is

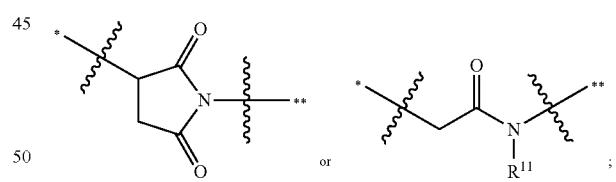

wherein the wavy lines indicate point of attachment sites and * is the point of attachment to L and ** is the point of attachment to $Y^2$;
$Y^1$ is $C_{1-6}$ alkylene or $-(X^2-CH_2-CH_2)_1-$, each of which is optionally substituted with $R^8$;
$Y^2$ is $C_{1-6}$ alkylene or $-(CH_2CH_2(X^3))_q-$, each of which is optionally substituted with $R^8$;
$X^2$ is independently selected from the group consisting of:
(1) a bond;
(2) $(CH_2)_k$;
(3) O; and
(4) $NR^{12}$;
$X^3$ is independently selected from the group consisting of:
(1) a bond;
(2) $(CH_2)_k$;

(3) O; and
(4) NR$^{12}$;
R$^{11}$ is H, C$_{1-6}$ alkyl, C$_{1-6}$ hydroxyalkyl, C$_{3-6}$ cycloalkyl, C$_{4-7}$ cycloalkylalkyl, aryl, or heteroaryl, each of which is optionally substituted from 1 to 3 times with halogen, hydroxyl, cyano, oxo, C$_1$-C$_4$ alkyl, C$_1$-C$_4$ haloalkyl, or C$_1$-C$_4$ alkoxy;
R$^{12}$ is H, C$_{1-6}$ alkyl, C$_{1-6}$ haloalkyl, C$_{1-6}$ alkoxyalkyl, C$_{3-6}$ cycloalkyl, C$_{4-7}$ cycloalkylalkyl, or C$_{1-6}$ hydroxyalkyl;
k is 1 to 3;
l is 1 to 10; and
q is 1 to 10.

3. The conjugate compound according to claim 1, wherein J is —Z—Y$^3$—;
Z is

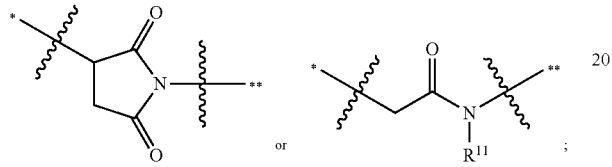

wherein the wavy lines indicate point of attachment sites and * is the point of attachment to L and ** is the point of attachment to Y$^3$;
Y$^3$ is selected from the group consisting of C$_{1-6}$ alkylene, C$_3$-C$_8$ carbocyclyl, O(CH$_2$)$_r$, arylene, O(CH$_2$)$_r$-arylene, -arylene-(CH$_2$)$_r$—, (CH$_2$)$_r$—(C$_{3-8}$ carbocyclyl), —(C$_{3-8}$ carbocyclyl)-(CH$_2$)$_r$, C$_{3-8}$ heterocyclyl, (CH$_2$)$_r$—(C$_{3-8}$ heterocyclyl), —(C$_{3-8}$ heterocyclyl)-(CH$_2$)$_r$, —((X$^4$)(X$^5$)(CH$_2$)$_r$(X$^6$)(CH$_2$)$_r$)$_s$—, and —((X$^4$)(X$^5$)(CH$_2$)$_r$(X$^6$)(X$^7$)(CH$_2$)$_r$)$_s$—, each of which is optionally substituted with R$^8$;
X$^4$, X$^5$, X$^6$, and X$^7$ are each independently selected from the group consisting of a bond, (CH$_2$)$_k$, O, C(O), S, NR$^{19}$, C(O)O, and C(O)NR$^{19}$;
R$^{11}$ is H, C$_{1-6}$ alkyl, C$_{1-6}$ hydroxyalkyl, C$_{3-6}$ cycloalkyl, C$_{4-7}$ cycloalkylalkyl, aryl, or heteroaryl, each of which is optionally substituted from 1 to 3 times with halogen, hydroxyl, cyano, oxo, C$_1$-C$_4$ alkyl, C$_1$-C$_4$ haloalkyl, or C$_1$-C$_4$ alkoxy;
R$^{19}$ is H, C$_{1-6}$ alkyl, C$_{1-6}$ haloalkyl, C$_{1-6}$ alkoxyalkyl, C$_{3-6}$ cycloalkyl, C$_{4-7}$ cycloalkylalkyl, or C$_{1-6}$ hydroxyalkyl;
each r is 0 to 16; and
s is 1 to 10.

4. The conjugate compound according to claim 1, wherein Q is —(CH$_2$)$_n$— and n is 1 to 5.

5. The conjugate compound according to claim 1, wherein J further comprises a thiol-containing spacer.

6. The conjugate compound according to claim 1, wherein L is a protein, a peptide, an amino acid, a receptor ligand, a hormone, or a growth factor.

7. The conjugate compound according to claim 6, wherein L is selected from the group consisting of an antibody, an antibody fragment, scFv-Fc, minibody, diabody, scFv, folic acid, bombesin, EDG, transferrin, gastrin, gastrin-releasing peptide, platelet-derived growth factor, IL-2, IL-6, TFG-alpha, TFG-beta, VGF, insulin, and insulin-like growth factors I and II.

8. The conjugate compound according to claim 6, wherein L is an antibody which binds to one or more tumor-associated antigens or cell-surface receptors selected from (1)-(35):
(1) BMPR1B (bone morphogenetic protein receptor-type IB, Genbank Accession No. NM$_{13}$ 001203);
(2) E16 (LAT1, SLC7A5, Genbank Accession No. NM_003486);
(3) STEAP1 (six transmembrane epithelial antigen of prostate, Genbank Accession No. NM_012449);
(4) 0772P (CA125, MUC16, Genbank Accession No. AF361486);
(5) MPF (MPF, MSLN, SMR, megakaryocyte potentiating factor, mesothelin, Genbank Accession No. NM_005823);
(6) Napi3b (NAPI-3B, NPTIIb, SLC34A2, solute carrier family 34 (sodium phosphate), member 2, type II sodium-dependent phosphate transporter 3b, Genbank Accession No. NM_006424);
(7) Sema 5b (FLJ10372, KIAA1445, Mm.42015, SEMA5B, SEMAG, Semaphorin5bHlog, sema domain, seven thrombospondin repeats (type 1 and type 1-like), transmembrane domain (TM) and short cytoplasmic domain, (semaphorin) 5B, Genbank Accession No. AB040878);
(8) PSCA hlg (2700050C12Rik, C530008O16Rik, RIKEN cDNA 2700050C12, RIKEN cDNA 2700050C12 gene, Genbank Accession No. AY358628);
(9) ETBR (Endothelin type B receptor, Genbank Accession No. AY275463);
(10) MSG783 (RNF124, hypotheticalproteinFLJ20315, Genbank Accession No. NM_017763);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank Accession No. AF455138);
(12) TrpM4 (BR22450, FLJ20041, TRPM4, TRPM4B, transient receptor potential cation channel, subfamily M, member 4, Genbank Accession No. NM_017636);
(13) CRIPTO (CR, CR1, CRGF, CRIPTO, TDGF1, teratocarcinoma-derived growth factor, Genbank Accession No. NP_003203 or NM_003212);
(14) CD21 (CR2 (Complement receptor 2) or C3DR (C3d/Epstein Barr virus receptor) or Hs.73792 Genbank Accession No. M26004);
(15) CD79b (CD79B, CD79β IGb (immunoglobulin-associated beta), B29, Genbank Accession No. NM_000626);
(16) FcRH2 (IFGP4, IRTA4, SPAP1A (SH2 domain containing phosphatase anchor protein 1a), SPAP1B, SPAP1C, Genbank Accession No. NM_030764);
(17) HER2 (Genbank Accession No. M11730);
(18) NCA (Genbank Accession No. M18728);
(19) MDP (Genbank Accession No. BC017023);
(20) IL20Rα (Genbank Accession No. AF184971);
(21) Brevican (Genbank Accession No. AF229053);
(22) Ephb2R (Genbank Accession No. NM_004442);
(23) ASLG659 (Genbank Accession No. AX092328);
(24) PSCA (Genbank Accession No. AJ297436);
(25) GEDA (Genbank Accession No. AY260763);
(26) BAFF-R (B cell-activating factor receptor, BLyS receptor 3, BR3, Genbank Accession No. NP_443177.1);
(27) CD22 (B-cell receptor CD22-B isoform, Genbank Accession No. NP-001762.1);
(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation, Genbank Accession No. NP_001774.1);

(29) CXCR5 (Burkitt's lymphoma receptor 1, a G protein-coupled receptor that is activated by the CXCL13 chemokine, functions in lymphocyte migration and humoral defense, plays a role in HIV -2 infection and perhaps development of AIDS, lymphoma, myeloma, and leukemia, Genbank Accession No. NP_001707.1);

(30) HLA-DOB (Beta subunit of MHC class II molecule (Ia antigen) that binds peptides and presents them to CD4+ T lymphocytes, Genbank Accession No. NP_002111.1);

(31) P2X5 (Purinergic receptor P2X ligand-gated ion channel 5, an ion channel gated by extracellular ATP, Genbank Accession No. NP_002552.2);

(32) CD72 (B-cell differentiation antigen CD72, Lyb-2, Genbank Accession No. NP_001773.1);

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis, Genbank Accession No. NP_005573.1);

(34) FCRH1 (Fc receptor-like protein 1, a putative receptor for the immunoglobulin Fc domain that contains C2 type Ig-like and ITAM domains, Genbank Accession No. NP_443170.1); and

(35) IRTA2 (Immunoglobulin superfamily receptor translocation associated 2, a putative immunoreceptor with possible roles in B cell development and lymphomagenesis; deregulation of the gene by translocation occurs in some B cell malignancies, Genbank Accession No. NP_112571.1).

9. The conjugate compound according to claim 6, wherein L is folic acid.

10. The conjugate compound according to claim 6, wherein L is epidermal growth factor.

11. The conjugate compound according to claim 1, wherein T is a hydroxyl-containing drug moiety.

12. The conjugate compound according to claim 1, wherein T is an anticancer agent selected from the group consisting of N8-acetyl spermidine, actinomycin, 9-amino camptothecin, aminopterin, anguidine, anthracycline, auristatin, bleomycin, calicheamycin, camptothecin, carminomycin, CC-1065, clofaribine, 1-(2-chloroethyl)-1,2-dimethanesulfonyl hydrazide, cyclopropabenzindol-4-one (CBI), cytarabine, cytosine arabinoside, daunorubicin, dichloromethotrexate, n-(5,5-diacetoxy-pentyl) doxorubicin, 1,8-dihydroxy-bicycle[7.3.1] trideca-4-9-diene-2,6-diyne-13-one, difluoronucleosides, doxorubicin, duocarmycin, epirubicin, esperamicin, etoposide, 5-fluorouracil, irinotecan, leurosideine, leurosine, maytansine, melphalan, 6-mercaptopurine, methopterin, methotrexate, mitomycin A, mitomycin C, morpholine-doxorubicin, butyric acid, cisplatin, diacetoxypentyldoxorubicin, maytansinol, capecitabine, leuprolide, bicalutamide, goserelin, 17-AAG, 17-DMAG, des-acetyl vinblastine, nemorubicin, podophyllotoxin, podophyllotoxin derivatives, retinoic acid, saporin, tallysomycin, vinblastine, vincristine, vindesine, taxane, taxol, paclitaxel, taxotere, docetaxel, taxotere retinoic acid, and isomers, salt forms, analogues, and derivatives thereof.

13. The conjugate compound according to claim 1 having the formula:

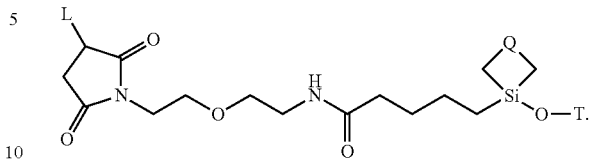

14. The conjugate compound according to claim 1 having the formula:

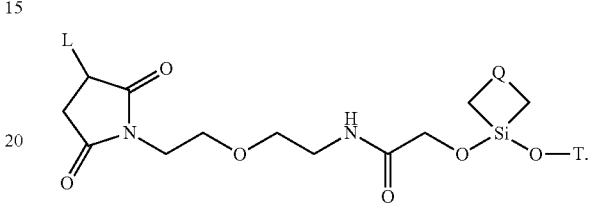

15. A pharmaceutical composition comprising:
    a pharmaceutically acceptable carrier and the conjugate compound according to claim 1.

16. A method of therapeutically treating carcinomas of the lung in a subject in need thereof comprising:
    selecting a cancer subject in need of therapeutic treatment of carcinoma of the lung, and
    administering to the selected subject a therapeutically acceptable amount of a conjugate compound according to claim 1.

17. A conjugate compound of formula (III):

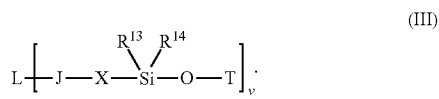

(III)

wherein
L is a cell-targeting ligand;
T is a therapeutic agent, with the proviso that T is not CAS Registry No. 115834-23-6 (SF2446A1) or derivatives or analogues thereof;
J is a linker group, with the proviso that when X is a bond, J cannot directly bond to the silicon atom with an O, NH, N—CH$_3$, S, or carboxyl and forms a hydrolytically stable carbon bond with the silicon atom;
X is independently selected from the group consisting of:
(1) a bond;
(2)

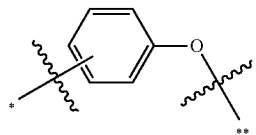

which is independently and optionally substituted from 1 to 2 times with $R^{15}$, wherein the wavy lines indicate point of attachment sites and * is the point of attachment to J and ** is the point of attachment to Si; and (3)

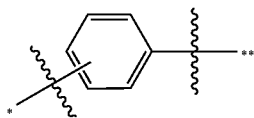

which is independently and optionally substituted from 1 to 2 times with $R^{15}$, wherein the wavy lines indicate point of attachment sites and * is the point of attachment to J and ** is the point of attachment to Si;

$R^{13}$ and $R^{14}$ are each independently selected from the group consisting of $C_{1-6}$ alkyl, $C_{3-6}$ cycloalkyl, aryl, and heteroaryl, each of which is optionally substituted with $R^{16}$;

$R^{15}$ is H, $C_{1-6}$ alkyl, $C_{1-6}$ haloalkyl, $C_{1-6}$ hydroxyalkyl, $C_{1-6}$ alkoxyalkyl, $C_{3-6}$ cycloalkyl, $C_{4-7}$ cycloalkylalkyl, CN, halogen, $NO_2$, oxo, aryl, heteroaryl, $OR^{17}$, $COOR^{17}$, $COR^{17}$, $CONR^{17}R^{18}$, $COONR^{17}R^{18}$, $SO_2R^{17}$, or $SO_2NR^{17}R^{18}$;

$R^{16}$ is H, $C_{1-6}$ alkyl, $C_{1-6}$ haloalkyl, $C_{1-6}$ alkoxyalkyl, $C_{3-6}$ cycloalkyl, $C_{4-7}$ cycloalkylalkyl, CN, halogen, $NO_2$, $OR^{17}$, $NR^{17}R^{18}$, $COOR^{17}$, $COR^{17}$, $CONR^{17}R^{18}$, $SO_2R^{17}$, $—SO_2NR^{17}R^{18}$, aryl, or heteroaryl;

$R^{17}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;

$R^{18}$ is H, $C_{1-6}$ alkyl, $C_{3-6}$ cycloalkyl, aryl, or heteroaryl, wherein the $C_{1-6}$ alkyl, $C_{3-6}$ cycloalkyl, aryl, or heteroaryl is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy; or $R^{17}$ and $R^{18}$ are taken together with the nitrogen to which they are attached to form a five- to seven-membered heterocyclic ring, which may be saturated or unsaturated and comprises from 1 to 5 heteroatoms selected from the group consisting of nitrogen, oxygen, and sulfur, and is optionally substituted from 1 to 4 times with a substituent selected independently at each occurrence thereof from the group consisting of halogen, hydroxyl, cyano, oxo, $C_1$-$C_4$ alkyl, $C_1$-$C_4$ haloalkyl, and $C_1$-$C_4$ alkoxy; and v is 1 to 8.

18. The conjugate compound according to claim 17, wherein J is —Z—$Y^2$—C(O)—$Y^1$—;

Z is

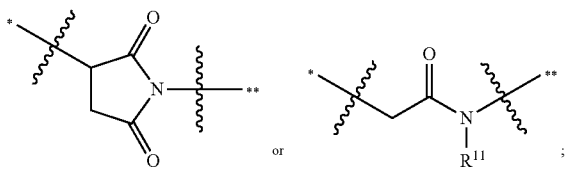

wherein the wavy lines indicate point of attachment sites and * is the point of attachment to L and ** is the point of attachment to $Y^2$;

$Y^1$ is $C_{1-6}$ alkylene or —($X^2$—$CH_2$—$CH_2$)$_1$—, each of which is optionally substituted with $R^8$;

$Y^2$ is $C_{1-6}$ alkylene or —($CH_2CH_2(X^3)$)$_q$—, each of which is optionally substituted with $R^8$;

$X^2$ is independently selected from the group consisting of:
(1) a bond;
(2) ($CH_2$)$_k$;
(3) O; and
(4) $NR^{12}$;

$X^3$ is independently selected from the group consisting of:
(1) a bond;
(2) ($CH_2$)$_k$;
(3) O; and
(4) $NR^{12}$;

$R^{11}$ is H, $C_{1-6}$ alkyl, $C_{1-6}$ hydroxyalkyl, $C_{3-6}$ cycloalkyl, $C_{4-7}$ cycloalkylalkyl, aryl, or heteroaryl, each of which is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;

$R^{12}$ is H, $C_{1-6}$ alkyl, $C_{1-6}$ haloalkyl, $C_{1-6}$ alkoxyalkyl, $C_{3-6}$ cycloalkyl, $C_{4-7}$ cycloalkylalkyl, or $C_{1-6}$ hydroxyalkyl;

k is 1 to 3;
l is 1 to 10; and
q is 1 to 10.

19. The conjugate compound according to claim 17, wherein J is —Z—$Y^3$—;

Z is

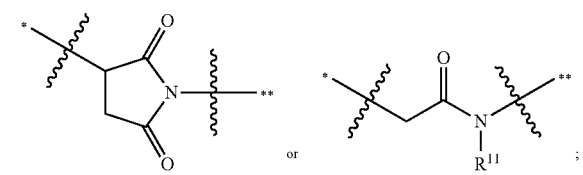

wherein the wavy lines indicate point of attachment sites and * is the point of attachment to L and ** is the point of attachment to $Y^3$;

$Y^3$ is selected from the group consisting of $C_{1-6}$ alkylene, $C_3$-$C_8$ carbocyclyl, O($CH_2$)$_r$, arylene, O($CH_2$)$_r$-arylene, -arylene-($CH_2$)$_r$-, ($CH_2$)$_r$—($C_{3-8}$ carbocyclyl), —($C_{3-8}$ carbocyclyl)-($CH_2$)$_r$, $C_{3-8}$ heterocyclyl, ($CH_2$)$_r$—($C_{3-8}$ heterocyclyl), —($C_{3-8}$ heterocyclyl)-($CH_2$)$_r$, —(($X^4$)($X^5$)($CH_2$)$_r$($X^6$)($CH_2$)$_r$)$_s$—, and —(($X^4$)($X^5$)($CH_2$)$_r$($X^6$)($X^7$)($CH_2$)$_r$)$_s$—, each of which is optionally substituted with $R^8$;

$X^4$, $X^5$, $X^6$, and $X^7$ are each independently selected from the group consisting of a bond, ($CH_2$)$_k$, O, C(O), S, $NR^{19}$, C(O)O, and C(O)$NR^{19}$;

$R^{11}$ is H, $C_{1-6}$ alkyl, $C_{1-6}$ hydroxyalkyl, $C_{3-6}$ cycloalkyl, $C_{4-7}$ cycloalkylalkyl, aryl, or heteroaryl, each of which is optionally substituted from 1 to 3 times with halogen, hydroxyl, cyano, oxo, $C_1$-$C_4$ alkyl, $C_1$-$C_4$ haloalkyl, or $C_1$-$C_4$ alkoxy;

$R^{19}$ is H, $C_{1-6}$ alkyl, $C_{1-6}$ haloalkyl, $C_{1-6}$ alkoxyalkyl, $C_{3-6}$ cycloalkyl, $C_{4-7}$ cycloalkylalkyl, or $C_{1-6}$ hydroxyalkyl;

each r is 0 to 16; and
s is 1 to 10.

20. The conjugate compound according to claim 17, wherein $R^{13}$ and $R^{14}$ are each $C_{1-6}$ alkyl or phenyl.

21. The conjugate compound according to claim 17, wherein J further comprises a thiol-containing spacer.

22. The conjugate compound according to claim 17, wherein L is a protein, a peptide, an amino acid, a receptor ligand, a hormone, or a growth factor.

23. The conjugate compound according to claim 22, wherein L is selected from the group consisting of an antibody, an antibody fragment, scFv-Fc, minibody, diabody, scFv, folic acid, bombesin, EDG, transferrin, gastrin, gastrin-releasing peptide, platelet-derived growth factor, IL-2, IL-6, TFG-alpha, TFG-beta, VGF, insulin, and insulin-like growth factors I and II.

24. The conjugate compound according to claim 22, wherein L is an antibody which binds to one or more tumor-associated antigens or cell-surface receptors selected from (1)-(35):
 (1) BMPR1B (bone morphogenetic protein receptor-type IB, Genbank Accession No. NM—001203);
 (2) E16 (LAT1, SLC7A5, Genbank Accession No. NM—003486);
 (3) STEAP1 (six transmembrane epithelial antigen of prostate, Genbank Accession No. NM—012449);
 (4) 0772P (CA125, MUC16, Genbank Accession No. AF361486);
 (5) MPF (MPF, MSLN, SMR, megakaryocyte potentiating factor, mesothelin, Genbank Accession No. NM—005823);
 (6) Napi3b (NAPI-3B, NPTIIb, SLC34A2, solute carrier family 34 (sodium phosphate), member 2, type II sodium-dependent phosphate transporter 3b, Genbank Accession No. NM—006424);
 (7) Sema 5b (FLJ10372, KIAA1445, Mm.42015, SEMA5B, SEMAG, Semaphorin 5bHlog, sema domain, seven thrombospondin repeats (type 1 and type 1-like), transmembrane domain (TM) and short cytoplasmic domain, (semaphorin) 5B, Genbank Accession No. AB040878);
 (8) PSCA hlg (2700050C12Rik, C530008O16Rik, RIKEN cDNA 2700050C12, RIKEN cDNA 2700050C12 gene, Genbank Accession No. AY358628);
 (9) ETBR (Endothelin type B receptor, Genbank Accession No. AY275463);
 (10) MSG783 (RNF124, hypotheticalproteinFLJ20315, Genbank Accession No. NM—017763);
 (11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank Accession No. AF455138);
 (12) TrpM4 (BR22450, FLJ20041, TRPM4, TRPM4B, transient receptor potential cation channel, subfamily M, member 4, Genbank Accession No. NM_017636);
 (13) CRIPTO (CR, CR1, CRGF, CRIPTO, TDGF1, teratocarcinoma-derived growth factor, Genbank Accession No. NP_003203 or NM_003212);
 (14) CD21 (CR2 (Complement receptor 2) or C3DR (C3d/Epstein Barr virus receptor) or Hs.73792 Genbank Accession No. M26004);
 (15) CD79b (CD79B, CD79β IGb (immunoglobulin-associated beta), B29, Genbank Accession No. NM_000626);
 (16) FcRH2 (IFGP4, IRTA4, SPAP1A (SH2 domain containing phosphatase anchor protein 1a), SPAP1B, SPAP1C, Genbank Accession No. NM_030764);
 (17) HER2 (Genbank Accession No. M11730);
 (18) NCA (Genbank Accession No. M18728);
 (19) MDP (Genbank Accession No. BC017023);
 (20) IL20Rα (Genbank Accession No. AF184971);
 (21) Brevican (Genbank Accession No. AF229053);
 (22) Ephb2R (Genbank Accession No. NM_004442);
 (23) ASLG659 (Genbank Accession No. AX092328);
 (24) PSCA (Genbank Accession No. AJ297436);
 (25) GEDA (Genbank Accession No. AY260763);
 (26) BAFF-R (B cell-activating factor receptor, BLyS receptor 3, BR3, GenBank Accession No. NP_443177.1);
 (27) CD22 (B-cell receptor CD22-B isoform, GenBank Accession No. NP-001762.1);
 (28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation, Genbank Accession No. NP_001774.1);
 (29) CXCR5 (Burkitt's lymphoma receptor 1, a G protein-coupled receptor that is activated by the CXCL13 chemokine, functions in lymphocyte migration and humoral defense, plays a role in HIV -2 infection and perhaps development of AIDS, lymphoma, myeloma, and leukemia, Genbank Accession No. NP_001707.1);
 (30) HLA-DOB (Beta subunit of MHC class II molecule (Ia antigen) that binds peptides and presents them to CD4+T lymphocytes, Genbank Accession No. NP_002111.1);
 (31) P2X5 (Purinergic receptor P2X ligand-gated ion channel 5, an ion channel gated by extracellular ATP, Genbank Accession No. NP_002552.2);
 (32) CD72 (B-cell differentiation antigen CD72, Lyb-2, Genbank Accession No. NP_001773.1);
 (33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis, Genbank Accession No. NP_005573.1);
 (34) FCRH1 (Fc receptor-like protein 1, a putative receptor for the immunoglobulin Fc domain that contains C2 type Ig-like and ITAM domains, Genbank Accession No. NP_443170.1); and
 (35) IRTA2 (Immunoglobulin superfamily receptor translocation associated 2, a putative immunoreceptor with possible roles in B cell development and lymphomagenesis; deregulation of the gene by translocation occurs in some B cell malignancies, Genbank Accession No. NP_112571.1).

25. The conjugate compound according to claim 22, wherein L is folic acid.

26. The conjugate compound according to claim 22, wherein L is epidermal growth factor.

27. The conjugate compound according to claim 17, wherein T is a hydroxyl-containing drug moiety.

28. The conjugate compound according to claim 17, wherein T is an anticancer agent selected from the group consisting of N8-acetyl spermidine, actinomycin, 9-amino camptothecin, aminopterin, anguidine, anthracycline, auristatin, bleomycin, calicheamycin, camptothecin, carminomycin, CC-1065, clofaribine, 1-(2-chloroethyl)-1,2-dimethanesulfonyl hydrazide, cyclopropabenzindol-4-one (CBI), cytarabine, cytosine arabinoside, daunorubicin, dichloromethotrexate, n-(5,5-diacetoxy-pentyl) doxorubicin, 1,8-dihydroxy-bicycle[7.3.1] trideca-4-9-diene-2,6-diyne-13-one, difluoronucleosides, doxorubicin, duocarmycin, epirubicin, esperamicin, etoposide, 5-fluorouracil, irinotecan, leurosideine, leurosine, maytansine, melphalan, 6-mercaptopurine, methopterin, methotrexate, mitomycin A, mitomycin C, morpholine-doxorubicin, butyric acid, cisplatin, diacetoxypentyldoxorubicin, maytansinol, capecitabine, leuprolide, bicalutamide, goserelin, 17-AAG, 17-DMAG, des-acetyl vinblastine, nemorubicin, podophyllotoxin, podophyllotoxin derivatives, retinoic acid, saporin, tallysomycin, vinblastine, vincristine, vindesine, taxane, taxol, paclitaxel, taxotere, docetaxel, taxotere retinoic acid, and isomers, salt forms, analogues, and derivatives thereof.

29. The conjugate compound according to claim 17 having the formula:

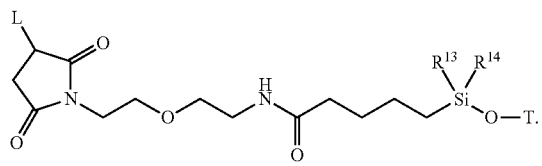

30. The conjugate compound according to claim 17 having the formula:

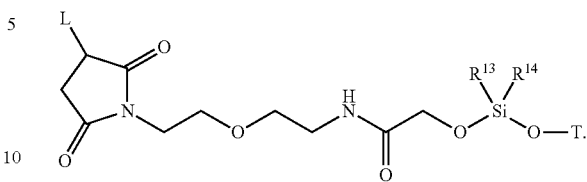

31. A pharmaceutical composition comprising:
a pharmaceutically acceptable carrier and the conjugate compound according to claim 17.

32. A method of therapeutically treating carcinomas of the lung in a subject in need thereof comprising:
selecting a cancer subject in need of therapeutic treatment of carcinoma of the lung, and
administering to the selected subject a therapeutically acceptable amount of a conjugate compound according to claim 17.

* * * * *